(12) United States Patent
Furman et al.

(10) Patent No.: US 7,525,659 B2
(45) Date of Patent: Apr. 28, 2009

(54) SYSTEM FOR DETECTION OF WATER DEFECTS

(75) Inventors: Dov Furman, Rehovot (IL); Gad Neumann, Rehovot (IL); Mark Wagner, Rehovot (IL); Noam Dotan, Givataim (IL); Ram Segal, Netanya (IL); Shai Silberstein, Rishon Le-Zion (IL)

(73) Assignee: Negevtech Ltd., Rehovot (IL)

( * ) Notice: Subject to any disclaimer, the term of this patent is extended or adjusted under 35 U.S.C. 154(b) by 47 days.

(21) Appl. No.: 10/345,097

(22) Filed: Jan. 15, 2003

(65) Prior Publication Data

US 2004/0146295 A1 Jul. 29, 2004

(51) Int. Cl.
G01B 11/00 (2006.01)

(52) U.S. Cl. ...................................... 356/400

(58) Field of Classification Search ... 356/237.2–237.5; 382/145, 149; 348/262
See application file for complete search history.

(56) References Cited

U.S. PATENT DOCUMENTS

| | | | |
|---|---|---|---|
| 3,598,467 A | 8/1971 | Pearson | |
| 4,011,403 A | 3/1977 | Epstein et al. | |
| 4,247,203 A | 1/1981 | Levy et al. | 356/398 |
| 4,323,925 A * | 4/1982 | Abell et al. | 348/340 |
| 4,347,001 A | 8/1982 | Levy et al. | 356/398 |
| 4,360,372 A | 11/1982 | Maciejko | |
| 4,378,159 A | 3/1983 | Galbraith | 356/237 |

(Continued)

FOREIGN PATENT DOCUMENTS

| | | |
|---|---|---|
| EP | 0 557 558 | 9/1993 |
| JP | 61262607 | 11/1986 |
| WO | WO 00/70332 | 11/2000 |

OTHER PUBLICATIONS

"Speckle Reduction" by T.S. McKecknie, pp. 123-170 in Topics in Applied Physics, vol. 9, Laser Speckle and Related Phenomena, edited by J.C. Dainty, Spinger Verlag 1984.

(Continued)

*Primary Examiner*—Gregory J Toatley, Jr.
*Assistant Examiner*—Juan D Valentin
(74) *Attorney, Agent, or Firm*—Ladas and Parry LLP

(57) ABSTRACT

Fast on-line electro-optical detection of wafer defects by illuminating with a short light pulse from a repetitively pulsed laser, a section of the wafer while it is moved across the field of view of an imaging system, and imaging the moving wafer onto a focal plane assembly, optically forming a continuous surface of photo-detectors at the focal plane of the optical imaging system. The continuously moving wafer is illuminated by a laser pulse of duration significantly shorter than the pixel dwell time, such that there is effectively no image smear during the wafer motion. The laser pulse has sufficient energy and brightness to impart the necessary illumination to each sequentially inspected field of view required for creating an image of the inspected wafer die. A novel fiber optical illumination delivery system, which is effective in reducing the effects of source coherence is described. Other novel aspects of the system include a system for compensating for variations in the pulse energy of a Q-switched laser output, methods for autofocussing of the wafer imaging system, and novel methods for removal of repetitive features of the image by means of Fourier plane filtering, to enable easier detection of wafer defects.

3 Claims, 28 Drawing Sheets

U.S. PATENT DOCUMENTS

| | | | | |
|---|---|---|---|---|
| 4,462,662 | A | | 7/1984 | Lama |
| 4,486,776 | A | * | 12/1984 | Yoshida .................. 348/132 |
| 4,556,317 | A | | 12/1985 | Sandland et al. ........... 356/237 |
| 4,579,455 | A | | 4/1986 | Levy et al. ................ 356/394 |
| 4,589,736 | A | | 5/1986 | Harrigan et al. |
| 4,597,665 | A | | 7/1986 | Galbraith et al. ........... 356/237 |
| 4,601,576 | A | | 7/1986 | Galbraith ................... 356/237 |
| 4,618,938 | A | | 10/1986 | Sandland et al. ........... 364/552 |
| 4,639,587 | A | | 1/1987 | Chadwick et al. .......... 250/201 |
| 4,644,172 | A | | 2/1987 | Sandland et al. ........... 250/548 |
| 4,734,923 | A | | 3/1988 | Frankel et al. .............. 378/34 |
| 4,760,265 | A | | 7/1988 | Yoshida et al. ........... 250/492.2 |
| 4,766,324 | A | | 8/1988 | Saadat et al. ............... 250/563 |
| 4,806,774 | A | | 2/1989 | Lin et al. |
| 4,845,558 | A | | 7/1989 | Tsai et al. .................. 358/106 |
| 4,877,326 | A | | 10/1989 | Chadwick et al. .......... 356/394 |
| 4,898,471 | A | | 2/1990 | Stonestrom et al. ......... 356/394 |
| 4,967,095 | A | | 10/1990 | Berger et al. ................ 250/572 |
| 4,969,198 | A | | 11/1990 | Batchelder et al. ............. 382/8 |
| 5,008,743 | A | | 4/1991 | Katzir et al. ................ 358/101 |
| 5,029,975 | A | | 7/1991 | Pease |
| 5,056,765 | A | | 10/1991 | Brandstater .................. 269/20 |
| 5,058,982 | A | | 10/1991 | Katzir ......................... 385/33 |
| 5,076,692 | A | | 12/1991 | Neukermans et al. ....... 356/538 |
| 5,112,129 | A | | 5/1992 | Davidson et al. ............ 356/359 |
| 5,153,668 | A | | 10/1992 | Katzir et al. ................ 356/237 |
| 5,194,959 | A | * | 3/1993 | Kaneko et al. .............. 348/335 |
| 5,264,912 | A | | 11/1993 | Vaught et al. ............... 356/237 |
| 5,267,017 | A | | 11/1993 | Uritsky et al. ............... 356/375 |
| 5,381,004 | A | | 1/1995 | Uritsky et al. ............... 250/307 |
| 5,386,228 | A | * | 1/1995 | Okino ...................... 348/218.1 |
| 5,422,724 | A | | 6/1995 | Kinney et al. ................ 356/375 |
| 5,537,669 | A | | 7/1996 | Evans et al. ................. 382/141 |
| 5,586,058 | A | | 12/1996 | Aloni et al. ................. 364/552 |
| 5,604,585 | A | | 2/1997 | Johnson et al. ............. 356/237 |
| 5,608,155 | A | | 3/1997 | Ye et al. ..................... 73/28.01 |
| 5,617,203 | A | | 4/1997 | Kobayashi et al. |
| 5,619,429 | A | | 4/1997 | Aloni et al. ................. 364/552 |
| 5,619,588 | A | | 4/1997 | Yolles et al. ................ 382/149 |
| 5,659,172 | A | | 8/1997 | Wagner et al. .............. 250/307 |
| 5,699,447 | A | * | 12/1997 | Alumot et al. .............. 382/145 |
| 5,797,317 | A | | 8/1998 | Lahat et al. ............... 101/127.1 |
| 5,798,829 | A | | 8/1998 | Vaez-Iravani ............... 356/237 |
| 5,822,055 | A | | 10/1998 | Tsai et al. ................... 356/237 |
| 5,825,482 | A | | 10/1998 | Nikoonahad et al. ........ 356/237 |
| 5,835,278 | A | * | 11/1998 | Rubin et al. ................. 359/636 |
| 5,864,394 | A | | 1/1999 | Jordan, III et al. .......... 356/237 |
| 5,883,710 | A | | 3/1999 | Nikoonahad et al. ..... 356/237.2 |
| 5,892,579 | A | * | 4/1999 | Elyasaf et al. .............. 356/239.8 |
| 5,907,628 | A | | 5/1999 | Yolles et al. ................ 382/149 |
| 5,912,735 | A | | 6/1999 | Xu ............................. 356/345 |
| 5,917,588 | A | | 6/1999 | Addiego ..................... 356/237 |
| 5,939,647 | A | | 8/1999 | Chinn et al. .............. 73/864.71 |
| 5,970,168 | A | | 10/1999 | Montesanto et al. ........ 382/149 |
| 5,982,921 | A | | 11/1999 | Alumot et al. .............. 382/145 |
| 5,991,699 | A | | 11/1999 | Kulkarni et al. ............... 702/83 |
| 6,020,957 | A | | 2/2000 | Rosengaus et al. ....... 356/237.4 |
| 6,021,214 | A | | 2/2000 | Evans et al. ................. 382/141 |
| 6,064,517 | A | | 5/2000 | Chuang et al. .............. 359/364 |
| 6,075,375 | A | | 6/2000 | Burkhart et al. ............. 324/758 |
| 6,078,386 | A | | 6/2000 | Tsai et al. ................. 356/237.1 |
| 6,099,596 | A | | 8/2000 | Li et al. ..................... 29/25.01 |
| 6,122,046 | A | | 9/2000 | Almogy ................... 356/237.2 |
| 6,124,924 | A | | 9/2000 | Feldman et al. ............. 356/153 |
| 6,169,282 | B1 | | 1/2001 | Maeda et al. ............... 250/310 |
| 6,172,349 | B1 | | 1/2001 | Katz et al. ................ 250/201.3 |
| 6,175,645 | B1 | | 1/2001 | Elyasaf et al. .............. 382/147 |
| 6,175,646 | B1 | | 1/2001 | Schemmel et al. .......... 382/149 |
| 6,178,257 | B1 | | 1/2001 | Alumot et al. .............. 382/145 |
| 6,208,411 | B1 | | 3/2001 | Vaez-Iravani ............ 356/237.2 |
| 6,208,750 | B1 | | 3/2001 | Tsadka ....................... 382/145 |
| 6,215,551 | B1 | | 4/2001 | Nikoonahad et al. ..... 356/237.2 |
| 6,236,454 | B1 | | 5/2001 | Almogy ................... 356/237.3 |
| 6,246,822 | B1 | | 6/2001 | Kim et al. |
| 6,256,093 | B1 | | 7/2001 | Ravid et al. .............. 356/237.2 |
| 6,267,005 | B1 | | 7/2001 | Samsavar et al. ............. 73/105 |
| 6,268,093 | B1 | | 7/2001 | Kenan et al. .................. 430/30 |
| 6,268,916 | B1 | | 7/2001 | Lee et al. .................... 356/369 |
| 6,271,916 | B1 | | 8/2001 | Marxer et al. ............ 356/237.3 |
| 6,274,878 | B1 | | 8/2001 | Li et al. ...................... 250/548 |
| 6,288,780 | B1 | | 9/2001 | Fairley et al. ............ 356/237.1 |
| 6,317,514 | B1 | | 11/2001 | Reinhorn et al. ............ 382/147 |
| 6,324,298 | B1 | * | 11/2001 | O'Dell et al. ............... 382/149 |
| 6,347,173 | B1 | * | 2/2002 | Suganuma et al. .......... 385/115 |
| 6,360,005 | B1 | | 3/2002 | Aloni et al. ................. 382/148 |
| 6,361,910 | B1 | | 3/2002 | Sarig et al. .................... 430/30 |
| 6,366,315 | B1 | * | 4/2002 | Drescher ............... 348/207.99 |
| 6,369,888 | B1 | | 4/2002 | Karpol et al. ............ 356/237.5 |
| 6,456,769 | B1 | | 9/2002 | Furusawa et al. |
| 6,628,681 | B2 | | 9/2003 | Kubota et al. |
| 6,633,375 | B1 | * | 10/2003 | Veith et al. ............... 356/237.4 |
| 6,892,013 | B2 | | 5/2005 | Furman et al. |
| 6,895,149 | B1 | | 5/2005 | Jacob et al. |
| 7,218,389 | B2 | * | 5/2007 | Uto et al. ................. 356/237.2 |
| 2001/0033386 | A1 | | 10/2001 | Kranz et al. |
| 2002/0037099 | A1 | | 3/2002 | Ogawa et al. |
| 2002/0067478 | A1 | | 6/2002 | Karpol et al. ............ 356/237.5 |
| 2003/0227618 | A1 | | 12/2003 | Some |
| 2004/0032581 | A1 | | 2/2004 | Nikoonahad et al. |
| 2005/0084766 | A1 | | 4/2005 | Sandstrom |

OTHER PUBLICATIONS

"Speckle Reduction in Pulsed-Laser Photography" by D. Kohler et al., published in Optics Communications, vol. 12, No. 1, pp. 24-28, Sep. 1974.

"Speckle Reduction with Virtual Incoherent Laser Illumination Using Modified Fiber Array", by Dingel et al., published in Optik, vol. 94, No. 3, pp. 132-136, 1993.

"Machine Vision and Applications", 1998 1:205-221, by IBM Scientists Byron E. Dom, et al.

Patent Abstracts of Japan, vol. 17, No. 613, Jul. 1993 & JP 05 190421.

Patent Abstracts of Japan, vol. 1996, No. 10, Jun. 1996 & JP 08 154210.

Patent Abstracts of Japan, vol. 1999, No. 4, Jan. 1999 & JP 11 014357.

Patent Abstracts of Japen, vol. 1997, No. 3, Nov. 1996 & JP 08 292361.

* cited by examiner

TO FIG 1B

FIG. 1B  FROM FIG. 1A (6) ACQUIRE A DIGITAL IMAGE OF THE FIELD OF VIEW OF THE INSPECTED WAFER DIE, USING THE FOCAL PLANE ASSEMBLY OPTICALLY FORMING A SURFACE OF AT LEAST TWO TWO-DIMENSIONAL CCD MATRIX PHOTO-DETECTORS AT THE FOCAL PLANE OF THE OPTICAL IMAGING SYSTEM, SYNCHRONIZED BY THE CENTRAL CONTROL SYSTEM.
(A) SAVE THE DIGITAL IMAGE DATA IN AN IMAGE MEMORY BUFFER.

(7) REPEAT STEPS (3) THROUGH (6) FOR THE NEXT FIELDS OF VIEW WITHIN THE SAME INSPECTED WAFER DIE, FORMING A STRIP, UNTIL AND INCLUDING THE FIRST EQUIVALENT FIELD OF THE NEAREST NEIGHBORING WAFER DIE IN THE STRIP, SERVING AS A REFERENCE.

(8) PROCESS DIGITAL IMAGE DATA OF A FIELD OF VIEW OF AN INSPECTED WAFER DIE, AND OF THE EQUIVALENT FIELD OF VIEW OF THE NEAREST NEIGHBORING WAFER DIE, SERVING AS A REFERENCE, VIA AN IMAGE PROCESSING SYSTEM.
(A) PERFORM AN IMAGE ALIGNMENT BETWEEN THE INSPECTED FIELD OF VIEW AND THE REFERENCE FIELD OF VIEW BY EXTRACTING IMAGE DATA OF THESE FIELDS OF VIEW FROM THE IMAGE BUFFER.
(B) IDENTIFY THE PRESENCE OF A POTENTIAL WAFER DEFECT BY A COMPARISON METHOD.
(C) SAVE THE COMPARISON DATA IN A DEFECT DATA FILE.
(D) DELETE IMAGE DATA OF THE INSPECTED FIELD OF VIEW OF THE INSPECTED WAFER DIE.

(9) REPEAT STEPS (7) THROUGH (8) FOR SEQUENTIAL FIELDS OF VIEW IN THE STRIP, UNTIL AND INCLUDING THE EQUIVALENT FIELD OF VIEW OF THE NEXT NEAREST NEIGHBORING WAFER DIE IN THE STRIP. STEPS (7) AND (8) ARE DONE IN PARALLEL

(10) DECIDE AND CONFIRM EXISTENCE AND LOCATION OF A WAFER DEFECT, FOLLOWING COMPARISON OF INSPECTED FIELD OF VIEW TO EQUIVALENT FIELDS OF VIEW IN NEIGHBORING WAFER DIES.
(A) SAVE DEFECT DATA IN A WAFER DEFECT DATA FILE.

(11) REPEAT STEPS (7) THROUGH (10) FOR ALL FIELDS OF VIEW WITHIN THE INSPECTED WAFER.

FIG. 3A
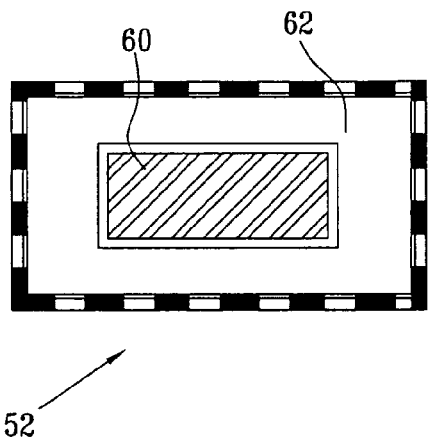
FIG. 3B
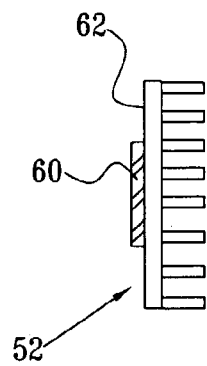
FIG. 4A
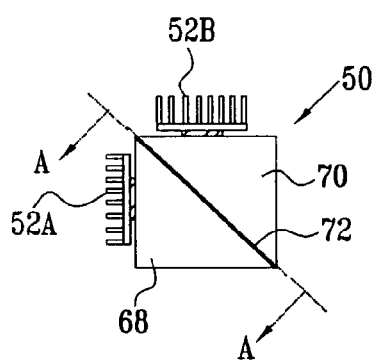
FIG. 4B
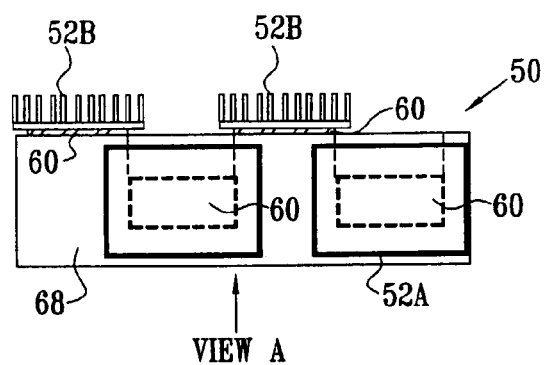
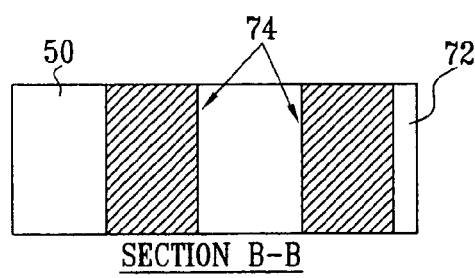
SECTION B-B
FIG. 4C
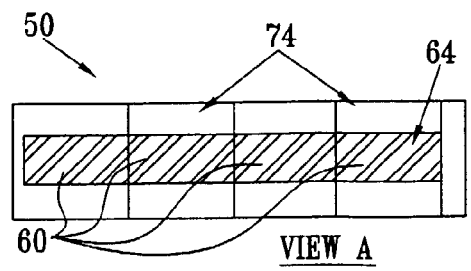
VIEW A
FIG. 4D

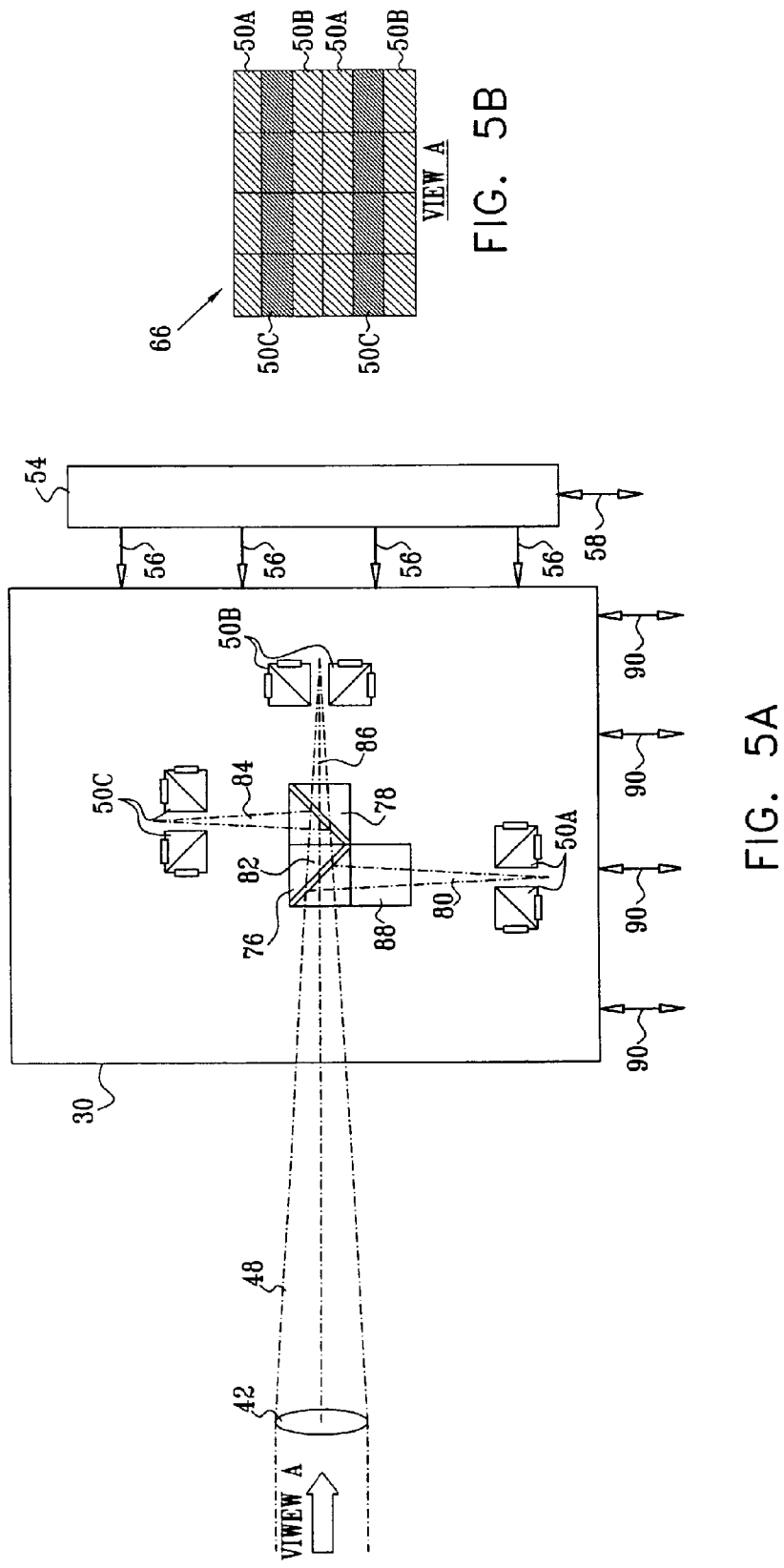

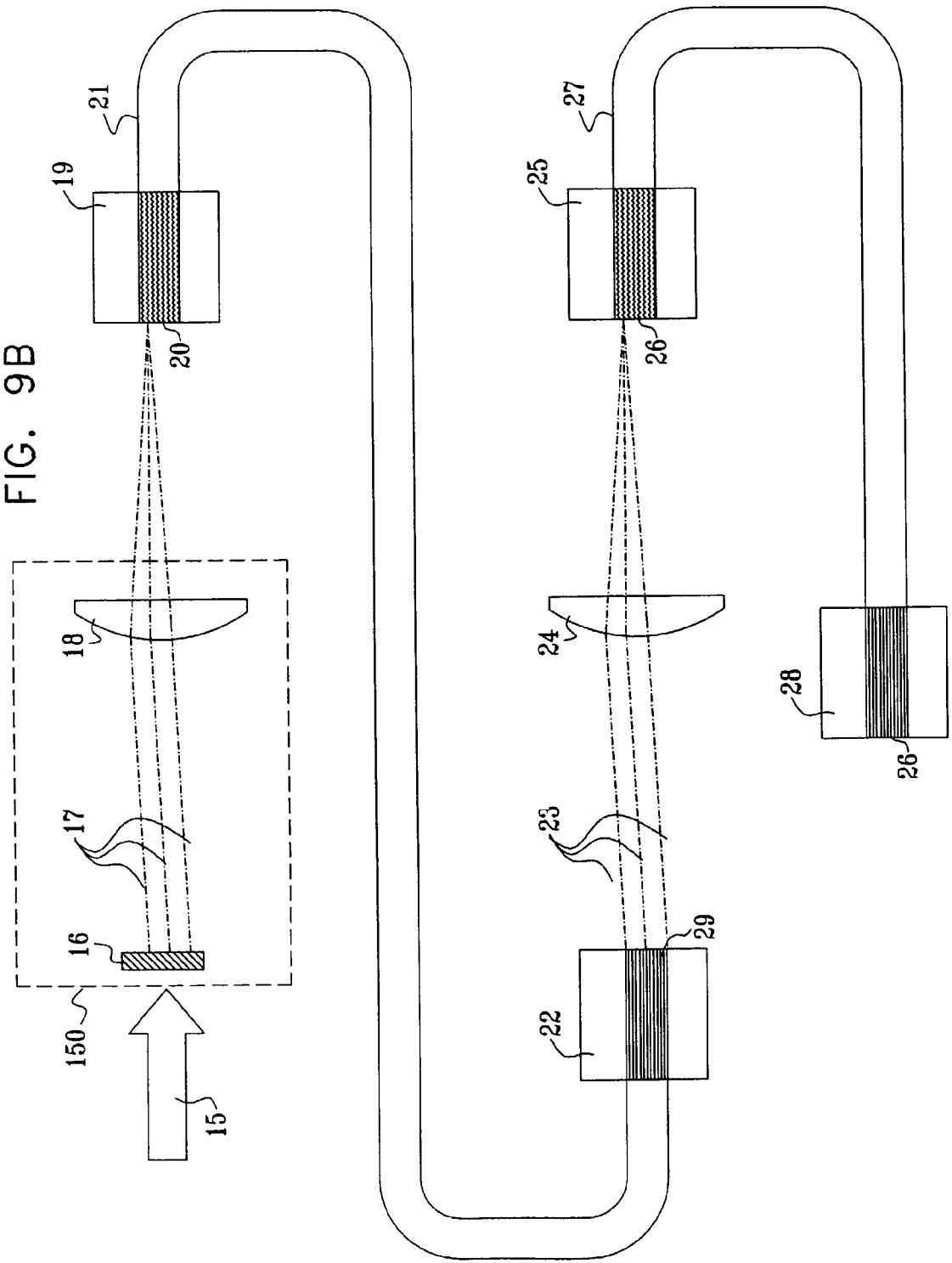

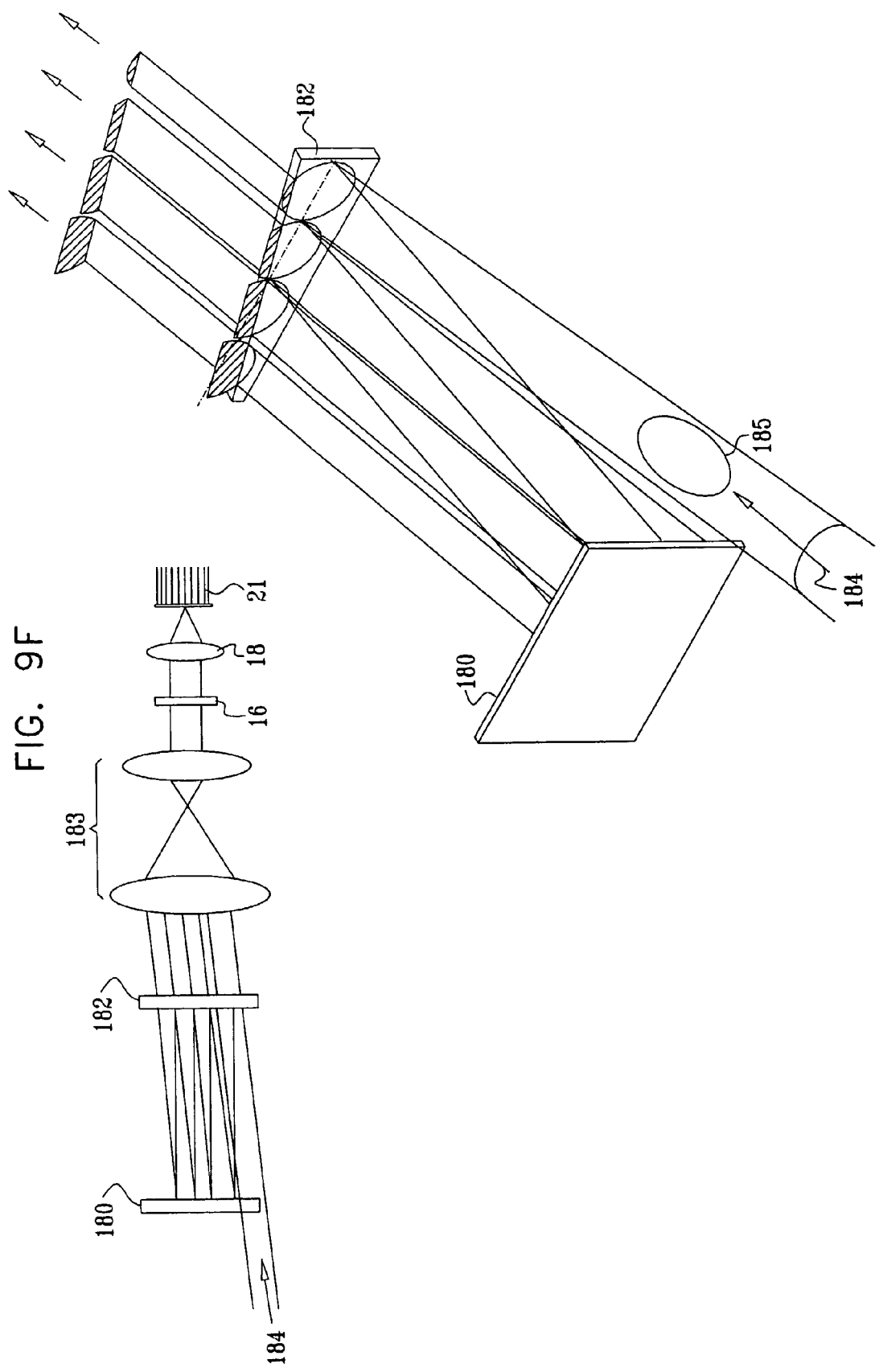

SYSTEM FOR DETECTION OF WAFER DEFECTS

FIELD OF THE INVENTION

The present invention relates to methods and systems for the optical inspection of objects for defects, and in particular, for optically detecting random fabrication defects in semiconductor patterned structures such as integrated circuit dies or chips.

BACKGROUND OF THE INVENTION

Current methods and systems of defect detection on wafers are usually based on comparisons of signals obtained from inspection of a number of adjacent wafer dies or fields of view, featuring a like pattern. Defects produced during wafer fabrication are assumed to be random in nature. Therefore, defect detection is based on a statistical approach, whereby the probability that an identical random defect will be present at the same location within adjacent wafer dies is very low. Hence, defect detection is commonly based on identifying irregularities through the use of the well known method of die-to-die comparison.

A given inspection system is programmed to inspect the pattern of a wafer die or field of view, typically referred to as the inspected pattern, and then to compare it to the identical pattern of a second wafer die or field of view on the same wafer, serving as the reference pattern, in order to detect any pattern irregularity or difference which would indicate the possible presence of a wafer defect. A second comparison between the previously designated inspected pattern and the like pattern of a third wafer die or field of view is performed, in order to confirm the presence of a defect and to identify the wafer die or field of view containing the defect. In the second comparison, the first wafer die or field of view is considered as a reference.

Fabrication of semiconductor wafers is highly complex and very expensive, and the miniature integrated circuit patterns of semiconductor wafers are highly sensitive to process induced defects, foreign-material particulates, and equipment malfunctions. Costs related to the presence of wafer defects are multiplied several fold when going from development stages to mass production stages. Therefore, the semiconductor industry critically depends on a very fast ramp-up of wafer yield at the initial phase of production, and then achieving and controlling a continuous high yield during volume production.

Critical dimensions of integrated circuits on wafers are continuously decreasing, approaching 0.1 micron. Therefore, advanced semiconductor wafers are vulnerable to smaller sized defects than are currently detected. Current methods of monitoring wafer yield involve optically inspecting, in-process, wafers for defects and establishing a feedback loop, with appropriate parametric process control, between the fabrication process and the manufactured wafers. To detect smaller sized defects, optical inspection systems realize increasingly higher resolution by means of scanning wafers using increasingly smaller pixel sizes. Scanning a given sized wafer using increasingly smaller pixel sizes causes a corresponding increase in per wafer inspection time, resulting in decreased wafer throughput, and decreased statistical sampling in terms of the number of inspected wafers. Conversely, attempting to increase wafer inspection throughput by using current optical system pixel sizes results in reducing the effectiveness, i.e., resolution, of wafer defect detection.

In addition to decreasing critical dimensions of wafers, the semiconductor industry is in the process of converting from manufacturing 8-inch wafers to 12-inch wafers. Larger, 12-inch wafers have more than twice the surface area of 8-inch wafers, and therefore, for a given inspection system, inspection time per 12-inch wafer is expected to be twice as long as that per 8-inch wafer. Fabricating 12-inch wafers is significantly more expensive than fabricating 8-inch wafers. In particular, costs of raw materials of 12-inch wafers are higher than those of 8-inch wafers. One result of wafer size conversion, is that cost effective productivity of future wafer manufacturing will depend critically upon increasing speed and throughput of wafer inspection systems.

Automated wafer inspection systems are used for quality control and quality assurance of wafer fabrication processes, equipment, and products. Such systems are used for monitoring purposes and are not directly involved in the fabrication process. As for any principal component of an overall manufacturing system it is important that a wafer inspection method and system of implementation be cost effective relative to the overall costs of manufacturing semiconductor wafers.

There is thus a need to inspect semiconductor wafers for wafer die defects, for wafers featuring larger sizes and smaller critical dimensions, at higher throughput than is currently available, and in a cost effective manner.

Automated optical wafer inspection systems were introduced in the 1980's when advances in electro-optics, computer platforms with associated software and image processing made possible the changeover from manual to automated wafer inspection. However, inspection speed, and consequently, wafer throughput of these systems became technology limited and didn't keep up with increasingly stringent production requirements, i.e., fabricating integrated circuit chips from wafers of increasing size and decreasing critical dimensions.

Current wafer inspection systems typically employ continuous illumination and create a two dimensional image of a wafer segment, by scanning the wafer in two dimensions. This is a relatively slow process, and as a result, quantity of on-line inspection data acquired during a manufacturing process is small, generating a relatively small statistical sample of inspected wafers, translating to relatively long times required to detect wafer fabrication problems. Slow systems of on-line defect detection result in considerable wafer scrap, low wafer production yields, and overall long turn-around-times for pin-pointing fabrication processing steps and/or equipment causing wafer defects.

A notable limitation of current methods and systems of wafer defect detection relates to registration of pixel positions in wafer images. Before wafer defects can be detected by standard techniques of comparing differences in pixel intensities of an image of a targeted or inspected wafer die to pixel intensities of an image of a reference wafer die, the pixel positions of the images of the inspected and reference wafer die need to be registered. Due to typical mechanical inaccuracies during movement of a wafer held on a translation stage, velocity of a wafer beneath a wafer inspection camera system is not constant. As a result of this, image pixel positions in the fields of a detector are distorted and may not be as initially programmed. Therefore, a best fit two-dimensional translation pixel registration correction is performed.

Prior art methods and systems of wafer defect detection, featuring a combination of continuous wafer illumination and acquiring a two dimensional image by either scanning a wafer in two dimensions using a laser flying spot scanner as taught in U.S. Pat. No. 5,699,447, issued to Alumot et al., or scanning a wafer in one dimension using a linear array of photo detectors as taught in U.S. Pat. No. 4,247,203, issued to Levy et al., requires a registration correction for all pixels or all pixel lines. These methods limit system speed, i.e. inspection throughput, and require substantial electronic hardware. Moreover, they result in residual misregistration, since no correction procedure is accurate for all pixels in an image. Residual misregistration significantly reduces system defect detection sensitivity.

An apparatus for photomask inspection is disclosed in U.S. Pat. Nos. 4,247,203, and 4,347,001, both issued to Levy at al. The apparatus described in those patents locates defects or faults in photomasks by simultaneously comparing patterns of adjacent dies on the photomask and locating differences. Using two different imaging channels, equivalent fields of view of each die are simultaneously imaged, and the images are electronically digitized by two linear diode array photo-detectors, each containing 512 pixels.

A two dimensional image of a selected field of view of each die is generated by mechanically moving the object under inspection in one direction, and electronically scanning the array elements in the orthogonal direction. During the detector exposure time, the photomask cannot be moved a distance of more than one pixel or the image becomes smeared. Therefore, the time to scan and inspect the photomask is very long. Since the photomask is moved continuously while the two dimensional images are generated, it is necessary that the photomask move without jitter and accelerations. This motion restriction requires a very massive and accurate air-bearing stage for holding and moving the photomask, which is costly. In addition, the wafer inspection apparatus of Levy et al. is capable of detecting 2.5 micron defects with 95% probability of detection on photomasks.

For critical dimensions of current semiconductor integrated circuits approaching 0.1 micron, this means that the inspecting pixel must be of similar size magnitude. Since inspection speed increases inversely with squared pixel size, the apparatus of Levy et al. would slow down by more than two orders of magnitude. Furthermore, it becomes impractical to implement a motion stage capable of meeting the required mechanical accuracies.

Wafer inspection has also been implemented using a single imaging and detection channel, based on a solid state camera using a two dimensional CCD matrix photo-detector, such as described in 'Machine Vision and Applications', (1998) 1: 205-221, by IBM scientists Byron E. Dom et al. A wafer inspection system designated as P300 is described for inspecting patterned wafers having a repetitive pattern of cells within each die, such as in semiconductor wafers for memory devices. The system captures an image field of view having 480 by 512 pixels.

The image processing algorithms assume a known horizontal cell periodicity, R, in the image, and analyze each pixel in the image by comparing it with two pixels, one pattern repetition period, R, away in either horizontal direction. Such a comparison of like cells within a single image is called a cell-to-cell comparison. The pixel under test is compared with periodic neighbors on both sides to resolve the ambiguity that would exist if it were compared with only a single pixel.

While this system is capable of simultaneously capturing a two dimensional image of the object under test, it is very slow in inspecting an entire wafer. Millions of image fields are needed to image an entire wafer. Since the system uses continuous illumination, such as is used with standard microscopes, the wafer must be moved, under the inspection camera, from field to field and stopped during the image exposure to avoid image smear. To reach another field, the mechanical motion stage carrying the wafer must accelerate and then decelerate to a stop at a new position. Each such motion takes a relatively long time and therefore inspecting a wafer typically takes many hours.

Increased illumination of the inspected area can be achieved using laser illumination. However, the nature of a laser beam, and especially its coherent nature, presents a number of problems when used as such an illuminating source in applications requiring a uniform illuminating flux over the inspected area, such as is required, for instance, in a wafer inspection system:

(i) Interference of light in the illumination optics creates non-uniformity in the illumination field.

(ii) Interference of the illuminated light by the structured pattern on the wafer creates artifacts in the image.

(iii) Surface roughness creates speckle that generates non-uniformity in the image.

(iv) The laser beam itself is generally not uniform. Using the laser beam directly as a light source creates non-uniform illumination.

In order to overcome items (i) to (iii) above, the effects of the coherent nature of the laser beam must be reduced and preferably eliminated completely. This process is known as coherence breaking.

There are two definitions related to the coherence of a laser beam:

(a) Spatial coherence, which is the phase relation between each spatial point in the laser beam spot. This allows different points in the spot to interact with each other in a destructive or constructive manner when the spot is illuminating a cyclic pattern or a rough surface. This quality depends mainly on the mode of the beam. For instance in the basic mode ($TEM_{00}$) the spatial coherence is defined by the Gaussian profile of the beam.

(b) Temporal coherence, which is a measure of the time or the transit distance (the time multiplied by the speed of light in the medium concerned) over which the phase of the beam can be defined. This parameter depends on the type of laser and its spectral bandwidth. Thus, for instance, for the second harmonic of a Nd:YAG laser at 532 nm, the coherence length is about 8 mm in free space.

There are a number of methods described in the prior art for overcoming coherence effects in using laser illumination. Reference is made to the articles "Speckle Reduction" by T. S. McKecknie, pp. 123-170 in Topics in Applied Physics, Vol. 9, Laser Speckle and Related Phenomena, edited by J. C. Dainty, Springer Verlag (1984), "Speckle reduction in pulsed-laser photography" by D. Kohler et al., published in Optics Communications, Vol. 12, No. 1, pp. 24-28, (Sept. 1974) and "Speckle reduction with virtual incoherent laser illumination using modified fiber array" by B. Dingel et al., published in Optik, Vol. 94, No. 3, pp. 132-136, (1993), and to U.S. Pat. No. 6,369,888 to A. Karpol et al., for "Method and Apparatus for Article Inspection including Speckle Reduction".

The disclosures of all of the publications and documents mentioned in this section, and in other sections of this application are all herein incorporated by reference, each in its entirety.

The above-mentioned prior art solutions to the problem of coherence breaking variously have specific disadvantages, and it is an object of the present invention to attempt to overcome some of these advantages.

SUMMARY OF THE INVENTION

The present invention relates to a method and system for fast on-line electro-optical detection of wafer defects. In accordance with a preferred embodiment of the present invention the detection is achieved by illuminating a molting wafer, using a short light pulse from a pulsed laser directed to a field of view of an electro-optical camera system having microscopy optics, and imaging the moving wafer onto a focal plane assembly (FPA). The FPA is defined by optically forming a surface of photo-detectors at the focal plane of an optical imaging system, formed from several detector ensembles, each detector ensemble including an array of several two-dimensional matrix photo-detectors. Each two-dimensional matrix photo-detector produces an electronic image featuring a matrix of picture elements (pixels), such that the simultaneously created images from the matrix photo-detectors are processed in parallel using image processing techniques. The imaged field of view is compared with another field of view serving as a reference, in order to find differences in corresponding pixels, indicative of the presence of a wafer die defect.

For a wafer inspection method or system in which all focal plane assembly pixels in any given field can be considered as one unit, generated simultaneously, there is no need for image pixel registration within a field of view of a focal plane assembly. Therefore, only a single two dimensional alignment correction between the inspected field of view and the equivalent zone in a reference field of view is needed and a single alignment correction is correct over the entire focal plane assembly field of view. Such a procedure results in negligible residual misregistration, enabling improved defect detection sensitivity.

Hereinafter, the term 'wafer' refers to, and is generally considered to feature individual patterned structures, known as 'semiconductor wafer dies', 'wafer dies', or wafer chips'. Current semiconductor technology involves the physical division of a single wafer into identical dies for the manufacture of integrated circuit chips, such that each die becomes an individual integrated circuit chip having a specific pattern, such as a memory chip or a microprocessor chip, for example. The type of chip produced from a given die is not relevant to the method or system of the present invention.

Hereinafter, the term 'field of view' refers to that part or segment of, a wafer, in general, and a wafer die, in particular, illuminated by a pulsed laser and imaged by the electro-optical camera system inspection optics in conjunction with the FPA. Accordingly, an entire single wafer die, and therefore, an entire single wafer featuring a plurality of wafer dies, is inspected by sequential imaging of a plurality or sequence of fields of view. The field of view can be considered as the inspection system electro-optical imaging footprint on the wafer or wafer die. Successive fields of view created while the wafer is moving in one direction are referred to as a 'strip' of fields of view. Pixels are referred to with respect to forming an image of a field of view by the electro-optical inspection system. As a reference dimension, a general order of magnitude of the size of a typically square wafer die within a wafer is 1 centimeter by 1 centimeter, or $10^4$ microns by $10^4$ microns.

Hereinafter, detection of a 'wafer defect' refers to the detection of the presence of an irregularity or difference in the comparison of like patterns of wafer dies or like patterns of fields of view.

In particular, the method and system of the present invention enable capturing high pixel density, large field of view images of a wafer die, on-the-fly, without stopping movement of the wafer. High accuracy of wafer motion speed is not needed, and a relatively simple inexpensive mechanical stage for moving the wafer can be used. The continuously moving wafer is illuminated with a laser pulse of such short duration, for example, ten nanoseconds, significantly shorter than the image pixel dwell time, that there is effectively no image smear during the wafer motion. During the time interval of the laser pulse, a wafer die image moves less than a tenth of a pixel. The laser pulse has sufficient energy and brightness to impart the necessary illumination to the inspected field of view required for creating an image of the inspected wafer die.

In a preferred embodiment, as a result of the method and system featuring optical coupling of the separate CCD matrix photo-detectors via the detector ensembles and the focal plane assembly, processing time of an entire array of, for example, twenty-four CCD matrix photo-detectors, having imaging capacity of 48 megapixels, is equivalent to processing time of a single CCD matrix photo-detector of the order of $\frac{1}{30}$ of a second, since the processing of all the photo-detectors is processed in parallel. Consequently, parallel processing of the entire focal plane assembly including twenty-four CCD matrix photo-detectors provides an overall pixel processing data rate of nearly 1.5 gigapixels per second. Furthermore, the overall wafer inspection system operates essentially at 100% efficiency, whereby, the laser pulse rate of 30 pulses per second is synchronized with the frame speed of 30 frames per second of each CCD matrix photo-detector, and the wafer is moved at a linear speed such that the distance between successive fields of view is covered in $\frac{1}{30}$ of a second.

The method and system of the present invention provide significant improvements over currently used methods and systems for electro-optical inspection and detection of wafer defects, in the semiconductor wafer fabrication industry, including providing high resolution large field of view wafer die images at very high wafer inspection throughput, and requiring less electronic and system hardware. Moreover, by employing an array of several CCD matrix photo-detectors for acquiring a high pixel density image of a wafer die illuminated by a single light pulse, the method and system of the present invention prevents misregistration of pixel positions in the wafer die images, enabling enhanced defect detection sensitivity. Such a method and system of wafer defect detection results in faster, more efficient, and cost effective, feedback control of wafer fabrication processes than available in the prior art.

The present invention also seeks to provide a new fiber optical illumination delivery system, which is effective in reducing the speckle effects arising from source coherence. The system preferably utilizes either a single bundle of optical fibers, or serial bundles of optical fibers, according to the various preferred embodiments of the present invention. The single bundle embodiment differs from prior art systems in that the differences in optical lengths between different fibers of the bundle is preferably made to be equal to or more preferably less than the coherence length of the source illumination. This preferred embodiment enables construction of an illumination system delivering a higher level of illumination, but without greatly affecting the coherence breaking abilities of the system.

The serial bundle embodiment differs from prior art systems as described hereinbelow: Whereas in prior art systems, in one bundle comprising the fibers the differences in lengths of the fibers therein is made equal to the overall difference in length between the shortest and the longest fibers in the other bundle, according to a preferred embodiment of this invention, there are provided groups of fibers of the same length, and it is the difference in lengths of these groups which is made equal to, or even more preferably, less than the overall difference in length between the shortest and the longest fibers in the other bundle. This preferred embodiment also enables construction of an illumination system delivering a higher level of illumination, but without greatly affecting the coherence breaking abilities of the system.

Thus, according to the present invention, there is provided a method for electro-optically inspecting a patterned semiconductor wafer of dies for a defect, the method comprising the steps of: (a) moving the patterned wafer along an inspection path; (b) providing a repetitively pulsed laser illuminating source; (c) sequentially illuminating each of a plurality of fields of view in each of a plurality of the wafer dies by using the pulsed laser illuminating source; (d) sequentially acquiring an image of the each of the plurality of the sequentially illuminated fields of view in each of a plurality of the wafer dies by using an electro-optical camera including at least two two-dimensional matrix photo-detectors, the at least two two-dimensional matrix photo-detectors simultaneously acquiring images of each of the plurality of the sequentially illuminated fields of view in each of a plurality of the wafer dies; and (e) detecting a wafer defect by comparing the sequentially acquired images of each of the plurality of the sequentially illuminated fields of view in each of a plurality of the wafer dies using a die-to-die comparison method.

According to still further features in the described preferred embodiments, the repetitively pulsed laser is a Q switched Nd:YAG laser.

According to still further features in the described preferred embodiments, the Q switched Nd:YAG laser is optically pumped by light emitting diodes.

According to still further features in the described preferred embodiments, the electro-optical camera further includes a non-linear optical crystal functioning as a second harmonic generating crystal, placed in a laser beam light path of the repetitively pulsed laser illumination source, the non-linear optical crystal halving wavelengths of the laser beam light generated by the repetitively pulsed laser.

According to the present invention, there is provided a system for electro-optically inspecting a patterned semiconductor wafer of dies for a defect, the system comprising: (a) a mechanism for providing movement of the patterned water along an inspection path; (b) a repetitively pulsed laser illumination source for illuminating the patterned wafer; (c) an electro-optical camera including at least two two-dimensional matrix photo-detectors for sequentially acquiring an image of each of a plurality of sequentially illuminated fields of view in each of a plurality of the wafer dies, the at least two two-dimensional matrix photo-detectors operate with a mechanism for simultaneous acquisition of images of each of the plurality of the sequentially illuminated fields of view in each of a plurality of the wafer dies; and (d) an image processing mechanism for processing the sequentially acquired images of each of the plurality of the illuminated fields of view in each of a plurality of the wafer dies and detecting a wafer defect by comparing the sequentially acquired images using a die-to-die comparison method.

According to the present invention, there is provided an electro-optical camera for inspecting a patterned semiconductor wafer of dies for a defect, comprising a focal plane assembly including at least one detector ensemble, the detector ensemble includes an array of at least two two-dimensional matrix photo-detectors operating with a mechanism for simultaneous acquisition of images of each of a plurality of illuminated fields of view in each of a plurality of the wafer dies.

Implementation of the method and system of the present invention involves performing or completing tasks or steps manually, automatically, or a combination thereof. Moreover, according to actual instrumentation and equipment of a given wafer inspection system, several steps of the present invention could be implemented by hardware or by software on any operating system of any firmware or a combination thereof. For example, as hardware, indicated steps of the invention could be implemented as a chip or a circuit. As software, indicated steps of the invention could be implemented as a plurality of software instructions being executed by a computer using any suitable operating system. In any case, indicated steps of the method of the invention could be described as being performed by a data processor, such as a computing platform for executing a plurality of instructions.

In accordance with yet another preferred embodiment of the present invention, there is provided an inspection system for inspecting objects comprising an imager operative to image the objects, while the objects are illuminated and are in motion along a travel path, a transporter for providing relative motion between the imager and the objects along the travel path, and a pulsed object illuminator for illuminating the objects as they travel along the travel path. According to further preferred embodiments, the imager may employ one or more two-dimensional detector arrays Furthermore, the above described inspection system may also preferably comprise a synchronizer for synchronizing operation of the pulsed object illuminator with the operation of the transporter. This synchronizer preferably comprises an illumination trigger operative to generate an illumination activating signal each time the transporter has brought one of the objects to a new imaging position vis-a-vis the imager.

In any of these embodiments of the inspection system, the pulsed object illuminator preferably comprises a laser.

There is further provided in accordance with yet another preferred embodiment of the present invention, an inspection system as described above, and wherein the imager comprises at least two two-dimensional detector arrays which acquire images simultaneously. These at least two two-dimensional detector arrays may be optically coupled such that they together define a generally non-interrupted planar detector plane. Additionally, the at least two two-dimensional detector arrays are preferably arranged in a non-mutually coplanar arrangement.

In accordance with still another preferred embodiment of the present invention, there is provided an inspection system as described above, and wherein the speed of operation of the transporter and the pulse length of the pulsed object illuminator are selected such that image smearing of less than one pixel is produced.

In accordance with still another preferred embodiment of the present invention, in the above-described embodiments of the inspection system, the pulsed object illuminator provides both dark field and bright field illumination of the objects as they travel along the travel path. Furthermore, the pulsed object illuminator may provide obscured orthogonal dark field illumination of the objects as they travel along the travel path.

Additionally, in accordance with a further preferred embodiment of the present invention, the objects may preferably include multiple identical regions, and the inspection system may also comprise an imaging comparator for comparing images of individual ones of the multiple identical regions.

There is also provided in accordance with yet a further preferred embodiment of the present invention, an inspection system as described above, and wherein the pulsed object illuminator comprises at least one fiber optics bundle. The at least one fiber optics bundle may preferably comprise a plurality of optical fibers, at least some of which have differing optical lengths, the plurality of optical fibers having differing optical lengths having differences in optical lengths therebetween which are less than a coherence length of light passing therealong.

There is even further provided in accordance with a preferred embodiment of the present invention, an inspection system for inspecting objects comprising an object illumination source emitting pulses of illumination, at least one fiber optics bundle onto which the illumination is incident, and a pulse stretcher for lengthening the duration of the pulses, wherein the pulse stretcher is disposed between the source and that of the at least one fiber optics bundle on which the illumination is incident first. This pulse stretcher may preferably comprise a first and a second mirror disposed a predetermined distance apart such that illumination directed between them is multiply reflected between them, the position of incidence at each of the multiple reflections being displaced in a lateral direction across the first and second mirrors, and wherein one of the mirrors has a progressively cut away profile in the lateral direction, such that at each reflection at the mirror, part of the illumination incident is output from the pulse stretcher.

Furthermore, in accordance with yet another preferred embodiment of the present invention, there is provided a method of eliminating repetitive features from an image of an object, comprising the steps of illuminating the object with a plurality of at least partially coherent sources, wherein the coherence of at least some of the sources is independent of that of others of the sources, forming an image of the illuminated object by means of an objective element having a back focal plane, and positioning a mask having a predetermined shape at the back focal plane of the objective element, such that information related to the repetitive features is filtered out.

There is also provided in accordance with a further preferred embodiment of the present invention, an inspection system for inspecting an object comprising an objective element for imaging the object, the objective element having a back focal plane, a detector disposed at an image plane of the objective element for receiving an image of the object, and an auxiliary lens, which when disposed between the objective element and the image plane, projects an image of the back focal plane of the objective lens onto the detector, such that optical information relating to the object and located at the back focal plane, may be determined.

In accordance with yet another preferred embodiment of the present invention, there is provided a method of inspecting an object, comprising the steps of providing an objective element disposed to form an image of the object at an image plane, the objective element having a back focal plane, disposing a detector at the image plane to detect the image of the object, disposing an auxiliary lens between the objective element and the detector, such that the auxiliary lens projects an image of the back focal plane onto the detector, and utilizing the image of the back focal plane to determine optical information at the back focal plane relating to the object. The above described method may preferably also include the steps of using the optical information relating to the object to construct a mask for optically blocking predetermined parts of the information, and disposing the mask at the back focal plane such that features of the object related to the optical information are eliminated from the image. These features may preferably be repetitive features of the object.

There is further provided in accordance with yet another preferred embodiment of the present invention, a mask for blocking repetitive information from the back focal plane of an objective, the mask comprising a plurality of blocking elements, the elements being moveable across the back focal plane, and wherein the elements are positioned in the back focal plane such as to block predetermined information in the back focal plane. These blocking elements are preferably supported on adjustable thin wires, such that the position of the blocking elements in the mask may be positioned by means of the adjustable wires according to the predetermined information in the back focal plane. The wires should preferably be sufficiently thin that they do not block information to be imaged.

In accordance with still another preferred embodiment of the present invention, there is provided apparatus for determining the position of optimum focus of the imaging system of an object inspection system, comprising an objective element projecting an image of the object onto an imaging plane, a detector disposed at the imaging plane and tilted at an angle to the imaging plane, such that the sharpness of focus of the image varies across the detector, and a focal position calculator operative to determine the point of optimum image sharpness on the detector. The imaging system may be precalibrated such that when the imaging system is in the position of optimum focus, the point of optimum image sharpness on the detector is in a known position. Furthermore, the focal position calculator preferably utilizes an image processing algorithm to determine the point of optimum image sharpness.

Additionally, in the above described apparatus for determining the position of optimum focus of the imaging system, the determination of the position of optimum focus may be generated using illumination of a different wavelength from that used for the object inspection. In such a case, the object inspection may preferably be performed with illumination of a first wavelength in a dark field mode, and determining the position of optimum focus of the imaging system may preferably be performed with illumination of a second wavelength in a bright field mode.

There is further provided in accordance with still another preferred embodiment of the present invention, apparatus for determining the optimum position of focus of an imaging system, the imaging system having an optical axis and an imaging plane perpendicular thereto, and comprising (a) an objective element projecting an image of an object onto the imaging plane, (b) a detector disposed at the imaging plane, (c) a source of illumination having an emission aperture, disposed at a distance from the object, and, by means of a beam splitter, essentially confocally to the imaging plane, the source being tilted at an angle such that different points across the emission aperture are located at different distances from the object, such that the sharpness of images of the different points on the imaging plane vary across the detector, and (d) a focal position calculator operative to determine the point of optimum sharpness on the detector, and the optimum position of focus therefrom. The imaging system of this apparatus is preferably precalibrated such that when it is in the optimum position of focus, the point of optimum image sharpness on the detector is in a known position.

Furthermore, the focal position calculator preferably utilizes an image processing algorithm to determine the point of optimum image sharpness. Additionally, in the above described apparatus, the determination of the position of optimum focus may be generated using illumination of a different wavelength from that used for the object inspection. In such a case, the object inspection may preferably be performed with illumination of a first wavelength in a dark field mode, and determining the position of optimum focus of the imaging system may preferably be performed with illumination of a second wavelength in a bright held mode.

In the above described apparatus, the tilted source of illumination may comprise a flat array of optical fibers, whose ends are terminated in a line non-perpendicularly to the axis of illumination of the array. Alternatively and preferably, it may comprise a mask comprising a plurality of illuminated holes, and wherein the mask is tilted non-perpendicularly to the axis of the illumination.

In accordance with a further preferred embodiment of the present invention, there is also provided apparatus for determining the optimum position of focus of an imaging system, the imaging system having an optical axis and an imaging plane perpendicular thereto, and comprising (a) an objective element projecting an image of an object onto the imaging plane, (b) a source of illumination having an emission aperture, disposed at a distance from the object, and, by means of a beam splitter, essentially confocally to the image plane, the source being tilted at an angle such that different points across the emission aperture are located at different distances from the object, such that the sharpness of images of the different points on the imaging plane vary across the detector, (c) first and second detectors disposed such that the first detector is located closer to the objective element than the imaging plane, and the second detector is located further from the objective element than the imaging plane, (d) a second beam splitter for projecting the image onto each of the two detectors, such that the sharpness of the image on the detectors is differently dependent on the position of focus, and (e) a focal position calculator operative to determine the point of optimum sharpness on each of the detectors, and the optimum position of focus therefrom.

The imaging system of this apparatus is preferably precalibrated such that when it is in the optimum position of focus, the point of optimum image sharpness on the detector is in a known position. Furthermore, the focal position calculator preferably utilizes an image processing algorithm to determine the point of optimum image sharpness. Additionally, in the above described apparatus, the determination of the position of optimum focus may be generated using illumination of a different wavelength from that used for the object inspection. In such a case, the object inspection may preferably be performed with illumination of a first wavelength in a dark field mode, and determining the position of optimum focus of the imaging system may preferably be performed with illumination of a second wavelength in a bright field mode.

There is also provided in accordance with yet a further preferred embodiment of the present invention, a dark field illuminating system for illuminating an object plane at non-perpendicular incidence, comprising an illuminating source beam having a cross section of form such that it reduces elongation of the beam on the object plane generated by virtue of the angle of incidence of the illuminating beam on the object plane. In this dark field illuminating system, the illumination source beam may be generated by means of a fiber illuminating bundle having a predetermined output section, such as to provide the cross section of the illumination source beam. Furthermore, this predetermined output section of the fiber illuminating bundle may preferably be an essentially rectangular section. The system may preferably include a cylindrical focussing element for generating the required cross section of the beam.

There is even further provided in accordance with a preferred embodiment of the present invention, a system for compensating for variations in the pulse energy of a Q-switched laser output, comprising (a) a monitor detector sampling a part of the laser output, and determining the pulse energy of the laser, (b) a pulse energy comparator circuit which compares the energy of a laser pulse with that of at least one previous laser pulse, (c) a pulse energy trend calculator which utilizes information from the comparator circuit to determine the temporal trend in pulse energy, and (d) a Q-switch delay generator receiving information from the pulse energy trend calculator, and adjusting the Q-switch delay time such as to reduce the variations in the pulse energy detected in the laser output.

Furthermore, in accordance with yet another preferred embodiment of the present invention, there is provided a system for compensating for variations in laser pulse energy of a Q-switched, optically-pumped laser output, arising from changes in optical pump pulse energy, comprising, (a) a monitor detector sampling a part of the optical pump output, and determining the optical pump pulse energy, (b) a pump pulse energy comparator circuit which determines the energy of the optical pump pulse with that of a known optical pump pulse energy, (c) a pump pulse energy difference calculator which utilizes information from the comparator circuit to determine the change in pump pulse energy from the known pump pulse, and (d) a Q-switch delay generator receiving information from the pump pulse energy difference calculator, and adjusting the Q-switch delay time such as to reduce variations in the pulse energy detected in the laser output. In this system, the monitor detector sampling a part of the output of the optical pump may preferably be located inside the enclosure of the laser.

There is also provided in accordance with a further preferred embodiment of the present invention, a system for compensating for variations in the pulse energy of an optically pumped Q-switched laser output, whether arising from changes in the optical pump pulse energy, or from other origins, and comprising the components of the embodiments described in both of the previous two paragraphs.

There is even further provided in accordance with a preferred embodiment of the present invention, a method for compensating for changes in the output level of an illumination source for a system for the inspection of objects, comprising the steps of (a) sampling the output level of the illumination source, (b) comparing the output level to a predetermined level, (c) determining changes in the output level, (d) generating a digital output representative of the object, and (e) adjusting the gray level of the digital output to compensate for the changes in the output level of the illumination source.

There is also provided in accordance with a preferred embodiment of the present invention, an optical system for reducing the coherence of a beam for illumination of the wafer, comprising a source of at least partially coherent illumination, at least part of which has a characteristic coherence length, and at least one fiber optics bundle comprising a plurality of optical fibers, at least some of which have differing optical lengths, at least some of the fibers of differing optical length having differences in optical lengths therebetween which are less than the characteristic coherence length.

In the above system, the source of at least partially coherent illumination may preferably be a laser source, and the coherent illumination may have spatial coherence or temporal coherence or both. To reduce spatial coherence, the plurality of optical fibers in the at least one fiber optics bundle are preferably randomly ordered. Furthermore, a diffusing element may be used for spatial mixing of the beam. The optical system may also comprise an optical element positioned such that it is operative to direct the illumination from any point of the beam into essentially each of the plurality of fibers.

According to yet another preferred embodiment of the present invention, in the above described optical system, the differences in optical lengths being less than the characteristic coherence length, results in a bundle having reduced transmission losses.

In accordance with still another preferred embodiment of the present invention, the illumination beam comprises pulses having a characteristic length, and the bundle is operative to stretch the length of the pulses.

There is further provided in accordance with still another preferred embodiment of the present invention, an optical system for reducing the coherence of a beam for illumination of a wafer, comprising a source of at least partially coherent illumination, at least part of the illumination having a characteristic coherence length, a first fiber optics bundle comprising a plurality of optical fibers, at least some of which have differing optical lengths, at least some of the fibers of differing optical length having differences in optical lengths therebetween which are less than the characteristic coherence length, and a second fiber optics bundle disposed serially with the first bundle, comprising a plurality of groups of optical fibers, each group of fibers comprising fibers of essentially the same length, and wherein at least some of the group of fibers have differing optical lengths, at least some of the groups of fibers having differences in optical lengths therebetween which are at least equal to the sum of the optical length differences of the fibers in the first bundle.

In the above-described embodiment, each of the groups may have essentially the same number of fibers, or alternatively and preferably, the number of fibers in each of the groups may increase according to the optical length of the group, and even more preferably, the number of fibers in each group may generally be proportional to the length of the group.

The bundles may be arranged serially such that the beam for illumination of the wafer is initially incident on the first bundle or alternatively and preferably, the beam for illumination of the wafer is initially incident on the second bundle. In either case, according to further preferred embodiments of this invention, an optical element is positioned between the bundles such that it is operative to direct illumination from any point of the output of the first bundle onto essentially each point of the input of the second bundle.

In the above system, the source of at least partially coherent illumination may preferably be a laser source, and the coherent illumination may have spatial coherence or temporal coherence or both. To reduce spatial coherence, the plurality of optical fibers in the at least one fiber optics bundle are preferably randomly ordered. Furthermore, a diffusing element may be used for spatial mixing of the beam.

In accordance with still a further preferred embodiment of the present invention, there is also provided a method of reducing the transmission loss in a fiber optical bundle for reducing the coherence of light transmitted therethrough, at least part of which light has a characteristic coherence length, the method comprising the steps of providing at least one fiber optical bundle comprising a plurality of optical fibers, at least some of which have differing optical lengths, and arranging the lengths of the plurality of optical fibers such that at least some of the fibers of differing optical lengths have differences in optical length therebetween generally less than the characteristic coherence length.

BRIEF DESCRIPTION OF THE DRAWINGS

The present invention will be understood and appreciated more fully from the following detailed description, taken in conjunction with the drawings in which:

FIGS. 1A and 1B are together a flow diagram of a preferred embodiment of the method for fast on-line electro-optical detection of wafer defects, in accordance with the present invention;

FIG. 3A is a schematic diagram illustrating a top view of a CCD matrix photo-detector, in accordance with the present invention;

FIG. 3B is a schematic diagram illustrating a side view of a CCD matrix photo-detector, in accordance with the present invention;

FIG. 4A is a schematic diagram illustrating a close-up side view of a detector ensemble, including CCD matrix photo-detectors, and prisms, in accordance with the present invention;

FIG. 4B is a schematic diagram illustrating another close-up side view of a detector ensemble, including CCD matrix photo-detectors, and prisms, in accordance with the present invention;

FIG. 4C is a schematic diagram illustrating a close-up view of a surface of a glass prism, including zones of highly reflective coating, as part of the detector ensemble shown in FIGS. 4A-4B, in accordance with the present invention;

FIG. 4D is a schematic diagram illustrating a close-up front optical view, of the detector ensemble shown in FIGS. 4A-4C, showing the appearance of an optically continuous surface of photo-detectors, featuring a plurality of CCD matrix photo-detectors, in accordance with the present invention;

FIG. 5A is a schematic diagram illustrating a close-up view of the focal plane assembly, including beam splitting prisms and detector ensembles, in accordance with the present invention;

FIG. 5B is a schematic diagram illustrating an optically formed continuous surface of photo-detectors at the focal plane formed by the detector ensembles of the focal plane assembly and including several CCD matrix photo-detectors, in accordance with the present invention;

FIG. 5C is an isometric view of this preferred embodiment, while FIG. 5D is a plan view;

FIGS. 9A to 9E schematically show various preferred embodiments of fiber bundle applications, according to further preferred embodiments of the present invention;

FIG. 9A is a graphical illustration of the transmission and the coherence reduction factor of a single fiber optical bundle, such as that shown in the embodiment of FIG. 7, as a function of fiber optical length difference divided by the coherence length of the source;

FIG. 9B is a schematic illustration of a double bundle fiber optical illumination system, according to a preferred embodiment of the present invention;

FIGS. 9C and 9D respectively illustrate schematically two embodiments of a first bundle of a double bundle illumination system, such as that of FIG. 9B, according to another preferred embodiment of the present invention, in which the bundle is made up of groups of fibers of the same length;

FIG. 9E is a schematic drawing of the second bundle of fibers of the preferred embodiment of FIG. 9B, in which each of the fibers is of a different optical length, the optical lengths preferably differing by the coherence length of the light source or less;

FIG. 9F is a schematic illustration of an alternative and preferred apparatus for performing pulse stretching, according to another preferred embodiment of the present invention;

DETAILED DESCRIPTION OF PREFERRED EMBODIMENTS

The present invention provides a method and system for fast on-line electro-optical detection of wafer defects.

The method and system for fast on-line electro-optical detection of wafer defects of the present invention introduces the unique combination of a new imaging system featuring an optically formed surface of photo-detectors at the focal plane formed from an array of several two-dimensional matrix photo-detectors for acquiring a high resolution, high pixel density, large field of view image of a wafer die, synchronized with an illumination system featuring illumination of the wafer die by a short light pulse from a repetitively pulsed laser. The laser light pulse duration is significantly shorter than the image pixel dwell time, where the pixel dwell time refers to the time a point on the wafer is imaged by a detector pixel while the wafer is moving, and the laser light pulse rate is synchronized with the frame speed of the individual matrix photo-detectors.

Steps of operation of the method, and components of the system of the present invention are better understood with reference to the drawings and the accompanying description. It is to be noted that illustrations of the present invention shown here are for illustrative purposes only and are not meant to be limiting.

Figure 1A:
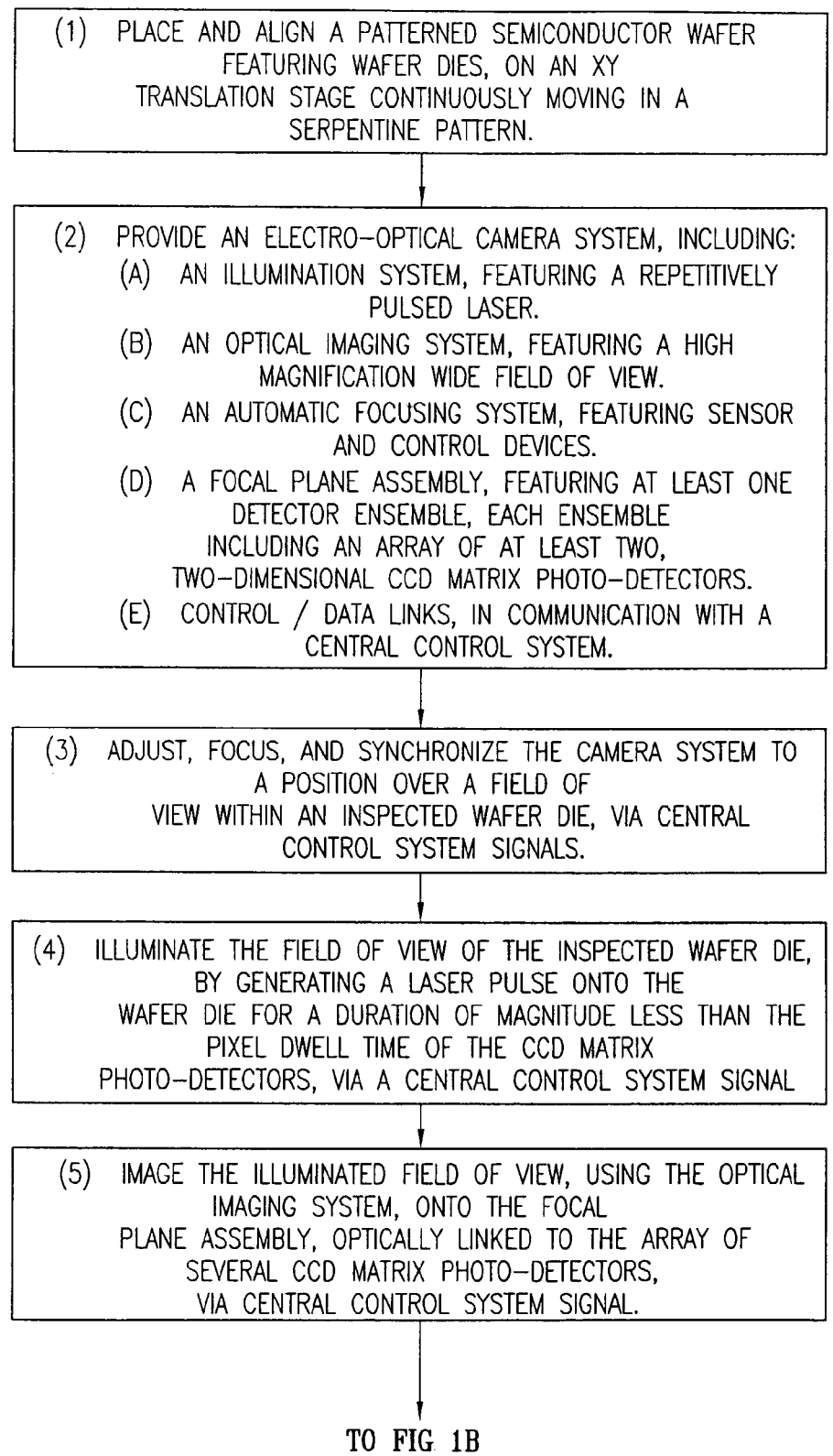

Referring now to the drawings, FIG. 1 is a flow diagram of a preferred embodiment of a method for fast electro-optical on-line detection of wafer defects. In FIG. 1, each generally applicable, principal step of the method of the present invention is numbered and enclosed inside a frame. Sub-steps representing further of an indicated principal step of the method are indicated by a letter in parentheses. FIGS. 2 through 6 are schematic diagrams illustrating exemplary preferred embodiments of the system, and of system components, for implementing the method for fast on-line electro-optical detection of wafer defects of the present invention. System components shown in FIGS. 2 through 6 corresponding to the method of FIG. 1 are referred to in the description of FIG. 1. Details and specific examples of system components of FIGS. 2 through 6 are provided throughout the following description. Terminology and references appearing in the following description of FIG. 1 are consistent with those shown in FIGS. 2-6.

In Step 1 of the method, a patterned semiconductor wafer 12 featuring a plurality of wafer dies 14, is placed and aligned on a continuous moving XY translation stage 16. This is shown in system 10 of FIG. 2, which is a schematic diagram illustrating an exemplary preferred embodiment of the system for fast on-line electro-optical detection of wafer defects. XY translation stage 16 moves wafer 12 typically in a serpentine pattern beneath an optical imaging system 18. Movement of XY translation stage 16, and therefore movement of wafer 12, are synchronized, by a central control system 20 via control/data links 22, with action of a multi-component camera system in a way that wafer 12 moves the equivalent of one field of view 24 during a CCD matrix photo-detector frame time of 33 milli-seconds and only a fraction, for example, on the order of about $10^{-2}$ of a single pixel during exposure to an illumination system 26, thereby resulting in no image smear or loss of image resolution.

In Step 2, a multi-component electro-optical camera system is provided, including (a) an illumination system 26, (b) an optical imaging system 18, (c) an automatic focusing system 28, (d) a focal plane assembly 30, and (e) respective system control/data links, in communication with central control system 20.

In sub-step (a) of Step 2, an illumination system 26 is provided, including a repetitively pulsed laser 32, a laser beam expander 34, a laser beam light path 36, and control/data links 38. This type of illumination system enables ultra fast imaging of a large field of view 24, by featuring pulsed laser 32 for repetitively generating and propagating a highly bright and highly energetic light pulse in an extremely short period of time.

This contributes to the overall method of wafer inspection having high throughput. Monochromatic laser illumination is also preferably used, in order to simplify design requirements of the wide field of view optical imaging system 18, since there are no chromatic aberrations requiring optical correction or adjustment. Illumination system 26 is in communication with the central control system 20 via control/data links 38.

In system 10, pulse rate, i.e., pulses per second, of pulsed laser 32 is synchronized with frame speed of the array of individual matrix photo-detectors of focal plane assembly 30. A laser pulse illuminating field of view 24 of a wafer die 14 for a time duration of nanoseconds compared to milliseconds frame time of temporally gated camera system focal plane assembly 30 of matrix photo-detectors, results in instantaneous illumination of field of view 24 of an inspected wafer die 14. In one very short laser pulse, a relatively large number of pixels, for example, about forty eight million pixels, of focal plane assembly array 30 of several, for example, twenty four, matrix photo-detectors, is simultaneously illuminated, and there is essentially no relative movement among the pixels. The laser light pulse duration is significantly shorter than the image pixel dwell time, where the pixel dwell time refers to the time a point on the wafer is imaged by a detector pixel while the wafer is moving.

Preferably, repetitively pulsed laser 32 is a Q switched Nd:YAG laser, optically pumped by light emitting diodes, at a pulse rate of 30 pulses per second, with a pulse time interval of about 10 nanoseconds, generating a pulsed monochromatic light beam at a wavelength of 1.06 microns. The pulse rate of pulsed laser illumination system 26 of 30 pulses per second, is synchronized with a frame speed of 30 frames per second, of the array of CCD matrix photo-detectors on focal plane assembly 30.

Optical resolution is a linear function of the illuminating wavelength. Resolution of an optical system increases as illumination wavelength decreases. Therefore, to increase resolution of optical system 18 and consequently defect detection sensitivity of inspection system 10, a crystal 40 having non linear optical properties and serving as a 'second harmonic' generating crystal 40 is placed in laser beam light path 36 of illumination system 26. Second harmonic generating crystal 40 causes halving of the wavelength of the laser light beam generated by pulsed laser 32, for example, from 1.06 microns to 0.53 micron, thereby, doubling resolution of wafer inspection system 10. Alternatively and preferably, the third harmonic at 0.266 micron can be used to provide even higher resolution.

In sub-step (b) of Step 2, an optical imaging system 18, is provided, including a focusing lens 42, a beam splitter 44, an objective lens 46, and control/data links 49. This system is suitable for ultra fast high resolution synchronous imaging of high magnification, for example, 50×, of wide field of view 24 of a wafer die 14. An automatic focusing system 28 automatically adjusts and sets the position of objective lens 46 of optical imaging system 18 for optimum focus of all wafer dies 14 on wafer 12. Optical imaging system 18 is in communication with the central control system 20 via control/data links 49. During operation of wafer inspection system 10, focusing lens 42 images laser light 48, where laser light 48 represents light reflected, scattered and diffracted by wafer 12, onto focal plane assembly 30. This imaging process is further described with reference to FIG. 5A below.

In sub-step (c) of Step 2, an automatic focusing system 28, including sensor and control devices (not shown) is provided, which, via optical imaging system 18, automatically maintains wafer 12, and therefore, a wafer die 14, in focus.

In sub-step (d) of Step 2, a focal plane assembly 30 is provided, including a number of detector ensembles 50 (FIGS. 4-5), where each detector ensemble 50 features several individual two-dimensional matrix photo-detectors, preferably but not limited to, at least two two-dimensional CCD matrix photo-detectors 52 (FIGS. 3A-3B), focal plane assembly electronics 54, and control/data links 56, 58, and 90, enabling high capacity and ultra fast high resolution synchronous imaging of a wafer die 14. Preferred structural and configurational components and features of focal plane assembly 30 are provided in FIGS. 3A and 3B, FIGS. 4A through 4D, and FIGS. 5A and 5B, which are schematic diagrams illustrating close-up views of an individual CCD matrix photo-detector 52, a detector ensemble 50 and focal plane assembly 30, respectively.

In FIGS. 3A-3B, of schematic diagrams illustrating top and side views of a two-dimensional CCD matrix photo-detector 52, respectively, photo-sensitive area 60 is surrounded by a photo-insensitive area 62, a configuration which prevents the physical placement of two CCD matrix photo-detectors side-by-side. Focal plane assembly 30 (FIGS. 2 and 5A) includes several, for example, six, detector ensembles 50 (FIGS. 4A and 4B), where each detector ensemble 50 includes several, for example, four, two-dimensional CCD matrix photo-detectors 52, for a total of, for example, twenty four, commercially available high resolution, black and white, silicon two-dimensional CCD matrix photo-detectors 52, wherein each CCD matrix photo-detector 52 has a very high number of, for example, 1940×1035 (i.e., on the order of two million or 2 mega) image sensing picture elements, or pixels, capable of providing 30 frames per second at high definition standards.

Figure 2:
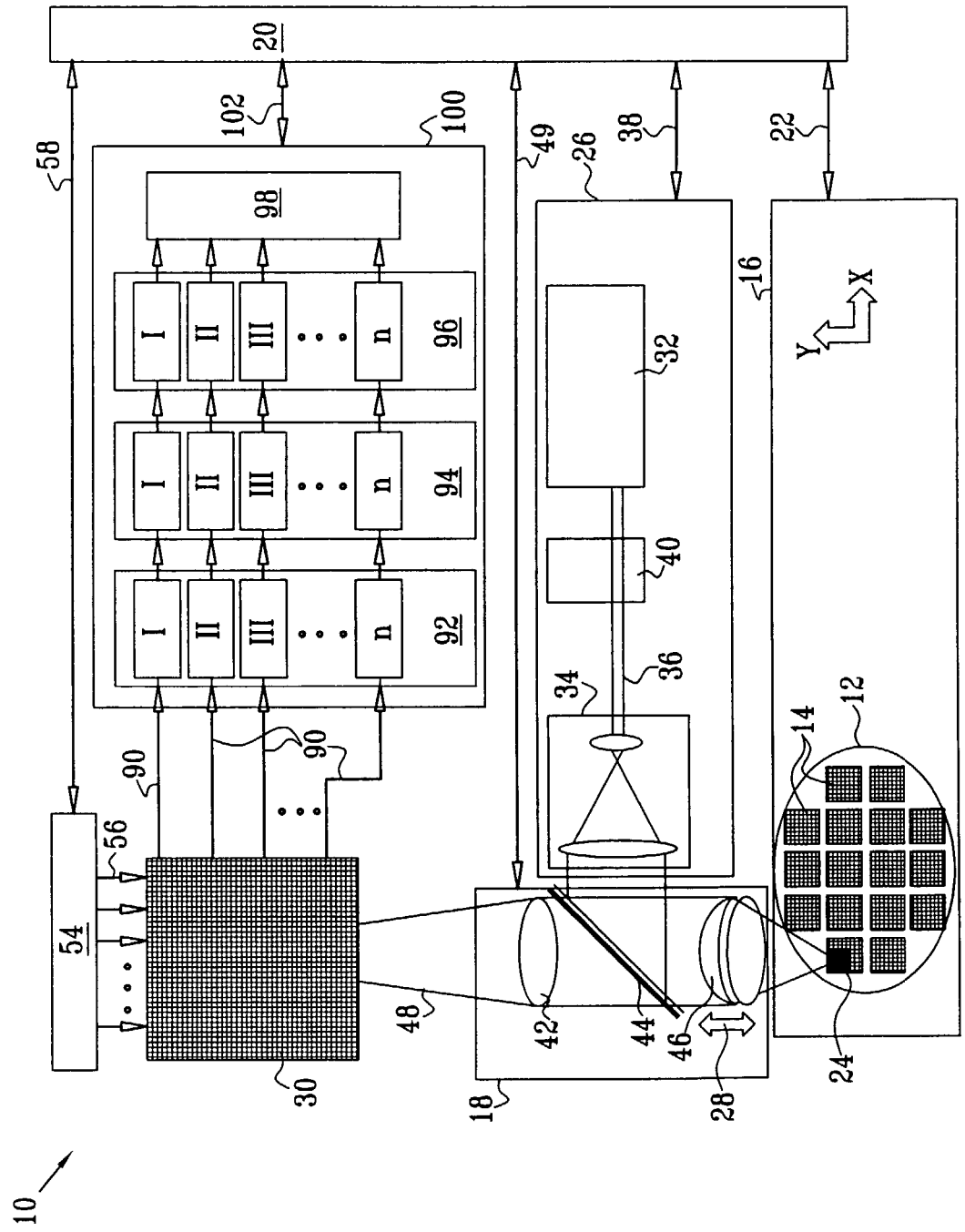
FIG. 2 is a schematic diagram illustrating an exemplary preferred embodiment of the system for fast on-line electro-optical detection of wafer defects, in accordance with the present invention.

Focal plane assembly 30, featuring six detector assemblies 50, each detector ensemble featuring an array 64 (FIG. 4D) of four individual CCD matrix photo-detectors 52, optically couples all twenty-four individual CCD matrix photo-detectors 52 to optically form a, preferably, but not limited to, continuous, surface of photo-detectors 66 at the focal plane (FIG. 5B), filling the relatively large field of view 24 of the 50× magnification microscopy optical imaging system 18. This optical configuration enables illumination of a wafer die 14 with a single laser pulse and simultaneous imaging by an array 66, of twenty-four two-dimensional CCD matrix photo-detectors, having a total of about 48 million (48 mega) pixels. For a CCD matrix photo-detector frame speed of 30 frames per second, and an array of about 48 megapixels, image acquisition of wafer die 14 is at a rate of about 1.5 billion (1.5 giga) pixels per second. Such an image acquisition rate translates to very high system throughput. Focal plane assembly 30 is in communication with central control system 20 via control/data links 56 and 58 (FIG. 2).

FIGS. 4A and 4B are schematic diagrams illustrating close-up side views of detector ensemble 50, showing geometric configuration of two sets of, for example two CCD matrix photo-detectors each 52A and 52B. Preferably, each detector ensemble 50 is constructed from two glass prisms 68 and 70, each prism having a right angle and a 45 degrees diagonal surface. Diagonal surface 72 of prism 68 has zones on which a highly reflective coating, preferably approaching 100%, are applied. On each prism 68 and 70 at least one CCD matrix photo detector is optically bonded. Exemplary set of two CCD matrix photo-detectors 52A bonded on prism 68 is identical to exemplary set of two CCD matrix photo-detectors 52B bonded on prism 70. In FIG. 4B, the set of two CCD matrix photo-detectors 52A are shown bonded in straight file on prism 68, and the set of two CCD matrix photo-detectors 52B are bonded in straight file on prism 70, and the exact position of the bonded CCD matrix photo-detectors is selected such that all photo-sensitive areas 60 of individual CCD matrix photo-detectors 52A and 52B optically appear as one continuous straight strip when viewed from View A.

FIG. 4C is a schematic diagram illustrating a close-up view of diagonal surface 72, of glass prism 68, including zones of highly reflective coating. FIG. 4C shows a view of Section B-B of FIG. 4A, wherein zones 74, on diagonal surface 72, are coated with highly reflective coating, and are arranged on surface 72 to be opposite photo-sensitive areas 60 of CCD matrix photo detectors 52A bonded on prism 68. Light entering detector ensemble 50 along View A, opposite reflective zones 74, are reflected by reflective zones 74 and deviated by 90 degrees to impinge upon CCD matrix photo-detectors 52A. Light entering detector ensemble 50 along View A, not opposite reflective zones 74 pass through prisms 68 and 70 undeviated and impinge upon CCD matrix photo-detectors 52B.

FIG. 4D is a schematic diagram illustrating a close-up front optical view, of detector ensemble 50 shown in FIGS. 4A-4C, showing the appearance of an optically continuous surface of photo-detectors, featuring the plurality of CCD matrix photo detectors 52. FIG. 4D shows View A of FIG. 4B and demonstrates the creation by optical means of continuous surface 64, featuring four photo-sensitive photo-detector areas 60. Within surface 64, those photo-sensitive areas 60 opposite reflecting zones 74 are associated with CCD matrix photo-detectors 52A bonded onto prism 68. The other photo-sensitive areas 60 not opposite reflecting, zones 74 are associated with CCD matrix photo-detectors 52B, bonded onto prism 70. Photo-detectors 52A and 52B are in different surfaces or planes and photosensitive areas 60 are not continuous, but detector ensemble 50 creates surface 64 by optical means.

FIG. 5A is a schematic diagram illustrating a close-up view of focal plane assembly 30, including beam splitting prisms 76 and 78, and detector ensembles 50. In FIG. 5A, focal plane assembly 30 includes six detector ensembles 50, two labeled 50A, two labeled 50B, and two labeled 50C. Light 48, representing reflected, scattered, and diffracted laser illumination light coming off of wafer 12, is directed and focused into focal plane assembly 30 by focusing lens 42. Light 48 passes through beam splitting glass cube 76 which reflects, at 90 degrees, approximately 33% of light 48, forming imaging channel 80, and transmits about 67% of light 82. Transmitted light 82 emerging from beam splitting cube 76, goes through a second beam splitting cube 78 which reflects, at 90 degrees, approximately 50% of light 82, forming imaging channel 84, and transmits about 50% of light 82, forming imaging channel 86.

This configuration of the combination of beam splitting cubes 76 and 78 creates three imaging channels 80, 86 and 84, each with equal light energy, and each with approximately 33% of the light energy of original input light beam 48. Optical cube 88 is inserted in imaging channel 80 so as to equalize the amount of glass in the optical paths of all three imaging channels, thus enabling similar image quality formed in all three channels. At the focus point of focusing lens 42, for each of the three imaging channels 80, 86, and 84, two sets of detector ensembles 50 are placed. One set of two detector ensembles 50A is placed in imaging channel 80, one set of two detector ensembles 50B is placed in imaging channel 86, and one set of two detector ensembles 50C is placed in imaging channel 84.

FIG. 5B is a schematic diagram illustrating front optical View A of focal plane assembly 30 demonstrating optical formation of continuous surface 66 of photo-detectors at the focal plane, by using six detector ensembles 50 and twenty-four two-dimensional CCD matrix photo-detectors 52 located in different geometrical surfaces.

Figure 5C:
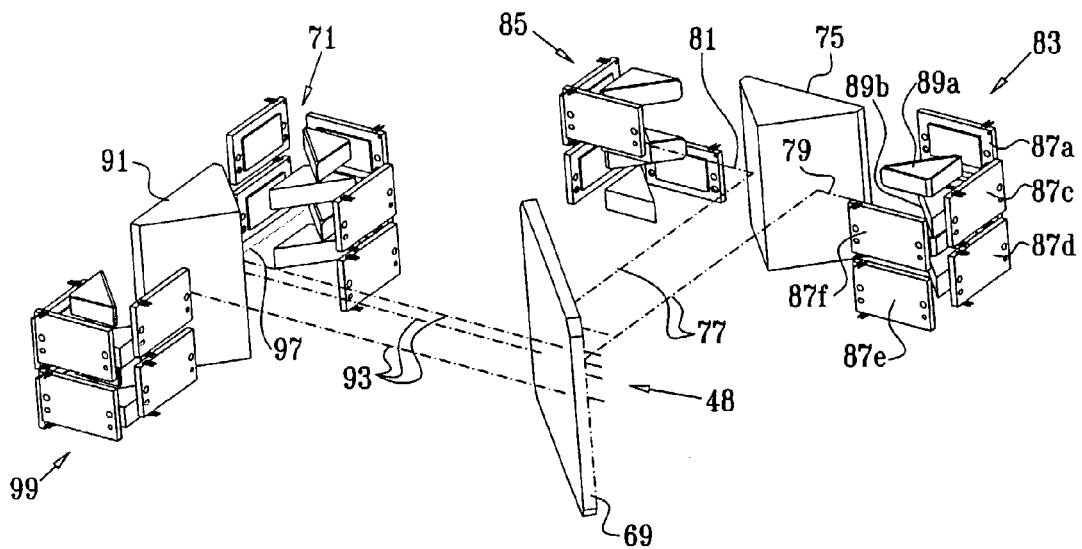
FIGS. 5C and 5D are schematic drawings of an alternative and preferred embodiment of a focal plane array of detectors, differently arranged to that shown in FIG. 5A.
Figure 5D:
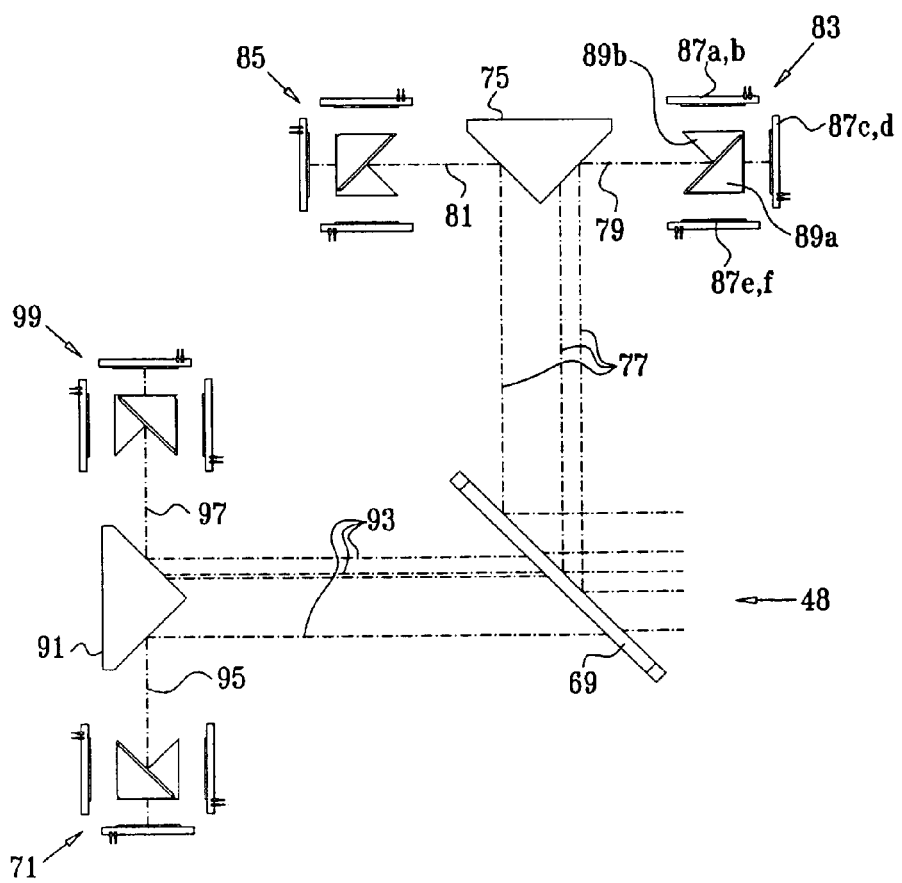

Reference is now made to FIGS. 5C and 5D, which are schematic drawings of an alternative and preferred embodiment of a focal plane array 30 of detectors, differently arranged to that shown in FIG. 5A. FIG. 5C is an isometric view of this preferred embodiment, while FIG. 5D is a plan view. In FIGS. 5C and 5D, in order to make tracking of the optical path of the beam in each imaging channel clearer, the beams impinging on each separate detector are shown only by their axial ray position. Thus, the incoming image beam 48 appears as a number of lines representing axial rays arriving ultimately at each detector.

The incoming beam 48, containing an image of the field of view of the section of the wafer under inspection, impinges on a 50% beam splitter 69, from which, half of the incoming beam is reflected towards prism 75, which is aligned with its apex towards those incident parts of the image beam 77, such that it further splits those parts into separate beams 79, 81. Each of the further subdivided beam sections 79, 81 are directed towards detector ensembles, in the form of detector towers 83, 85. In detector tower 85, taken as an example of all of the detector towers of this embodiment, there are 6 separate detectors 87*a* to 87*f* (87*b* is hidden in FIG. 5C), preferably two-dimensional CCD matrix photo detectors, as previously described. Light coming from prism 75 is directed into one or other of these detectors 87*a* to 87*f,* preferably by reflection from the faces of four tower prisms 89*a* to 89*d,* of which only the top two, 89*a* and 89*b* are shown for clarity in FIG. 5C. These four tower prisms direct selected parts of the incoming beam 79 onto the detectors in the tower located on either side of the optical axis of beam 79, according to their height up the tower. Those detectors located directly in the path of beam 79 receive their sections of the incident beam without reflection from a tower prism. Thus, tower prism 89*a* directs the uppermost part of the beam 79 onto detector 87*a,* tower prism 89*b* directs a lower part of the beam 79 onto detector 87*f,* while detector 87*c* receives its beam directly without reflection after passage through the gap between tower prisms 87*a,* and 87*b.* In a similar manner, detector tower 85 splits up incident beam section 81 for incidence onto the six detectors in detector tower 85. For clarity, only 4 of these detectors are shown in detector tower 85.

In this manner, the whole of the incident image beam 77 can be divided up for detection on the 12 detectors of the preferred arrangement in detector towers 83 and 85 shown in FIGS. 5C and 5D. There are several different methods of ensuring that the photo-sensitive areas of each of the detectors are optically arranged such that a continuous surface of photo-detectors is obtained in the focal plane, as preferably shown in FIG. 5B. According to a first preferred method, each tower is self-contained and the detectors are vertically offset such that full vertical photo-sensitive coverage is achieved within the detectors of that tower. According to a second preferred embodiment, both detector towers 83 and 85 are interactively arranged so that the detectors of both towers together are vertically arranged that they achieve complete photo-sensitive coverage of the whole of incident beam section 77.

Referring back now to the other 50% of the incident beam 48 which is transmitted through beam splitter 69, it is directed towards prism 91, which is aligned with its apex towards those incident parts of the image beam 93, such that they are further split into separate beams 95, 97. Each of these further subdivided beams sections are directed towards detector ensembles, in the form of detector towers 71, 99, whose component detectors are arranged as a focal plane array, operative in a manner similar to that described in connection with detector towers 83 and 85.

According to the embodiment shown in FIGS. 5C and 5D, the image beam 48 is divided by the beam splitter 69, and the separate divided parts are directed towards detector towers 83 and 85 and towards detector towers 71 and 99, where they are further sub-divided by the arrangement of the separate detectors in each of the detector towers, as described above. The spatial disposition of the detectors and beam splitter strips are preferably arranged such that the entire input image beam area is covered by an optically continuous surface of photosensitive detector areas, such as is preferably shown in FIG. 5B. It is to be understood, however, that the above-described preferred geometric sectioning of the input image beam is not the only method of achieving continuous coverage of the imaged area of the wafer with photo-sensitive detector areas, but that according to further preferred embodiments of the present invention, different geometric division of the image beam may be equally well performed.

In (e) of Step 2, referring again to FIG. 2, control/data links, including 38, 49, 54, 56, and 58, and central control system 20, feature electronic interconnections among the different systems and system components, enabling proper automation and synchronization of the various steps of the method of detection of wafer defects. For example, automatic movement of wafer 12 via movement of XY translation stage 16 is electronically set at a linear speed such that wafer 12 moves a distance of one field of view 24 between the time of two pulses emitted by pulsed laser 32 in illumination system 26. Temporally gated opening and closing, or frame speed, of focal plane assembly 30, including all CCD matrix photo-detectors 52 is synchronized with the pulse rate of pulsed laser 32 in illumination system 26.

In Step 3, the camera system of Step 2 is adjusted, focused, and set to a position over an inspected field of view 24 within a wafer die 14, via central control system 20 signals. Pulse rate of pulsed laser 32 in illumination system 26 is synchronized with the frame speed of CCD matrix photo-detectors 52 included in detector ensembles 50A, 50B, and 50C of focal plane assembly 30. This step is performed in order to enable movement of wafer 12, and therefore, of an inspected wafer die 14, at a speed such that an inspected field of view 24 is covered during the time interval of one frame of CCD matrix photo-detectors 52 of focal plane assembly 30.

In Step 4, instantaneous illumination of an inspected field of view 24 of an inspected wafer die 14 of Step 3 is achieved by generating a laser pulse onto inspected wafer die 14, for a time duration, for example, ten nanoseconds, orders of magnitude less than synchronized pulse rate and frame time of camera system CCD matrix photo-detectors 52, via a central control system 20 signal. In a ten nanosecond laser pulse, about 48 million pixels, of focal plane assembly 30 featuring twenty-four CCD matrix photo-detectors 52, is simultaneously illuminated, and there is no relative movement among the pixels. During the short laser pulse, there is effectively no wafer motion during the wafer exposure time, since the laser pulse duration is much shorter than the pixel dwell time, which is the time a point on the wafer is imaged by a detector pixel while the wafer moves, and therefore, there is effectively no image smear degrading image resolution, as is typically the case in wafer inspection methods and systems featuring continuous illumination of a wafer.

In Step 5, illuminated inspected field of view 24 of Step 4 is imaged by optical imaging system 18 onto focal plane assembly 30, optically linked to detector ensembles 50A, 50B, and 50C, featuring the twenty-four, two dimensional CCD matrix photo-detectors 52, via central control system 20 signal.

In Step 6, the digital image (not shown) of Step 5, featuring about 48 million pixels, of an inspected field of view 24 of a wafer die 14 is acquired by using focal plane assembly 30 optically forming a, preferably, but not limited to, continuous surface of at least two two-dimensional CCD matrix photo-detectors 52, by synchronized opening of temporally gated CCD matrix photo-detectors 52, via a central control system 20 signal. During the frame time interval of each activated CCD matrix photo-detector 52, wafer 12, and therefore, wafer die 14, moves via XY translation stage 16 the equivalent of one field of view. This corresponds to a large pixel dwell time relative to laser pulse time interval, resulting in the wafer moving only a fraction, for example, on the order of $10^{-2}$, of a single pixel during exposure to array 66 (FIG. 5B) of CCD matrix photo-detectors 52 of focal plane assembly 30, thereby preventing image smear or loss of image resolution. In sub-step (a), acquired digital image data is grabbed via a set of parallel configured image processing channels 90 by an image grabber 92, and is saved in an image memory buffer 94, part of image processing system 100 (FIG. 2).

Figure 6:
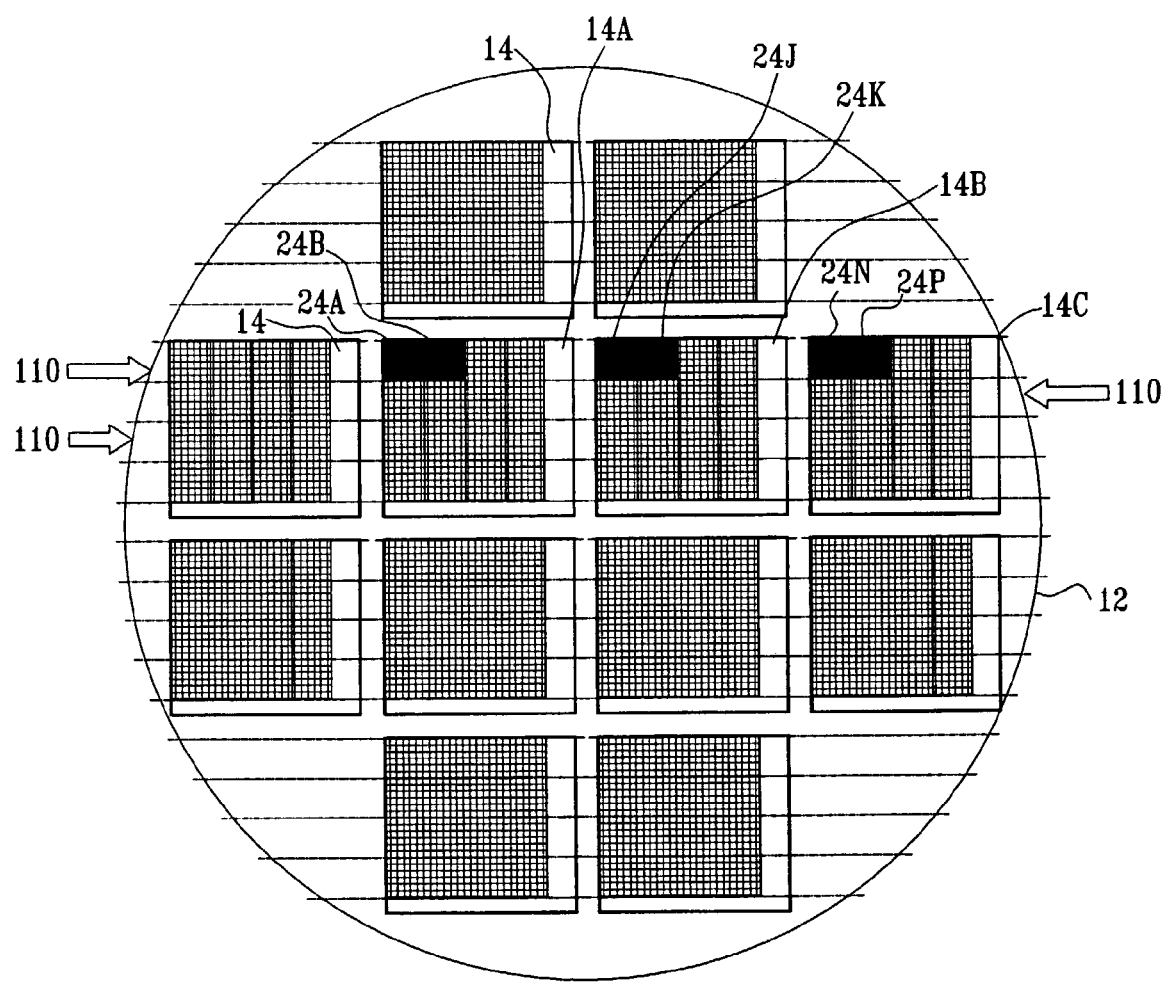
FIG. 6 is a schematic diagram illustrating a close-up view of the image acquisition process featuring wafer dies, where each wafers die is sequentially inspected by imaging a plurality or strips of fields of view, one field of view at a time, in accordance with the present invention.

In Step 7, Step 3 through Step 6 are sequentially repeated for image acquisition of the next fields of view within the same inspected wafer die 14, thereby forming a strip of fields of views until and including the first equivalent field of view of the nearest neighboring wafer die in the strip, serving as a reference. This automated sequential imaging process is clearly illustrated in FIG. 6, which is a schematic diagram illustrating a close-up view of the image acquisition process featuring wafer dies, where each wafer die is sequentially inspected by imaging a plurality or strips of fields of view, one field of view at a time. In FIG. 6, following image acquisition of first field of view 24A in first inspected wafer die 6A, there is image acquisition of second field of view 24B in same first inspected wafer die 14A. Synchronized with serpentine motion of wafer 12, image acquisition of successive fields of view, one after another, progresses throughout entire first inspected wafer die 14A, and continues until an image is acquired for first field of view 24J in second inspected wafer die 14B. This process results in the formation of continuous strips 110 of imaged wafer dies 14, until eventually entire wafer 12 is completely imaged.

In Step 8, digital image data of each field of view in an inspected wafer die and, of each equivalently located field of view in the nearest neighboring wafer die, serving as a reference, are processed, by using an image processing system. Referring to FIG. 2, image processing system 100 includes parallel configured image processing channels 90 for image grabbing by an image grabber 92, an image buffer 94, a defect detection unit 96, a defect file 98, and control/data links 102. Image data acquired by focal plane assembly 30 featuring twenty-four two-dimensional CCD matrix photo-detectors 52 is processed in parallel, whereby each of the twenty-four CCD matrix photo-detectors 52 communicates separately, in parallel to the other CCD matrix photo-detectors 52 of focal plane assembly 30, with image grabber 92, via twenty-four separate image processing channels 90. Instead of processing image data using a single serial channel of 48 megapixels at a CCD frame speed acquisition rate of 30 times per second, resulting in a single channel with a very high, 1.5 gigapixels per second processing rate, each of the twenty-four separate image processing channels 90 having about 2 megapixels of image data, acquired at a rate of 30 times per second, is used for processing at a moderate rate of 60 megapixels per second. In this configuration, an overall image processing rate of 1.5 gigapixels per second is achieved using significantly slower individual channels, which are easier to implement in wafer defect detection system 10 using commercially available hardware. This feature of parallel processing of acquired image data contributes significantly to the resulting high throughput of the method of wafer inspection of the present invention. Image processing system 100 is in communication with central control system 20 via control/data links 102.

Step 8 includes sub-step (a) performing an image alignment between the inspected field of view and the reference field of view, sub-step (b) identifying the presence of a potential wafer defect, sub-step (c) saving the comparison data in a defect file, and sub-step (d) deleting unneeded image data of the first field of view of the first inspected wafer die.

In sub-step (a) of Step 8, an image alignment is performed between the image of each inspected field of view and the corresponding field of view serving as a reference, prior to identifying the presence of a potential wafer defect in the inspected wafer die. Due to minor mechanical inaccuracies during movement of XY translation stage 16, velocity of a wafer 12 beneath camera optical imaging system 18 is not constant. As a result of this, image pixel positions in the multiple fields of the CCD matrix detectors may not be as initially programmed according to inter-system synchronization. Therefore, a two-dimensional translational image alignment correction between an inspected field of view and a reference field of view is performed. More complex rotation registration correction may also be performed, but for standard implementation of the method and system of the present invention, it is neglected. This process of aligning images of fields of views, prior to defect detection by image comparison is illustrated in FIG. 6 for exemplary strips 110 of equivalent fields of view. Pixel positions in the image of first field of view 24A of first inspected wafer die 14A and pixel positions in the image of equivalently located first field of view 24J of nearest neighboring wafer die 14B are extracted from image buffer 94, and are subjected to an image alignment correction. In this process, first field of view 24J of nearest neighboring wafer die 14B serves as the reference to equivalent field of view 24A of first inspected wafer die 14A.

Prior alt methods and systems of wafer defect detection, such as those described above, featuring a combination of continuous wafer illumination and acquiring a two dimensional image by either scanning a wafer in one or two dimensions require a registration correction for all pixels or all pixel lines. This limits overall system speed, i.e., throughput, and increases requirements of electronic hardware and overall system costs. Moreover, this results in residual misregistration, since no correction procedure is accurate for all pixels in an image. Residual misregistration significantly reduces system defect detection sensitivity. In contrast, for the preferred embodiments of the method and system of the present invention, all focal plane assembly CCD matrix detector pixels in any given field of view of the focal plane assembly are considered one unit, and are (generated simultaneously by a single laser pulse. Therefore, there is no need for pixel registration within a focal plane assembly field of view, and a simple alignment correction between any small localized zone within the inspected field of view and the equivalent zone in a reference field of view is correct over the entire focal plane assembly field of views. Therefore, in the present invention, residual misregistration is negligible, enabling improved defect detection sensitivity.

In sub-step (b) of Step 8, following image alignment correction, there is identification of the presence of a potential wafer defect in the inspected wafer die, by comparing differences of pixel intensities of the image of each, starting from the first field of view of the inspected wafer die to pixel intensities of the image of each equivalently located, starting from the first, field of view of the nearest neighboring wafer die. In this defect identification step, a standard algorithm of defect detection is used, which is based on the analysis of comparing pixel intensities of images acquired from identical fields of view of adjacent neighboring wafer dies, featuring a like pattern. Defect detection is based on a statistical approach, whereby the probability that a defect will exist at the equivalent location within adjacent wafer dies is very low. An exemplary standard algorithm for locating irregularities among pixel intensities of different images is based on a three-die comparison. The overall wafer inspection system is programmed to inspect the pattern, pixel-by-pixel, of a wafer die or field of view, typically referred to as the inspected pattern, and then compares it to the supposedly equivalent pattern of the adjacent neighboring wafer die on the same wafer, which serves as a reference. A defect detector detects any pattern irregularity or difference which would indicate the possible presence of a wafer defect in the current inspected wafer die. The pattern under test is also compared with the equivalently located pattern of another adjacent wafer die in order to resolve ambiguity that may exist if the test pattern was compared with only a single pattern. In the second comparison, in order to maintain symmetry, the pattern under test serves as the reference.

This image comparison process, performed by defect detection unit 96 (FIG. 2) is illustrated in FIG. 6. Each pixel intensity in the image of first field of view 24A of first inspected wafer die 14A is compared to the pixel intensity in the image of equivalently located first field of view 24J of adjacent neighboring wafer die 14B.

In sub-step (c), according to pre-determined comparison criteria, such as a specified difference or irregularity threshold level, a difference or irregularity in intensity of the two corresponding pixels in equivalently located first fields of view 24A, and 24J, of wafer dies 14A, and 14B acting as a reference, respectively, is saved in wafer defect file 98, in order to be further processed by a decision step confirming or dismissing defect existence and location (Step 10). In sub-step (d), unneeded image data of first field of view 24A of first inspected wafer die 14A is deleted from image buffer 94. As data of the comparison of equivalently located first fields of view 24A and 24J of first inspected and second inspected wafer dies 14A and 14B respectively, is saved, image data of first field of view 24A of first inspected wafer die 14A is no longer needed for image processing of successive wafer dies 14 in wafer 12.

In Step 9, Step 7 and Step 8 are repeated for sequential fields of view in second inspected wafer die 14B, until and including processing the image of first field of view 24N of third inspected wafer die 14C. Steps 7 and 8 are carried out in parallel. While image acquisition in Step 7 is carried out for each field of view in a strip 10, image processing and comparison of each preceding field of view in a strip 10 is carried out according to Step 8.

Step 10 is a decision and confirmation step, performed by defect detector unit 96, deciding and confirming whether or not there is detection of a wafer defect in each field of view, starting with field of view 24J of wafer die 14B, initially processed according to Step 8. Presence of irregularity or difference between equivalently located first fields of view 24A and 24J of first and second wafer dies 14A and 14B respectively, is followed by the next comparison between equivalently located first fields of view 24J and 24N of second and third wafer dies 14B and 14C, respectively, in order to confirm or dismiss the presence of a defect located in field of view 24J of wafer die 14B.

In sub-step (a) of Step 10, confirmed wafer defect information, including location of the confirmed wafer defect, is appropriately saved in defect file 98 for possible use in feedback control of a wafer fabrication process.

In Step 11, Step 7 through Step 10 are repeated, sequentially, for inspection of each field of view in a field of view strip 110 within the same wafer. In FIG. 6, for example, wafer field of view 24K in wafer die 14B becomes the next inspected field of view to be subjected to image processing by Step 7 through Step 10. Starting with field of view 24K in wafer die 14B, images of successive fields of view in second wafer die 14B are to be compared to equivalently located images of fields of view in wafer dies 14A and 14C. Field of view 24K in wafer die 14B is compared to equivalently located field of view 24B in wafer die 14A, with field of view 24B serving as the reference, and field of view 24K in wafer die 14B is compared to field of view 24P in wafer die 14C, with field of view 24K serving as a reference. In this case, each image of each successive set of fields of view in a strip 110 is compared once to an equivalent field of view on a wafer die proceeding it in the strip and once compared to an equivalent field of view on a wafer die succeeding it in the strip. Each compared field of view serves once as a reference field of view in the comparison and once as an inspected field of view in the comparison. Synchronized with serpentine motion of wafer 12, selection, illumination, imaging, acquisition, and processing, of an image of successive fields of view of successive wafer dies, one after another, progresses from wafer die to wafer die throughout entire wafer 12, until all wafer dies 14 of wafer 12 are inspected for defects.

Figure 7:
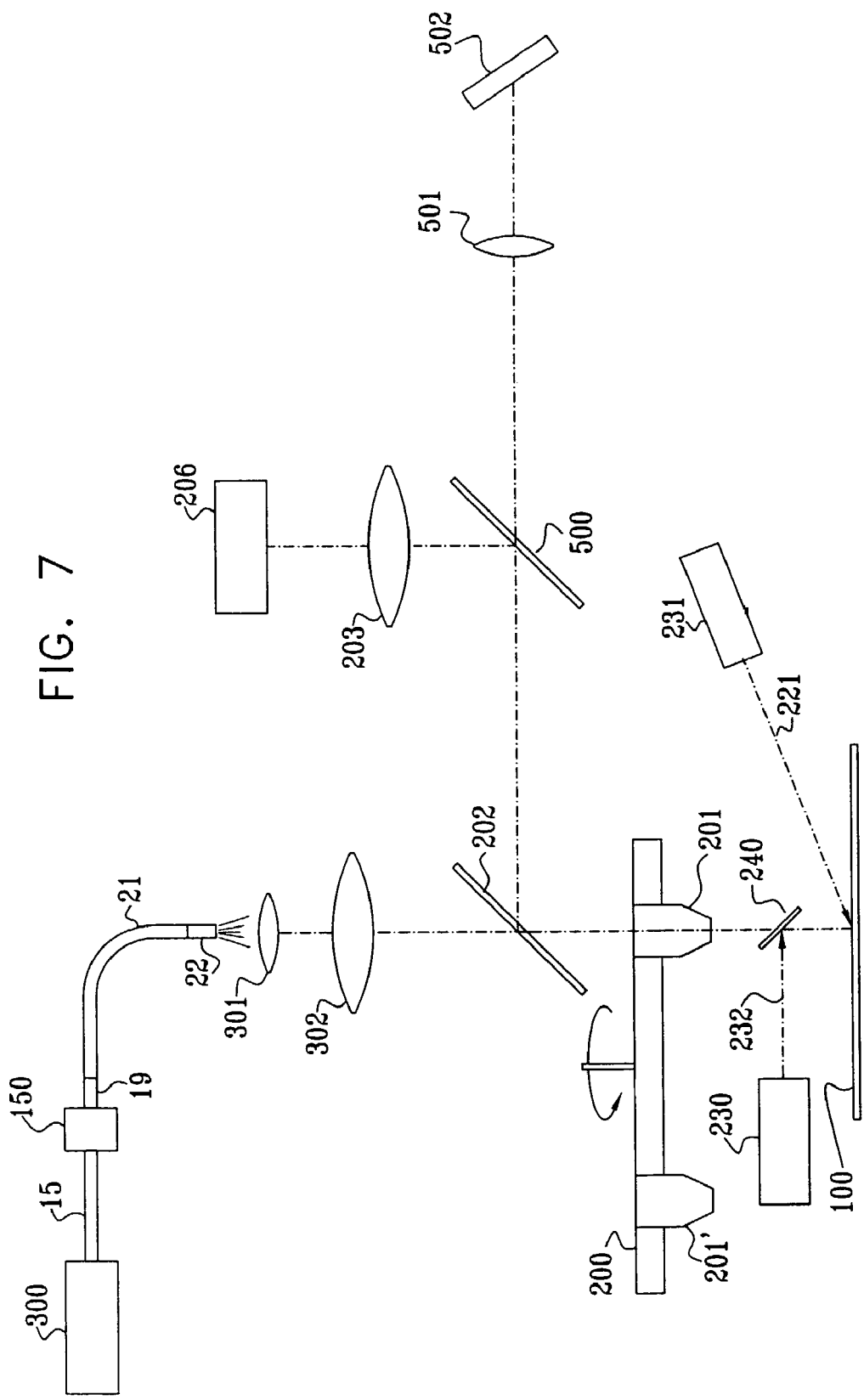
FIG. 7 is a schematic illustration of an object inspection system, utilizing a laser source and a fiber optical delivery bundle, constructed and operative according to a preferred embodiment of the present invention.

Reference is now made to FIG. 7, which is an overall schematic side view of the complete illumination system of the defect detection apparatus, according to one preferred embodiment of the present invention. According to different preferred methods of operation, three alternative modes of illumination are provided: Bright Field (BF), Side-illuminated Dark Field (DF) and Orthogonal or Obscured Reflectance Dark Field (ODF). Each mode of illumination is used to detect different types of defects in different production process steps. For example in order to detect an embedded defect in a transparent layer, such as silicon oxide, BF illumination is preferred. In order to detect a small particle on a surface, DF illumination generally yields better results.

In bright field illumination in general, the illumination is incident on the sample through the same objective lens as is used for viewing the sample. Reference is now made to FIG. 7, which shows a bright field illuminating laser source 300 delivering its output beam 15 into an optical delivery fiber bundle 21, preferably by means of a laser to fiber coupler 150. This optical fiber bundle 21 is required for the dual purposes of providing uniform illumination on the sample and for coherence breaking of the laser illumination, as will be expounded further hereinbelow. In the preferred embodiment of FIG. 7, only a single fiber bundle is used, but it is to be understood that a serial fiber bundle solution, as will be shown hereinbelow, could just as readily have been used. From the output termination of the fiber bundle 21, the laser beam is imaged by means of illumination transfer lenses 301, 302, whose detailed function will be explained hereinbelow in connection with FIGS. 10 to 13, onto the objective lens in use 201, which is operative to focus the illumination onto a wafer plane 100 being inspected. Appropriate alternative objective lenses 201' can be swung into place on an objective revolver 200, as is known in the microscope arts. The illumination returned from the wafer is collected by the same objective lens 201, and is deflected from the illumination path by means of a beam splitter 202, towards a second beam splitter 500, from where it is reflected through the imaging lens 203, which images the light from the wafer onto the detector 206. The second beam splitter 500 is used to separate the light going to the imaging functionality from the light used in the auto-focus functionality, which is directed by means of the auto-focus imaging lens 501 to the auto-focus detector 502.

When conventional dark field illumination is required for the imaging in hand, a dark field side illumination source 231 is used to project the required illumination beam 221 onto the wafer 100. When orthogonal dark field, or obscured reflectance dark field illumination is required for the imaging in hand, an alternative dark field illumination source 230 is used to project the required illumination beam 232 via the obscured reflectance mirror 240 onto the wafer 100 orthogonally from above. Fuller descriptions of all of these functionalities are given hereinbelow.

As described hereinabove, a repetitively pulsed laser source is preferably used in the illumination system of the present invention, though according to other preferred embodiments, CW laser illumination may also be used. In accordance with the requirements of providing a high brightness light source that produces a directionally intense beam of short time duration and at high repetition rates the third harmonic of a Nd:YAG Laser output is preferably used. The reason for the use of the third harmonic will be further expounded hereinbelow, in relation to the embodiment shown in FIG. 19.

The nature of a laser beam, and especially its coherent nature, presents a number of problems when used as an illuminating source in applications requiring a uniform illuminating flux over the inspected area, such as is required, for instance, in a wafer inspection system:

(i) Interference of light in the illumination optics creates non-uniformity in the illumination field.
(ii) Interference of the illuminated light by the structured pattern on the wafer creates artifacts in the image.
(iii) Surface roughness creates speckle, that generates non-uniformity in the image.
(iv) The laser beam itself is generally not uniform. Using the laser beam directly as a light source creates non-uniform illumination.

In order to overcome items (i) to (iii) above, the effects of the coherent nature of the laser beam must be reduced and preferably eliminated completely. This process is known as coherence breaking.

Speckle effects with CW lasers is comparatively easy to overcome, since it is possible to average the signal while varying the wave front. Several methods are described in the prior art for achieving this. When, however, the imaging process utilizes a single pulse for each acquired image, such a method becomes impossible to implement. According to further preferred embodiments of the present invention, there are provided methods whereby the coherence effect of the laser beam is reduced by splitting the laser beam into many beamlets and retarding each beamlet relative to the previous one in such a way that there is no definitive phase difference between them. The laser beam is thus divided into many pales, each part having no defined phase coherence with the other parts.

This requirement is insufficient, however, since it is also required that each point in the field of view (FOV) on the sample is illuminated by all parts of the laser beam. Each part of the beam is coherent or partially coherent with itself and thus may contribute to the generation of speckle, or to other interference effects that create high contrast artifacts in the image. Since each part of the beam is not coherent with the other parts of the beam, by ensuring that the FOV is illuminated by all parts of the laser beam, the total effect is averaged. The residual coherence effect depends on the number of beamlets used. Since each beamlet is independent of the others, the interference effect is reduced by the square root of the number of beamlets, assuming that all beamlets have the same intensity contribution. Consequently, the greater the number of beamlets, the lower the level of appearance of coherence artifacts in the image.

According to preferred methods of implementation of this technique, the laser beam is introduced into a fiber optics bundle, such as the fiber bundle 21 shown schematically in FIG. 7. The fibers in the bundle differ in length from each other by distances of the order of the laser coherence length in the fiber medium, or less. The number of fibers in the bundle dictates the contrast of the residual coherence effect in the image. The fiber bundle should preferably be illuminated uniformly. Each fiber in the bundle must carry more or less the same energy; otherwise averaging of the coherence effect will not be efficiently performed. Since the laser beam itself is not uniform and contains high and low spatial frequency components, the laser beam must be spatially mixed before introduction into the fiber. Additionally, the full numerical aperture of the fiber should preferably be filled, since at the far end of the bundle, uniform angular distribution of intensity is required. These latter two requirements do not appear to be fulfilled in the prior art. In the above-referenced article by Dingel et al., although it is stated that Koehler illumination is generated, no arrangement is shown for spatially mixing the laser beam, nor is there described a specific method for ensuring that the incident light is directed such that the Numerical Aperture of each fiber is fully illuminated. Under the conditions shown, each fiber would illuminate randomly, resulting in non-uniform field stop plane intensity, which then would also result in non-uniform illumination at the object plane. Furthermore, in the Dingle et al prior art, it is stated that the proposed array is made of N fiber-guides in which the length difference of any two fibers is greater than the coherence length of the light source. Such an arrangement would generally result in excessive differences, since it is the optical length difference and not the absolute length difference of any two fibers which needs to be greater than the coherence length of the light, according to the criteria chosen in the Dingel et al. article. Finally, the illumination system described in this prior art is for a transmissive imaging system.

Figure 8:
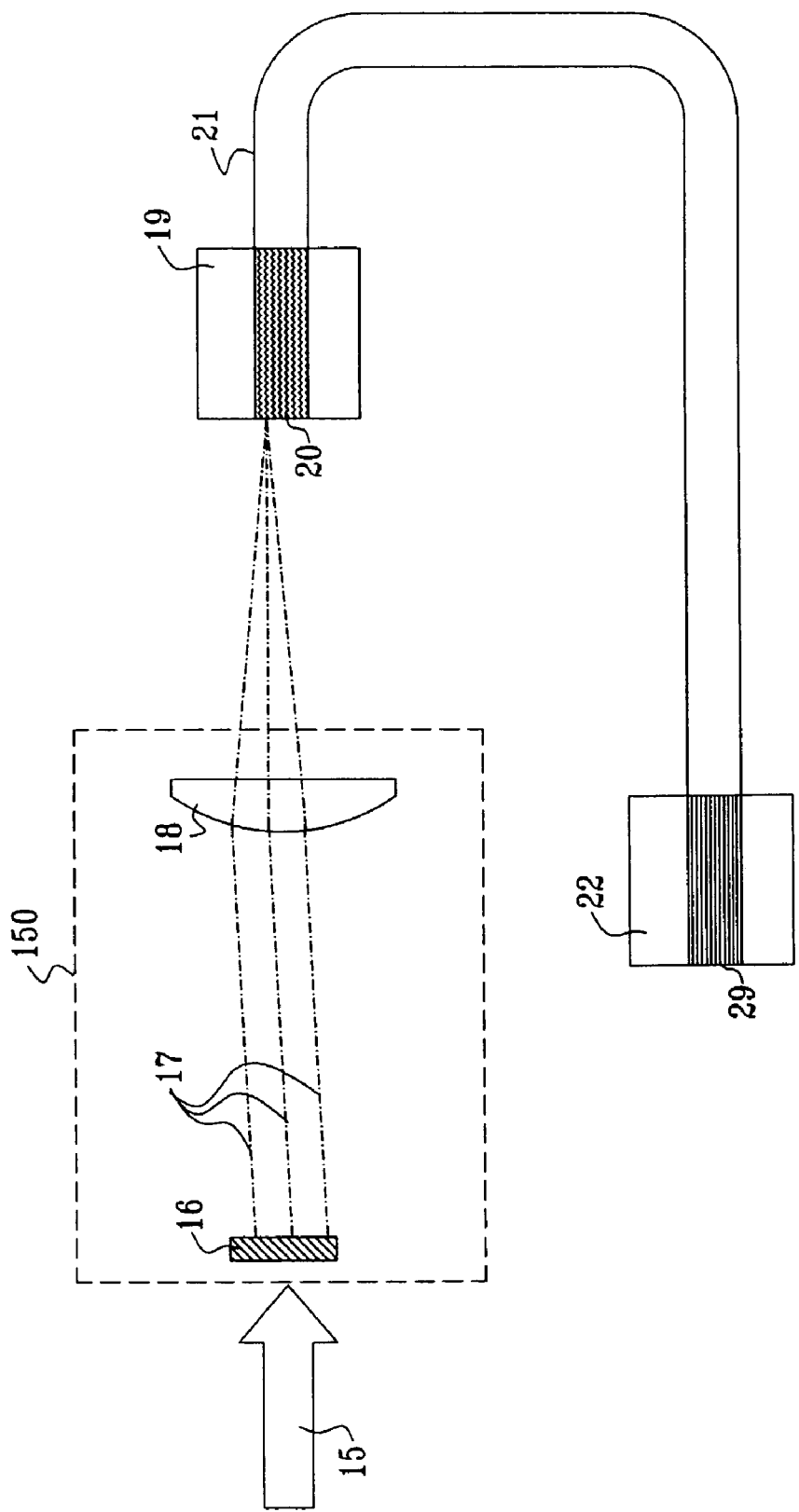
FIG. 8 is a schematic drawing of a fiber optical delivery bundle, according to a preferred embodiment of the present invention, such as that used in FIG. 7.

An implementation of this method, according to a preferred embodiment of the present invention, is schematically illustrated in FIG. 8. The laser beam 15, which can be either a parallel beam or slightly convergent, or slightly divergent impinges onto a diffusing element 16 which, according to alternative and preferred embodiments, can be a regular diffuser, a holographic diffuser (such as an MEMS) or a microlens array having a numerical aperture that spreads the incident light at the required angles. The diffused beam, shown schematically in FIG. 8 by means of three exemplary rays 17 diffused at the same angle from different locations in the diffuser, is preferably imaged onto one point of the end face 20 of the terminal connector 19 of a fiber optics bundle 21 by means of a focussing element 18, which can be either a single lens, or, in order to reduce aberrations, a multi-element lens. Rays diffused at different angles from those 17 shown in FIG. 8, are imaged onto different points of the end face 20 of the fiber optics bundle 21. Light from all of the included angles at which light is output from the diffuser is thus imaged by means of the focussing element 18 to cover the entire input aperture of the fiber bundle end face 20. The beam traverses the fiber bundle 21 and is output at the opposite end face 29 of the fibers at the output connector 22.

For optimum optical transfer efficiency, the diffusing element 16 is preferably positioned at the left focal plane of the focussing element 18, and the end face 20 of the fiber 21, at the right focal plane of the focussing element.

The half angle $\alpha$ of the diffusing element, and the focal length f, of focussing element are computed as follows.

If r is the input beam radius and NA is the numerical aperture of the fiber 21, then NA=r/f by definition. Thus f=r/NA. Now, if R is the fiber bundle radius than $\alpha*f=R$. Thus, for a specific input beam diameter and fiber diameter, the focal length and the diffusing angle can be simply calculated.

The embodiments generally described in the prior art of the use of fiber bundle to provide coherence breaking have disadvantages, relating to the effect of transmission losses in the fibers. In order to provide good coherence breaking, the difference in length between any pair of fibers of the bundle is described in the prior art as needing to be greater or equal to the coherence length of the light source. As a consequence, the difference in length between the fibers in the bundle is thus greater or equal to the coherence length times the number of fibers in the other bundle. Consequently, according to the criteria of the prior art, for a bundle containing hundreds or even thousands of fibers, there is an appreciable difference in length between the shortest and longest fibers of the bundle. This results in two disadvantageous effects in such prior art fiber bundles:

(i) Firstly, because of the transmission loses in typically used fiber materials, the light intensity output from each fiber of the bundle may be significantly different, falling with increasing fiber length. However, for the coherence breaking effect to be effective, there should ideally be only phase or time of flight differences between the various fiber outputs, and any differences in intensity contribution degrades the desired coherence breaking effect.

(ii) Secondly, the longer these differences in length, the longer the overall length of the bundle, and the longer the overall length of the bundle, the higher the transmission losses themselves, quite apart from their effect on the coherence breaking effects. These transmission losses make the illumination system inefficient and less cost-effective.

Figure 9A:
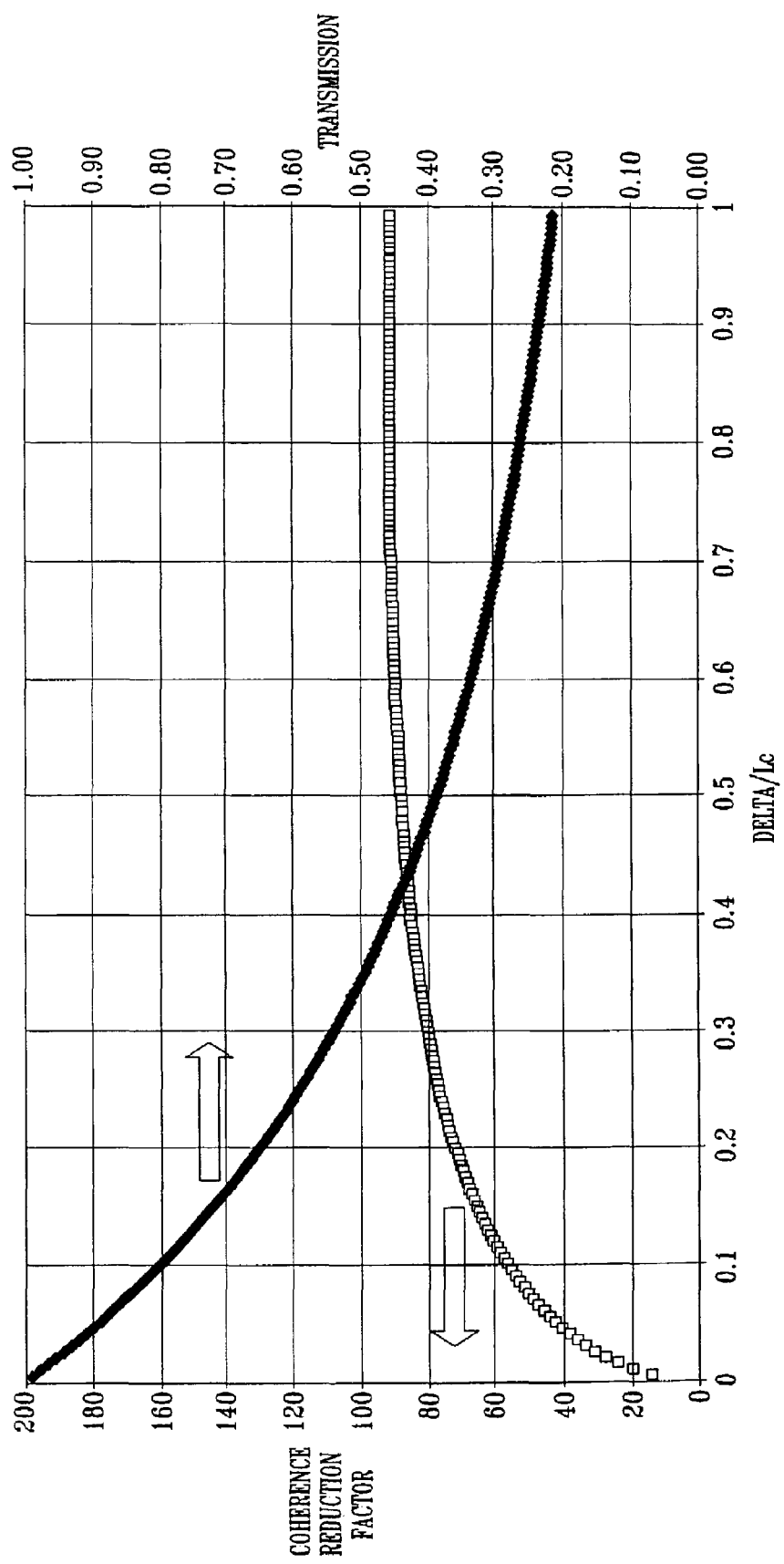

This effect can be illustrated by reference to FIG. 9A, which is a graphical illustration of the outcome of the above-described trade-off in fiber length difference between transmission and coherence breaking efficiency. The results shown in FIG. 9A are for a bundle containing 40,000 fibers, and for a fiber having a transmission loss in the UV of the order of 0.1 db/m. The two ordinates separately show the bundle transmission and the coherence reduction factor as a function of Delta/$L_C$, where each fiber differs in length by Delta mm., and the coherence length of the source is $L_C$. The transmission is measured relative to a bundle having uniform fiber lengths equal to the length of the shortest fiber in the variable fiber length bundle. The value of $L_C$ for the example shown is 5 mm.

For such a 40,000 fiber bundle, the maximum theoretical coherence reduction factor is given by $(40,000)^{1/2}=200$. As is observed in the graph, for Delta/$L_C$=1, meaning that the fiber optical length differences are equal to the coherence length, the coherence reduction factor is approximately 90, compared to the maximum theoretical 200. It is to be noted that the coherence reduction factor falls short of its theoretical value because the increasing insertion loss of each successive fiber means that the intensity contribution of each separate fiber to the total output is not equal, and the coherence breaking effect is thus reduced. The transmittance of the bundle, on the other hand, has fallen to approximately 0.22 of that of a bundle with Delta/$L_C$=0, i.e. with no length differences, and such a transmission loss is serious.

If, on the other hand, the fiber optical length difference is reduced to only 0.4$L_C$, the coherence reduction factor is reduced to approximately 85, which is only a 6% reduction, while the transmission is increased to approximately 0.45, which is over a 110% increase.

According to these results, there is thus provided, according to a preferred embodiment of the present invention, an illumination delivery fiber bundle, operative for breaking the coherence of light transmitted therethrough, in which the differences in lengths of the fibers in the bundle are less than the coherence length of the source. Such a bundle, which compromises slightly on its coherence breaking, properties by using fiber differences less than the coherence length, and thereby gains a substantial increase in illumination level, thus has significant economical advantages over the prior art bundles described above.

The above mentioned embodiments have been generally described in terms of typical pulsed laser sources, such as Nd:YAG lasers, where the coherence length is generally of the order of a few millimeters. It is evident that in systems using longer coherence length lasers, the problem is multiplied manyfold. Thus, for instance, a Helium-Neon CW laser typically has a coherence length of the order of 20 cm., under which conditions, the advantages of any of the various embodiments of the present invention become even more pronounced.

In order to improve the coherence breaking efficiency, it is known, for instance from the above-referenced U.S. Pat. No. 6,369,888, that it may be more economical to use two bundles with a smaller number of fibers in each, than one bundle with more fibers. If the fiber length difference in the first bundle exceeds the overall fiber length difference between the shortest and the longest fibers in the second bundle, then the effective number of fibers taking part in the coherence breaking process is the number of fibers in the first bundle times the number of fibers in the second bundle. This applies if the contribution of light to each fiber in the second bundle comes from all of the fibers in the first bundle.

Reference is now made to FIG. 9B, which is a schematic illustration of an optical arrangement for achieving this result, wherein a second bundle is provided serially with the first bundle of FIG. 8. From the exit end face 29 of the first bundle 21, three exemplary rays 23 propagating at the same angle from different locations in the end face 29, are shown being imaged onto the end face 26 of the fibers at the terminal connector 25 of the second fiber optics bundle 27 by means of a focusing element 24, which can be either a single lens, or a multi-element lens. The beam is output from the second fiber bundle 27 at the far end face 26 of the fibers at the output connector 28. It is not necessary that the diameter of the first bundle 21 be the same as the diameter of the second bundle 27, is shown in the preferred embodiment of FIG. 9B. If the first bundle has a smaller diameter, a diffuser is required at its end to increase the angular distribution of light from the end, in order to fill the input of the second bundle.

In the embodiment of the double fiber bundle arrangement described in U.S. Pat. No. 6,369,888, the fibers in both bundles are described as having a different length, and the difference in length ΔL between any two fibers in one bundle is preferably selected to be greater than the coherence length of the light source. The difference in length between any pair in the other bundle is described as being preferably larger than the difference in length between the shortest and the longest fiber in the first mentioned bundle.

However, in addition to the prior art disadvantage described above concerning the effect of the fiber length differences on the total intensity transmitted by the bundle, there is another disadvantage relating to the variation in intensity transmitted by the various fibers of the prior art double bundle embodiments. In order to provide good coherence breaking with a double bundle configuration, it is important that the phase-separated beamlets input to the second bundle, as generated by the different lengths of the fibers in the first bundle, should ideally be of equal intensity. Any departure from equal intensity results in degradation of the coherence breaking effect in the second bundle, since some of the differently phased output beams will be preferentially more intense than others, leading to a net residual coherence effect. In the above-mentioned Karpol et al patent, the difference in length between any pair of fibers in the first bundle is described as being preferably larger than the difference in length between the shortest and the longest fiber in the other bundle. The difference in length between any pair of fibers of that other bundle is described as being greater than the coherence length of the light source, such that the difference in length between the shortest and the longest fiber in the other bundle is thus greater than the coherence length of the light source times the number of fibers in the other bundle. The typical coherence lengths generated by lasers used for such applications are of the order of up to a few millimeters.

Consequently, according, to the criteria of this prior art, there is an appreciable difference in length between the fibers of the first bundle.

There is therefore also a second trade-off between two effects, which oppositely affect the efficiency of the coherence breaking. On the one hand, the differences between the lengths of the fibers in the second bundle should preferably be more than the coherence length in order to generate efficient coherence breaking in such a bundle, and on the other hand, the larger the difference in lengths between the fibers anywhere in the double bundle embodiment, the more the coherence breaking in the second fiber is degraded because of lack of unity of intensity.

Furthermore, in the above-mentioned Karpol et al., prior art, it is stated that the difference in length $\Delta L$ between any two fibers in one bundle is preferably selected to be greater than the coherence length of the light source. This preferred difference in length is longer than the optical path length in the fiber by a factor N, where N is the refractive index of the core material, such that this method proposes use of a longer length difference between fibers than is dictated by optical considerations, even before any incentive to reduce fiber length differences, as discussed hereinabove.

Figure 9C:
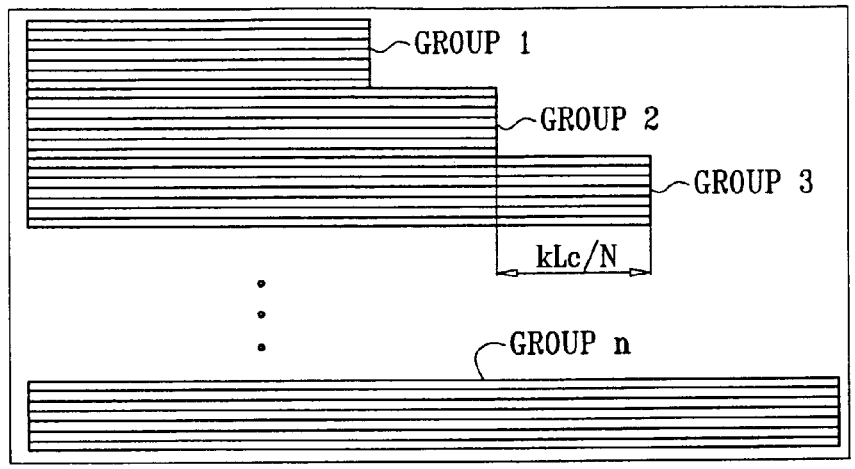
Figure 9D:
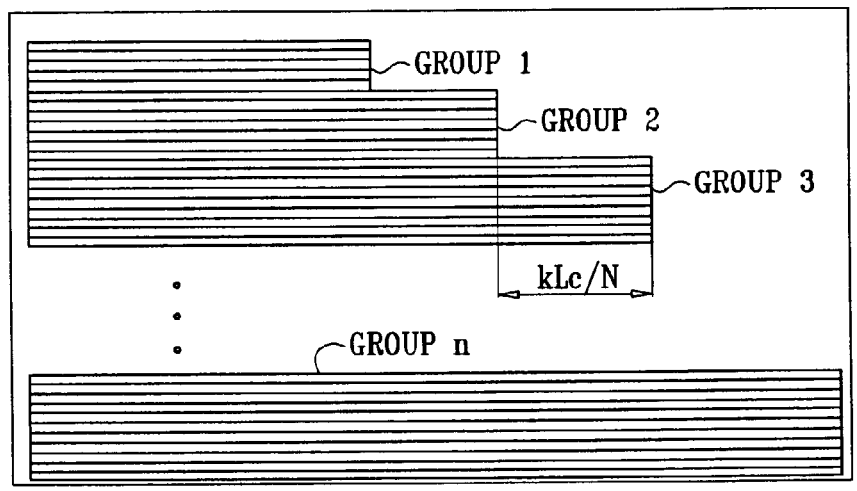

Reference is now made to FIGS. 9C and 9D, which respectively illustrate schematically the two bundles of a double fiber bundle delivery system, constructed and operative according to another preferred embodiment of the present invention. This embodiment is operative to diminish the above-described disadvantages of the prior art double fiber bundle delivery system. For the purposes of explaining the operation of this embodiment, the fiber bundle shown in FIG. 9C is regarded as the input bundle, denoted 21 in the embodiment of FIG. 9B, and the fiber bundle shown in FIG. 9D is regarded as the output bundle, denoted 27 in FIG. 9B, though it is to be understood that this embodiment is equally operable with the fibers in either order, if the correct matching components are provided.

Considering now the first bundle, in order to generate good coherence breaking, every fiber should optimally be of a different optical length by the sum of all the optical length differences between the shortest and the longest fibers in the second bundle. On the other hand, in order to avoid intensity variation effects from degrading the coherence breaking effect of the second bundle, equal optical length fibers should ideally be used, but this would generate no coherence breaking in the first bundle. There is therefore provided, in accordance with a preferred embodiment of the present invention, and as illustrated in FIG. 9C, a compromise bundle construction, in which the fibers are divided into groups, each group containing fibers of the same optical length, and each group preferably being different in optical length from another group in the bundle by the sum of all of the optical differences of the fibers in the second bundle. In the embodiment of FIG. 9C, therefore, the fibers within each group provide an element of uniformity to the beamlets output from the first bundle, while the difference in optical lengths between the groups provides the coherence breaking properties of the light from the different groups. The correct trade-off between these two effects is able to compensate to a large extent for the reduction in efficiency from the coherence breaking effect that would be obtained if all the fibers were of different optical lengths, but were also loss free, such that the intensity change effect was not a factor. The extent of the compensation between these two effects is a function of the attenuation per unit length of the fiber used.

According to yet another preferred embodiment of the present invention, instead of each group having the same number of fibers, as a result of which, the longer groups still have a lower light output than the shorter groups, it is possible to ensure that each group has the same transmitted intensity by varying the number of fibers in each group. Reference is now made to FIG. 9D, which is a schematic drawing of a bundle of fibers, according to yet another preferred embodiment of the present invention, similar to that shown in FIG. 9C, but in which the number of fibers in each group is increased according to the length of the group. Even more preferably, the number of fibers in each group is made generally proportional to the length of the group. In this way, the increased insertion loss arising in a group because of the additional fiber length in the group is offset by the increase in the number of fibers in that group.

A further advantage in the use of groups of fibers, according to this embodiment of the present invention, is that the redundancy effect of a large insertion of fibers operating in parallel has the effect of smoothing out any production differences which inevitably arise between supposedly identical fibers, both in optical properties and in targeted cleaved length.

Figure 9E:
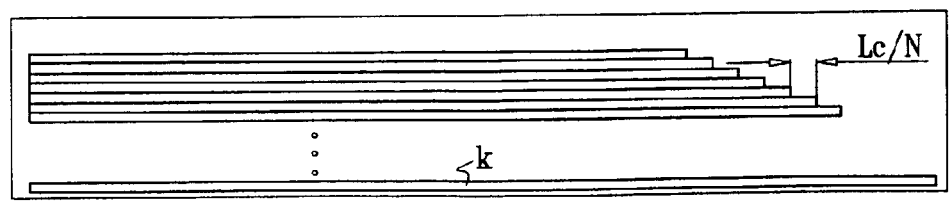

Reference is now made to FIG. 9E, which is a schematic drawing of the second bundle of fibers, according to this preferred embodiment of the present invention. In the second bundle, each of the fibers is preferably of a different optical length, the optical lengths differing by the coherence length of the light source, or less. Since the total overall difference in optical lengths of the fibers in the second bundle is determinative in fixing the difference in the optical lengths between the different groups of fibers in the first bundle, and as mentioned above, there is an advantage in keeping the path differences between fibers as short as possible to minimize intensity changes between fibers or fiber groups, there is an additional advantage to the first bundle parameters if the optical lengths of the fibers in the second bundle differ by as little as possible. For this reason, preferred use of fiber optical lengths differing by less than the coherence length of the light source can be advantageous in the second bundle, commensurate with achieving sufficient coherence breakage in the combination. The determination of how much less than the coherence length to use in a particular beam delivery system is ascertained according to the attenuation constant of the fibers used in the bundles, and in accordance with the above-described trade-off considerations.

According to the above mentioned preferred embodiments of the present invention, there is described a system comprising only one bundle of the type containing the groups of fibers, whether that bundle is positioned in front of or after the bundle containing the single fibers. According to more preferred embodiments of the present invention, in series with the bundle containing the single generally ungrouped fibers, a plurality of bundles with groups of fibers can be used, instead of a single such bundle, such that the illumination system comprises a series of bundles of fibers, with the groups of fibers and the fibers respectively optimally arranged for good coherence breaking properties and minimal transmission losses, as expounded hereinabove.

Some examples are now provided to illustrate one preferred embodiment of FIGS. 9C to 9E quantitatively. Reference is first made to the second bundle, as shown in FIG. 9E, which has k fibers, where k is preferably of the order of 1000. The length of a first fiber is L, where L is preferably of the order of 1 meter. A second fiber is longer than the first by $L_c/N$, where $L_c$ is the coherence length of the laser source, typically 6 mm, and N is the fiber core refractive index, generally of the order of 1.5, such that the fiber length difference is of the order of 4 mm. A third fiber is longer than the second also by $L_c/N$, and so on. The sum of all k length differences is thus $k \times L_c/N$, which amounts to the order of 4 meters for this preferred example.

The first bundle, as in FIG. 9C, has a number n of groups of fibers, where n is preferably 10 to 20. Each group contains m, preferably 20 to 50, fibers of equal length and equal optical path length. The length difference between each of the groups is equal to or greater than the sum of all of the length differences of the second bundle, which, in this preferred example, amounts to approximately 4 meters, as obtained above. From these numerical examples, the reason for limiting differences in fiber lengths to limit transmission loss changes, becomes evident.

The above-described embodiments of the present invention for achieving beam coherence breaking also result in a solution for a problem related to the use of short pulsed lasers in such illumination systems. Such short laser pulses, which can typically be as short as only a few nanoseconds, may have a peak power density so high that the focussed beam may cause damage to the wafer under inspection. A common method used to decrease the peak power of a short laser pulse is to stretch the pulse, such that the pulse energy is expended over a longer time, and hence has a lower peak power. Such pulse stretching can be performed by transmitting the pulse in parallel down several paths of different optical path length, and recombining after transit. This is the situation which exists with the assembly of variable length fibers in the bundles shown in the embodiments of FIGS. 8 and 9A-9E of the present invention, such that the fiber bundles of the present invention are also effective in pulse stretching applications.

To illustrate this application of the preferred embodiments of the present invention, the above mentioned numerical example will be used. For the preferred bundle having 20 groups, each different in length by 4 meters, a total length difference of 80 meters is generated. The time of flight of light in the medium of the fiber, having a refractive index of 1.5, is approximately 5 nsec/meter. Thus the total time of flight difference for an 80 meter bundle is approximately 400 nsec. The effect of the bundle is thus to generate pulse stretching from the typically few nanosecond pulse lengths emitted by the laser, to about two orders of magnitude longer, with the concomitant reduction in potential beam damage. For at least one bundle some or all of the optical path differences between fibers is less than the system's beam coherence length.

A particular feature of a preferred embodiment of the present invention is that the system includes a second fiber optic bundle, within which the optical path length difference between each pair of fibers is less than or equal to the coherence length of the light beam being employed by the system.

Reference is now made to FIG. 9F, which is a schematic illustration of an alternative and preferred apparatus for performing pulse stretching, according to another preferred embodiment of the present invention. The beam stretcher preferably comprises two highly reflective mirrors 180, 182, positioned apart from and parallel to each other, such that a beam can be repeatedly reflected between them, and is delayed for each passage between the mirrors by the time of flight between them. One of the mirrors 182, known as the output mirror, is cut away in a diagonal manner such that the fraction of an incident beam which is reflected from it is a function of lateral position across the mirror. Consequently, also the fraction of light which is transmitted beyond the mirror is a function of lateral position across the mirror. This cut away embodiment compensates the output beam for the fraction of light lost by absorption at each successive mirror reflection. Though the cut-away profile is shown as a linear profile in the drawing, it could equally well be of another shape, such as exponential, to provide more uniform output.

The mirrors are arranged such that the input beam 184 preferably skirts the input mirror 180, and is reflected at least once between the input mirror 180 and the output mirror 182. The mirrors are arranged at such an angle that at each double passage between them, the reflected beam moves laterally across the output mirror 1892, and an increasing fraction thereof is output. Each successive output part of the beam is delayed relative to the previous output part by the time of flight of the beam travelling the double path between the mirrors. Thus, by varying the mutual mirror alignment angle, which determines the number of reflections, and the distance apart of the mirrors, the beam stretching time can be adjusted. As an example of the use of this preferred beam stretcher, for mirrors set 90 cm. apart, and for a beam undergoing 20 double passages, a 120 nanosecond stretched pulse can be obtained, starting from a pulse of width less than 10 nanoseconds.

The input beam 184, can preferably be shaped spatially by suitably disposed optical elements in order to generate an elliptically shaped input beam 185, as will be discussed hereinbelow in relation to the embodiment of FIG. 14B.

The entire beam outputting the beam stretcher is preferably spatially reduced by means of a telescope arrangement, 183, as is known in the art. Referring now back to the embodiments shown in FIGS. 8 and 9B, this stretched pulse beam can then be passed through a diffusing element, 16, from where it is input into the fiber bundle 21. The advantage of using a beam stretcher before the first fiber bundle 21 is twofold. Firstly, it reduces the possibility of damage to the fiber bundle because of the high peak input power of the beam pulses, and secondly, it reduces the requirement for using such long fibers in the bundle, which in the previously described embodiments, were preferably provided to facilitate beam stretching as well as coherence breaking.

Figure 10:
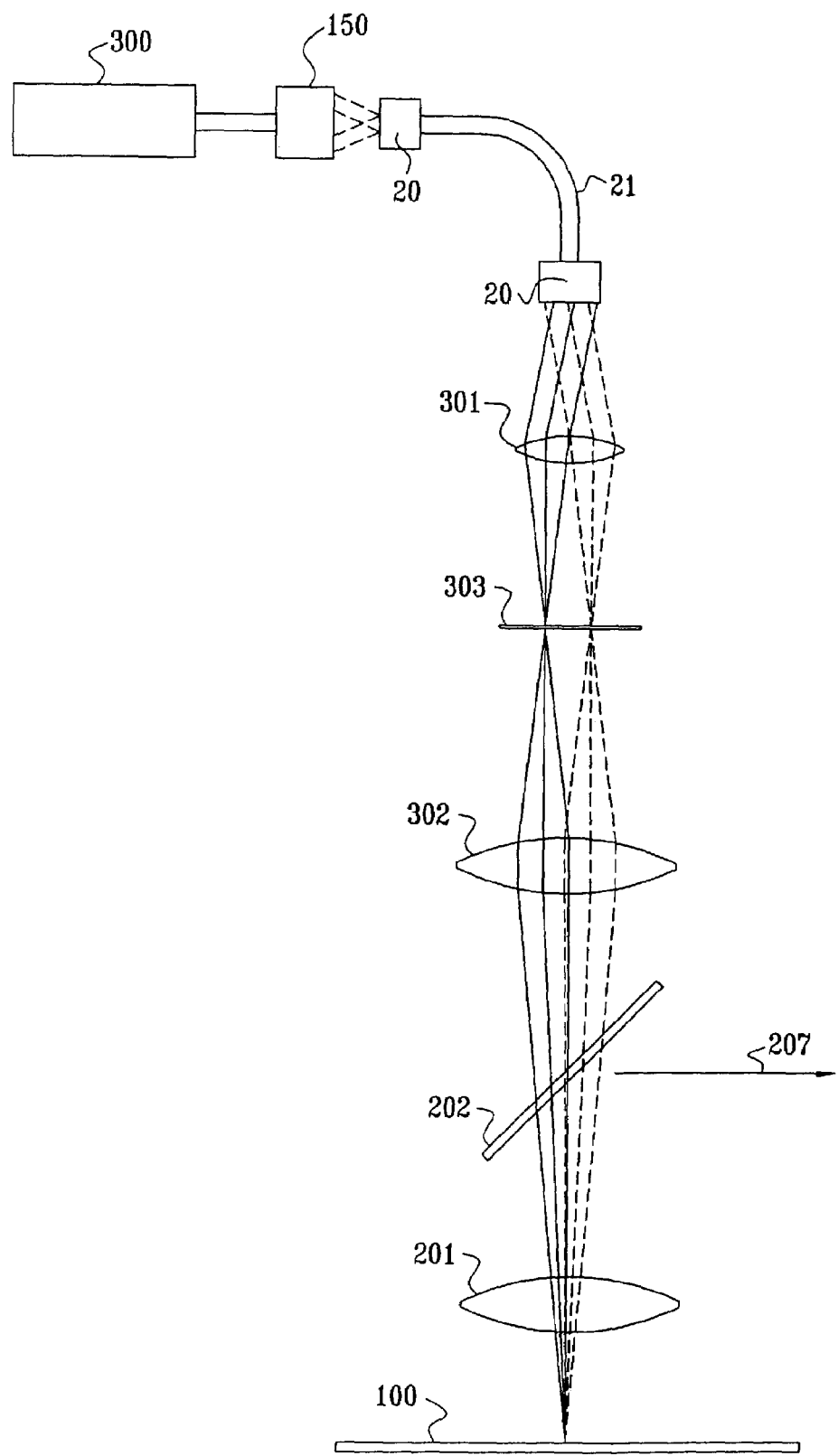
FIG. 10 illustrates schematically an arrangement for providing bright field illumination, according to a preferred embodiment of the present invention, including some novel aspects introduced to improve the illumination level on the wafer.

Reference is now made to FIG. 10 which illustrates schematically an arrangement for providing bright field illumination, according to a preferred embodiment of the present invention, including some novel aspects introduced to improve the illumination level on the wafer. A field stop plane 303, located preferably equidistant between the two transfer lenses 301, 302, is imaged through the objective 201 onto the object plane 100. The function of this field stop plane will now be explained.

Figure 11:
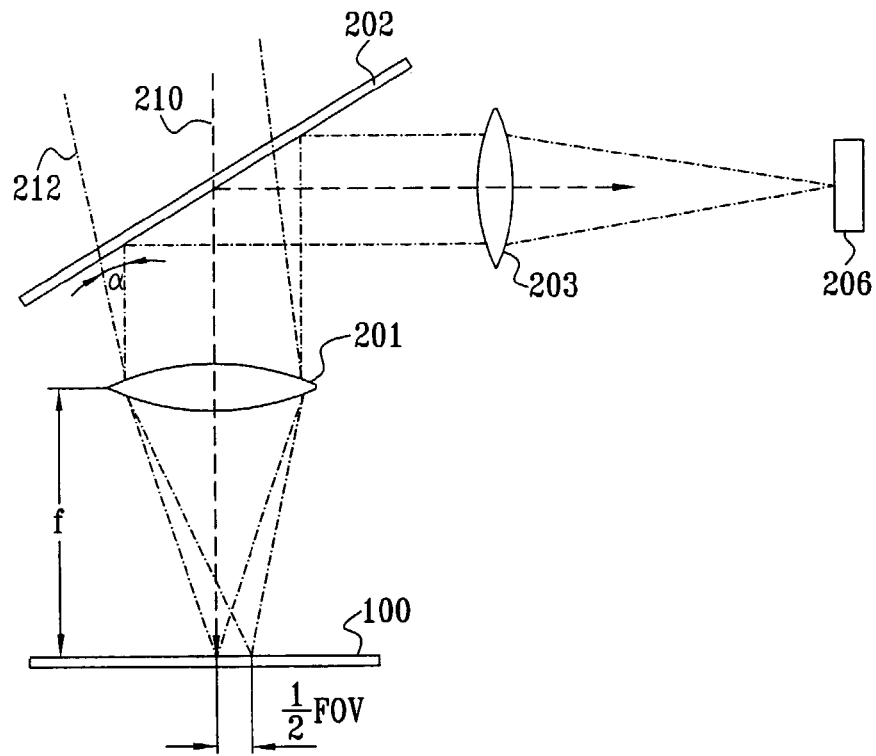
FIG. 11 is a simplified view of the illumination path through the objective lens of the embodiment of FIG. 10.

Reference is made to FIG. 11, which is a simplified view of the illumination path through the objective lens 201. In order to cover the entire field of view FOV on the wafer 100 situated in the object plane, the illumination path of rays 212 which illuminate one edge of the FOV have to reach the objective lens subtending a half angle α with the direction of the optical axis 210, where α is defined by the relationship:

$$2\alpha = FOV/f$$

where f is the focal length of the objective. The other reference characters shown in FIG. 11 have the same meaning as in FIGS. 7 and 10.

In addition, the illumination has to cover the full pupil of the objective lens in order to effectively use the full objective Numerical Aperture (NA). Otherwise, the system resolution is limited. Furthermore, optimal use of the coherence breaking fiber bundle as an illumination source in such an optical layout requires:

(i) that each fiber illuminates the entire FOV, and
(ii) that each point in the FOV is illuminated by all of the fibers.

Figure 12:
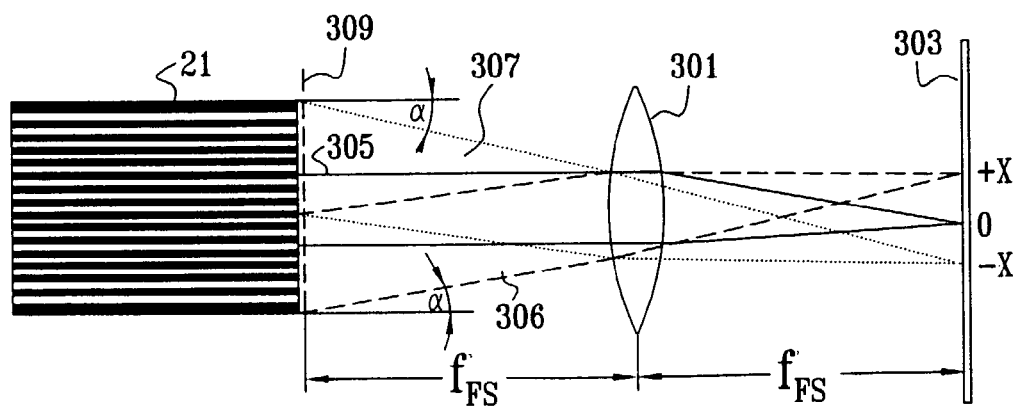
FIG. 12 illustrates a detailed optical arrangement for fulfilling the requirement of illuminating the entire numerical aperture of a fiber optical delivery bundle, according to another preferred embodiment of the present invention.

Reference is now made to FIG. 12, which illustrates a detailed optical arrangement for fulfilling these requirements, according to another preferred embodiment of the present invention. An intermediate plane, called the Field Stop Plane (FS) is defined, in which each point is illuminated by contributions from all of the fibers in the bundle. This field stop plane is then imaged through the objective onto the object plane.

In FIG. 12, light is shown emerging from the fiber bundle 21 at angles ranging from $\pm\alpha$ to the optical axis, and are focussed by the field stop focusing lens 301 onto the field stop plane 303. The field stop lens 301 should be spaced at a distance equal to its focal length $f_{FS}$ both from the source at the end of the fiber bundle 21 and from the field stop plane 303. Three sets of rays are shown. Rays emitted from the fiber bundle parallel to the optical axis, shown as fill lines 305, are focussed by the field stop lens 301 at point O on the field axis plane. Rays emitted from the fiber bundle at an angle $\alpha$ to the optical axis, shown in coarsely dashed lines 306, are focussed by the field stop lens 301 to a point +X on the field axis plane. Rays emitted from the fiber bundle at an angle $-\alpha$ to the optical axis, shown in finely dashed lines 307, are focussed by the field stop lens 301 to a point $-X$ on the field axis plane. This assembly of rays thus forms an illuminated area of dimensions $\pm X$, given by the expression $$X = f_{FS} * \alpha$$

where $f_{FS}$ is the focal length of the field stop focusing lens. For improved optical performance, the field stop lens 301 can preferably be a doublet.

If each fiber has a uniform angular intensity distribution, each point on the field stop plane is illuminated by all of the fibers, as required. A diffuser 309 at the fiber bundle output may preferably be used in order to smooth out the angular distribution.

Figure 13:
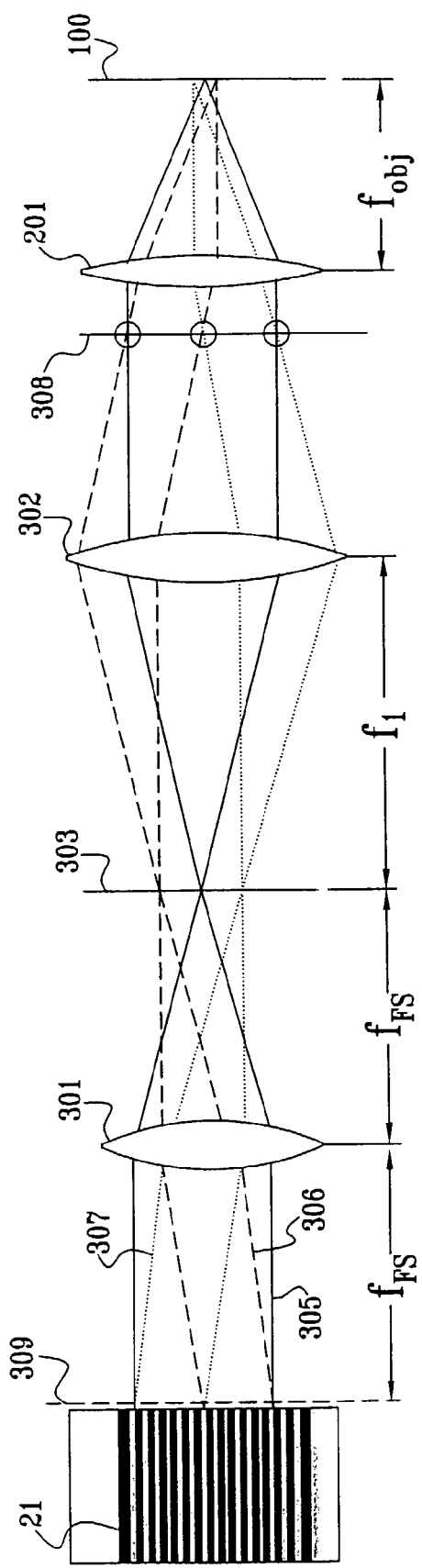
FIG. 13 is a schematic illustration of the complete bright field illumination system of a wafer inspection system according to another preferred embodiment.

Reference is now made to FIG. 13, which is a schematic illustration of the complete bright field illumination system, illustrating how the field stop plane 303 is imaged onto the object plane 100, by use of a transfer lens 302 operating in conjunction with the objective lens 201. The objective pupil is designated in plane 308. In FIG. 13 are shown the same three sets of rays as were shown in FIG. 12, emitted from the fiber bundle at angles of $\pm\alpha$, and parallel to the optical axis respectively. All the rays emerging from the fiber bundle at the same angle are seen to reach the same point within the field of view on the object plane. Non-uniform angular distribution of intensity at the output of the fiber bundle leads to non-uniform illumination at the FOV, and hence the need for a diffuser 309 at the fiber bundle output.

The field stop is positioned at the back focal distance $f_1$ from the transfer lens 302. The magnification of this optical arrangement is equal to $f_{obj}/f_1$, where $f_{obj}$ is the focal distance of the objective lens 201.

In order to calculate the parameters of the elements of this illumination optics, it is necessary to start with the fiber bundle diameter and the numerical aperture NA of the bundle output. The objective pupil 308 should be fully illuminated for optimum brightness. The image of the fiber bundle is formed, with magnification M, on the objective pupil 308 as shown by the small circles representing the image of the fiber bundle in that plane at the crossings of the three sets of rays shown, 305, 306 and 307. Therefore, the focal lengths of the field stop lens $f_{FS}$ and of the transfer lens $f_1$ are related by the expression:

$$M = f_1/f_{FS} = \text{objective pupil/fiber diameter.}$$

The illumination angle at the objective input must also be matched to the objective angular field of view, $\alpha$, giving a second relationship:

$$\alpha/NA = f_{FS}/f_1$$

where NA is the fiber numerical aperture. From these two expressions, values for $f_1$ and $f_{FS}$ can be calculated.

Figure 14A:
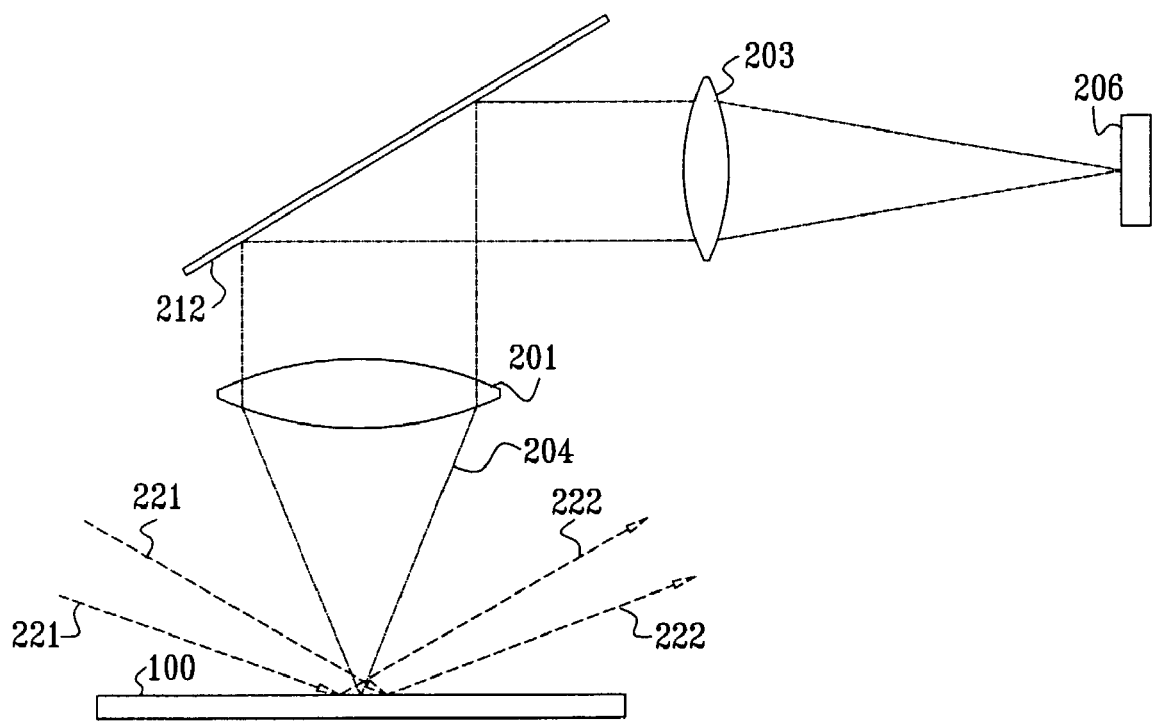
FIG. 14A illustrates schematically an arrangement for providing dark field side illumination for the system, according to a further preferred embodiment of the present invention.

Reference is now made to FIG. 14A, which is illustrates schematically an arrangement for providing dark field side illumination for the system, according to a further preferred embodiment of the present invention. Dark field illumination is generally used to detect small particles on the surface of objects. In the dark field embodiment shown in FIG. 14A, the incident light 221 falls on the wafer 100 at such a range of angles that the specularly reflected beam 222 is outside of the angle that the NA of the objective lens subtends, and does not therefore enter the detector 206. The incident light however, is scattered from small particles and pattern anomalies on the wafer in many directions, and part of this scattered light 204 is collected by the imaging optics, made up of the objective lens 201 and the imaging lens 203. A mirror 2212 replaces the beam splitter 202 used in the bright field configuration. The smaller the particle, the lower the scattering efficiency, and thus to detect small particle defects, a high incident light intensity is required.

It is important that the specularly reflected beam 222 is directed as far as possible from the collection angle of the objective lens. Since it is required that the objective lens should have a high NA to optimize light collection, the incident beam should have a relatively smaller NA. The size of the field of view in high NA imaging lenses, typically 0.3-0.8, is rather small. This accentuates the need to maintain high brightness in the illumination system. When introducing the laser beam into a fiber bundle, as explained hereinabove, the diameter of the bundle and the NA of the fibers in the bundle determine the brightness at the output of the bundle. Therefore it is desired to use fibers with low NA (<0.12) and a small bundle diameter. If the fiber diameter is too small, laser damage may occur at the fiber input side, such that a compromise fiber size between these two factors must be chosen.

Figure 14B:
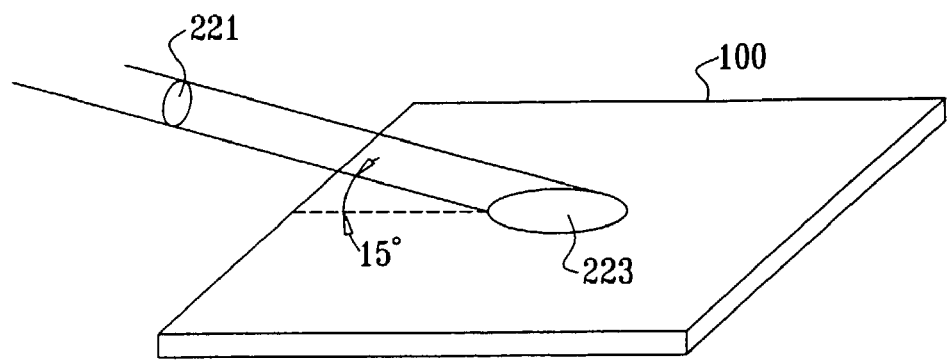
FIG. 14B illustrates schematically the method of illuminating the wafer with a beam having an elliptic shape with the opposite aspect ratio to that with which a circular beam would illuminate the wafer.

Another source of brightness loss in such a dark field illumination system is illustrated in FIG. 14B, and arises from the fact that when the light is incident at a low angle on the wafer, the illumination spot is smeared along the direction of incidence on the wafer. Thus, for instance, at an incident angle of 15° to the wafer surface, a circularly cross-sectioned beam 221 generates on the surface of the wafer 100, an ellipse 223 with an aspect ratio of approximately 4, thereby reducing the illumination brightness accordingly. According to another preferred embodiment of the present invention, this effect is countered by illuminating the wafer with a beam having an elliptic shape with the opposite aspect ratio.

Therefore, the requirements for dark field illumination, including both the above described criteria, and the general criteria previously discussed in relation to the requirements of bright field illumination, can be summarized as follows:

(i) Light should be incident on the object plane at an angle that is larger than the angle subtended by the NA of the objective lens.
(ii) Illumination should be performed at a small NA.
(iii) The size of the illuminated area should at least be the size of the FOV.
(iv) The illuminating beam should be in the form of an ellipse, or similar.
(v) The illumination system should be as incoherent as possible.

(vi) Each point in the FOV should be illuminated by all the fibers in the bundle conveying the dark field illumination.

Figure 15:
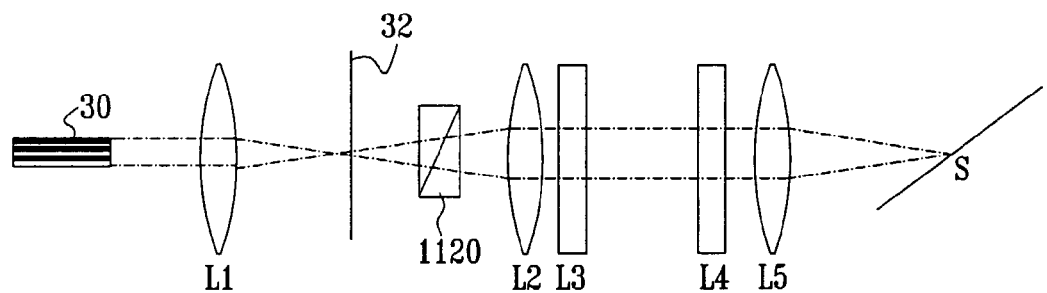
FIGS. 15 and 16 are schematic drawings viewed from two orthogonal directions, of an optical system according to another preferred embodiment of the present invention, for generating an elliptic or rectangular beam for the dark field illumination beam shape of FIG. 14B.
Figure 16:
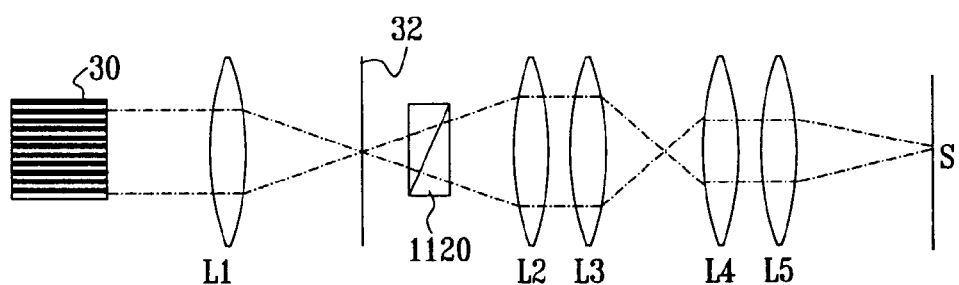

Reference is now made to FIGS. 15 and 16, which are schematic drawings viewed from two orthogonal directions, of an optical system according to another preferred embodiment of the present invention, for generating an elliptic or rectangular beam for dark field illumination. The illumination source is provided from a fiber bundle having an elliptic or rectangular shaped output. In a similar manner to that described in relation to the bright field illumination, a field stop plane is first generated, and this plane is then imaged onto the wafer. In order to provide the elliptic or rectangular shaped beam, a cylindrical telescope is used which transforms the circular field stop image into an ellipse. The aspect ratio required depends on the incident angle of the dark field illumination on the wafer. The optical system must be capable of generating the desired aspect ratio of the beam, but without increasing the NA of the beam in the broad dimension.

In FIG. 15, the rectangular bundle 30 is seen from its narrow dimension and in FIG. 16, from its broad dimension. L1 is the lens that generates the field stop image 32. Each point in this plane is illuminated by all of the fibers in the bundle. The field stop has a circular shape, since the NA of the fibers in the bundle are all the same. However, since the fiber bundle end is of a rectangular shape, the incident angle (NA) of the illumination in the field stop plane is smaller in the narrow dimension than in the broad dimension planes of FIGS. 15 and 16 respectively. The object of the projection optics is to take this field stop plane, and to image it onto the object plane, reducing it in the narrow plane but without increasing the incident angle (NA) on the object plane.

This task is accomplished by means of a telescope composed of lenses L2 to L5. Lenses L2 and L5 are two spherical lenses that form a telescope, preferably of unity magnification, that image the field stop plane onto the object plane at point S. L3 and L4 are cylindrical lenses that together comprise a reduction telescope in their cylindrical plane, but no refractive power in the other plane. The cylindrical lenses are aligned such that they have no refractive power in the plane parallel to the narrow dimension (FIG. 15). As a result, the field stop image in the narrow dimension plane has a reduced dimension, but the same limited NA as that in the broad dimension plane. The illumination spot, having a reduced dimension in this direction, when projected onto the effectively inclined object plane at S, generates an essentially equi-dimensioned illumination spot, but without an increased NA in either direction. Each lens can made from more than one element in order to reduce aberrations.

According to an alternative preferred embodiment, a rectangular field stop is generated by using cylindrical optics having different focal lengths in the "top view" and "side view" planes. Once this rectangular field stop image is obtained, then a conventional spherical telescope can be used to image the rectangular field stop plane onto plane S.

In some of the process steps required to be inspected by the system of the present invention, there is a dielectric layer on top of a patterned metal layer. In order to be able to inspect for defects on or very close to the surface of this dielectric layer, and also for defects occurring in the metallic layers embedded under the dielectric layer, or inside the bulk of the dielectric layer, there is further provided, according to another preferred embodiment of the present invention, a polarization technique, in which the illumination beam is polarized and thereby enables all of the above-mentioned types of defects to be viewed more efficiently.

Figure 17:
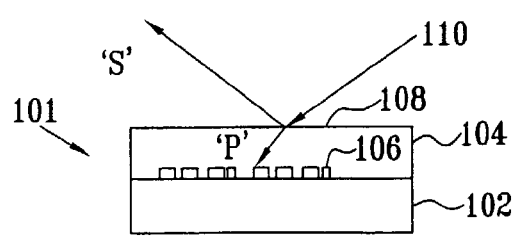
FIG. 17 illustrates a beam polarization technique according to another preferred embodiment of the present invention, to enable different types of defects to be viewed more efficiently.

Reference is now made to FIG. 17, which is a schematic illustration of the way in which this technique operates on the sample, according to one preferred embodiment. In FIG. 17, there is shown a sample wafer section 101 having a silicon layer 102 covered with a transparent dielectric layer 104. The silicon layer has a number of features 106, beneath the dielectric layer, which is it desired to inspect. In addition, it is also desired to inspect the surface 108 of the dielectric layer. It is known in the art that the s-polarization component of the incident beam has a high coefficient of reflectivity from the dielectric surface 108, and thus is sensitive to small particles residing on top of the dielectric surface, while the p-polarization component has a much lower reflexivity, and therefore penetrates the dielectric layer, and is first reflected or scattered from an underlying metallic layer, or from any another embedded feature within the dielectric layer which causes its reflection or scattering.

Reference is now made back to item 1120 of FIGS. 15 and 16, which illustrates how this differential polarization illumination system can preferably be implemented. Since the illumination issuing from the fiber bundle is generally completely unpolarized, a polarizing cube 1120 is inserted into the beam path of the illumination system, after the field stop plane 32. When it is desired to view surface features of the wafer, the polarizer is aligned to output the s-polarization component of the incident illumination. When it is desired to view deeper layers of the wafer, the polarizer is aligned to output the p-polarization component of the incident illumination. Alternatively and preferably, each polarization direction may be selected by the insertion of separate dedicated polarization cubes for each polarization direction desired. Additionally, a non-polarizing dummy cube can be used, to maintain the same optical path length in the system, when unpolarized illumination is desired. It is to be understood that although this preferred embodiment shows a polarization splitting cube, any other polarizing element which splits the incident light into its separate s- and p-polarization components could equally well be used.

Figure 18A:
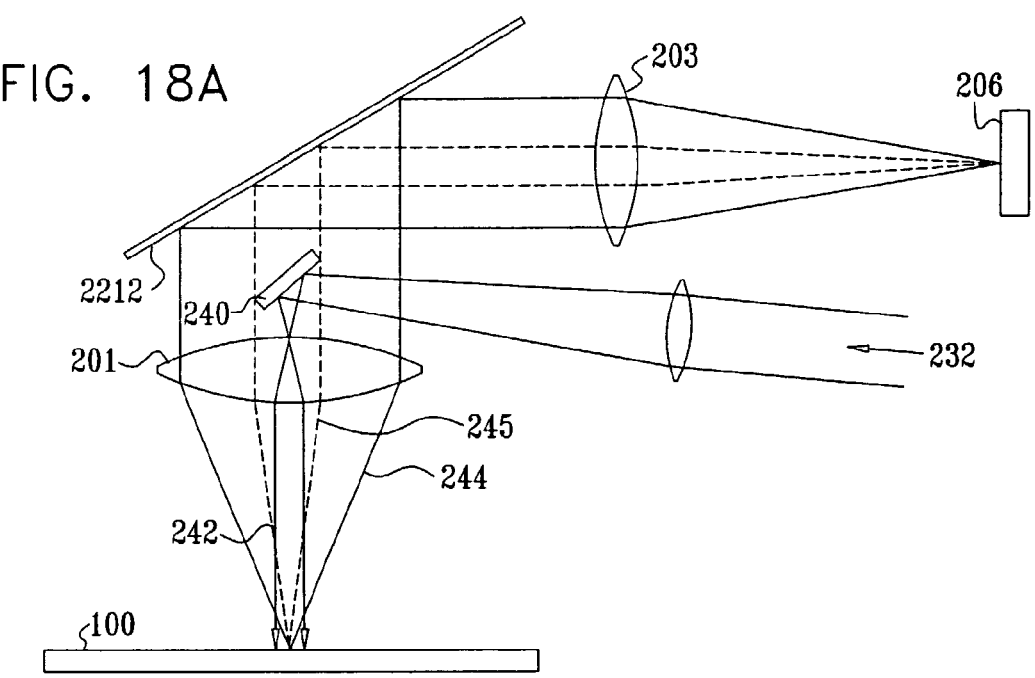
FIGS. 18A and 18B schematically illustrate arrangements for providing orthogonal dark field illumination for the inspection system of the present invention.
Figure 18B:
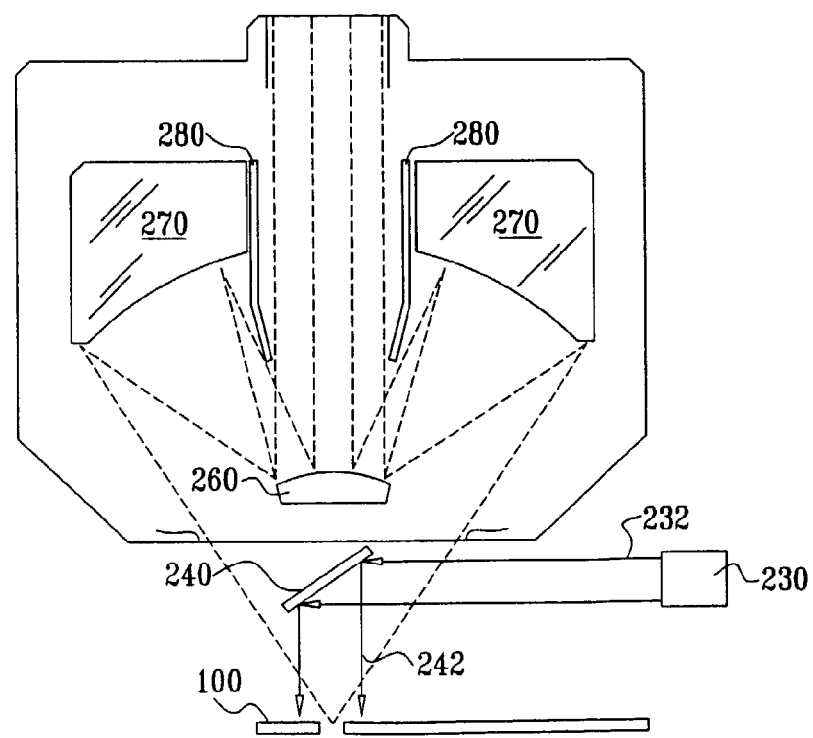

Reference is now made to FIGS. 18A and 18B, which schematically illustrate an arrangement for providing orthogonal dark field illumination for the system according to a further preferred embodiment of the present invention. Such illumination is also known as obscured reflectance illumination, because of its method of operation. FIG. 18A illustrates the overall schematic optical arrangement for operation of the method, while FIG. 18B is a schematic illustration of a preferred reflection type of objective, constructed and operative according to a further preferred embodiments of the present invention, for use with orthogonal dark field illumination.

In this mode of illumination, a parallel or semi-parallel beam 242 is incident on the target perpendicularly to illuminate all of the desired field of view. Scattered light 244 from objects on or within the target is collected by the objective 201, and after reflection by the dark field mirror 2212, is imaged by means of lens 203 onto the detector 206. Such a mode of illumination, which, unlike dark field side illumination, impinges normally on the wafer, has an advantage when there is a need to detect defects buried in inner transparent layers of the wafer.

Since the specularly reflected light would drown out any signal of interest from the scattered light, there is a need to block the path of the direct specularly reflected light. This is shown in FIG. 18A by the presence of the mirror 240, which selves the double function of directing the illumination beam 232 incident from the side, into a direction normal to the wafer 100, and of obscuring specularly reflected light from being collected by the objective. The objective thus collects only a hollow cone of scattered light from the object, as defined by the region between the full NA of the objective, delineated by the full line 244, and the region obscured by the mirror 240, as delineated by the dotted line 245.

However, if a conventional refractive optics objective is used, as shown in the embodiment of FIG. 18A, the task of masking the specular reflection and collecting the scattered light is complicated by the scatter and reflection of light in the objective element itself In order to overcome these complications, a reflective objective may be used, providing significant advantages in this application over conventional refractive objectives. Such a reflective objective is shown in FIG. 18B. As in FIG. 18A, the illumination 232 is incident from one of the sides and a tilted plane mirror 240 reflects the light normally onto the wafer 100. The objective itself is made up of two curved mirrors 270, 260, between which the scattered light is reflected until transmitted out of the objective towards the imaging lens. The curved mirrors 270, 260 are preferably of spherical profile, though aspherical surfaces could also be used as is known in the art, in order to reduce aberrations. The curved mirror 260 also functions as the obscuration stop for preventing the specularly reflected light from entering the objective, such that only the scattered light that is directed at angles larger than that defined by the mirror edge can be collected by the objective aperture. The tilted plane mirror 240 is arranged to be located directly beneath the curved mirror 260, and no larger in size than the curved mirror 260, such that no further obscuration is produced. After focussing between the two curved mirror 270, 260 of the objective, the scattered light is directed up through the exit aperture 280 of the objective as a annular beam of light.

The light source 230 can be either a direct laser beam or light coming from a fiber bundle, as discussed in the bright field illumination embodiments hereinabove. Use of a small diameter fiber bundle with a small numerical aperture and then expansion of the beam to illuminate a larger area than the diameter of the fiber, is effective in reducing the illumination beam angle.

The wafer inspection system according to the present invention is an automatic system for detecting defects. All the inspection parameters are preferably programmed according to the product layer step of the production process. The optical imaging mode may be considered as being one of those parameters. During programming, the user may choose to inspect a specific layer in the Bright Field mode or in one of the Dark Field modes, depending on where in the wafer, and of what type the sought-for defects are expected to be. According to a further preferred embodiment of the present invention, the system is constructed to switch between the different modes of illumination as described in the schematic drawing of FIG. 19.

According to another further preferred embodiment of the present invention, the different modes can be provided with different wavelengths of illumination, each wavelength being selected for optimum detection efficiency for the defects to be detected. Thus, for example, it is known that the scattering efficiency of a small defect of given size is proportional to $1/\lambda^4$, where $\lambda$ is the wavelength of light used to view the defect. As a result of this basic physical effect, it is evident that the shorter the wavelength of the illuminating light, the higher the scattered intensity from a small defect. Consequently, in order to detect efficiently in the dark field modes, where scattered light is used, it is advantageous to use as short a wavelength illumination as possible, and for the commonly used Nd:YAG source, the third harmonic in the UV is a convenient short wavelength harmonic. In general, in order to increase the resolving power of the optical system, which is inversely proportional to $\lambda$, the shortest practical illumination wavelength providing sufficient illumination power is generally used According to another preferred embodiment of the present invention, the second harmonic of the Nd:YAG laser is preferably utilized in order to execute an auto-focus function in the present system, while the illumination for the wafer imaging system, for the reasons described above, is operating at the third harmonic. Preferred operation of the auto-focusing system at a wavelength different from that of the imaging system is generally preferred, since the auto-focusing system is generally based on the use of a bright field image, while the wafer imaging system may be operated in one of the dark field modes. The use of different wavelengths for these two functions then facilitates separation of the auto-focusing signal from the wafer image data signal.

Figure 19:
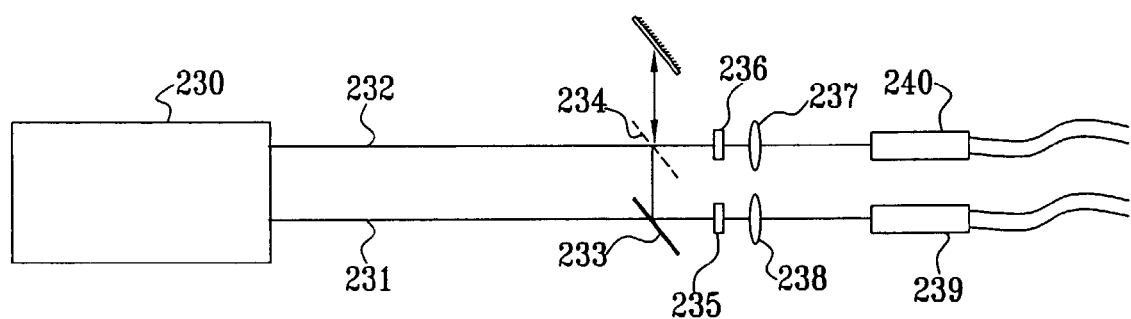
FIG. 19 schematically shows an illumination system constructed to switch between different illumination wavelengths.

In the preferred embodiment shown in the opto-mechanical layout of FIG. 19, the laser source 230 includes harmonic generators which preferably produce the second harmonic in the green, and the third harmonic in the ultra violet. The components are mounted on a laser-bench, which includes the laser source and switchable mirrors operable to direct the green and UV beams. The bench preferably also includes two fiber bundles and two optical coupling means for introducing the beams into the fibers, either in the bright field or a dark field mode.

The laser source 230 is preferably a Nd:YAG laser emitting a second harmonic green beam 231 at 532 nm, and a third harmonic UV beam 232 at 355 nm. The green beam 231 is directed at all times into the bright field fiber bundle 239 by means of a dichroic filter 233, that transmits the green and reflects the UV beam. The green beam 231 is introduced into the bright field fiber bundle 239 through a diffuser 235 and a focusing lens 238, as described hereinabove. The UV beam 232 may be directed either to the dark field fiber bundle 240 or to the bright field fiber bundle 239 by motion of the mirror 234 into and out of the UV beam path. When the mirror is in the beam path 232, it reflects the light to the dichroic filter 233 that reflects the UV beam into the fiber bundle 239. When the mirror 234 is out of the beam path, the UV beam is directed to the dark field fiber bundle 240 through a diffuser 236 and a lens 237. Mirror 234 is mounted on a mechanical translation stage that is motorized and controlled by the system computer and controller. In the above manner, the system according to these preferred embodiments of the present invention, is able to use the most efficient wavelength for imaging or auto-focusing functions, as described above.

According to various preferred embodiments of the present invention, a repetitively pulsed laser source is used in the illumination system, and a preferred type of laser is a Q-switched flash lamp excited Nd:YAG laser, such as the Model CFR 400 supplied by Big Sky Laser Corporation of Bozeman, Mont., U.S.A. Such lasers generally have large variations in pulse-to-pulse energy or intensity. Such variations make die-to-die comparison problematic, and though methods are available which make it possible sometimes to correct some of the variations by means of image processing techniques, a much more efficient and universally applicable solution is to stabilize the laser intensity.

In such lasers, optical pumping is performed by a flash lamp that excites the relevant energy levels in the Nd:YAG rod. The output power of the laser depends on the timing of the opening of the Q-switch after flash lamp pulse ignition. There is an optimum timing delay which gives maximum laser pulse output, and divergence from this value, either shorter or longer, results in a lower laser pulse output. In this type of laser, the Q-switch delay time is generally in the range of 100 to 200 μsec. According to another preferred embodiment of the present invention, there is provided a method of controlling the pulse to pulse laser power by changing the value of this delay time from pulse to pulse.

In such a Q-switched Nd:YAG laser, there are two major contributions to the laser output variation from pulse to pulse. One is the variation of the flash lamp radiation itself, typically arising from, though not limited to, random variations in the capacitor charge, or in the driving circuits, or in the lamp itself. A change in excitation level of a flash has a direct and immediate effect on the intensity of the resulting laser pulse. The other contribution occurs over a longer time interval and generally arises from changes in the temperature gradient in the YAG crystal and/or in the harmonic generator crystal if a higher harmonic output is being used, or from other thermal effects in any of the lasing components which result in a change in the laser pulse output.

Figure 20:
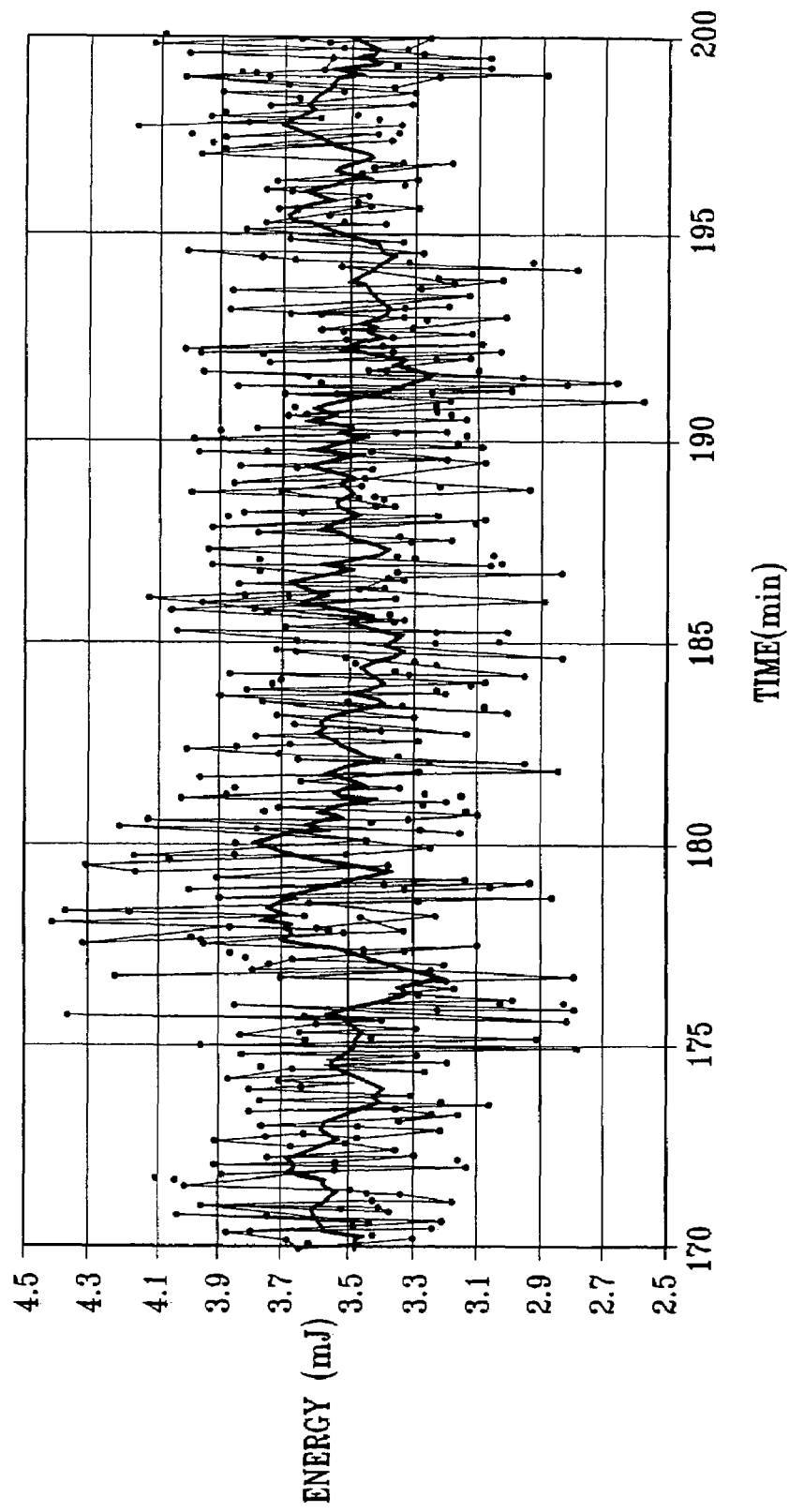
FIG. 20 is a graph showing an example of the laser pulse to pulse variations over time, taken from a timed plot of the output energy of a train of nominally 3.5 mJ pulses, generated by a Q-switched Nd:YAG laser, as used in the inspection system of the present invention.

Reference is now made to the chart shown in FIG. 20, which is an example of the laser pulse to pulse variations over time, taken from a timed plot of the actually measured output energy of a train of nominally 3.5 mJ pulses, generated by a Q-switched Nd:YAG laser. It is observed that there are very fast pulse to pulse energy changes, this being due to changes in the flash output from pulse to pulse. By plotting a moving average, which, in the case of the example plot shown in FIG. 20, is taken over 15 pulses, it is observed that there is also a slower variation component to the pulse output energy.

Figure 21:
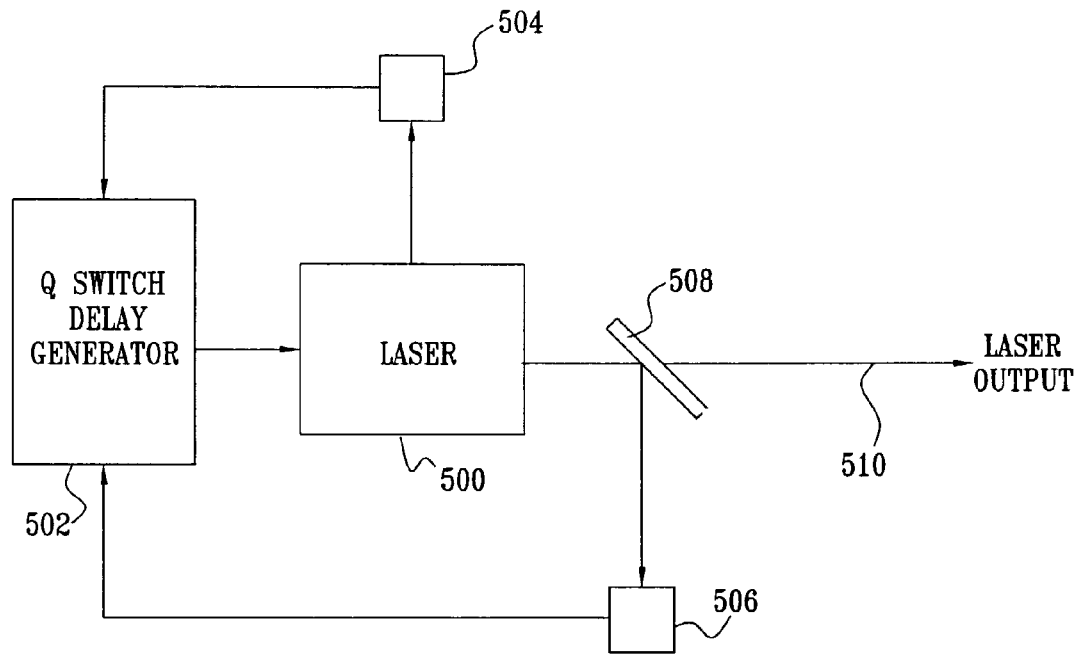
FIG. 21 is a schematic diagram of a circuit, according to another preferred embodiment of the present invention, used to compensate for variations in pulse to pulse output energy in a Q-switched laser, such as those shown in FIG. 20.

Reference is now made to FIG. 21, which is a schematic diagram of a circuit, according to another preferred embodiment of the present invention, used to implement a method of compensating for variations in pulse to pulse output energy in a Q-switched laser. The Q-switch timing delay circuits within the laser 500 are controlled by means of a Q-switch delay generator 502. The delay generated, generally in the range of 100-200 μsecs, is controlled by means of two inputs. One input is taken from a flash lamp sensor 504, situated either within the laser enclosure at a location where it can sample the output light of the flash lamp or lamps, as shown in FIG. 21, or in a position where it can sample the output laser beam, from which the pump light can be seen within the lasing crystal. This sensor adjusts the Q-switch time delay after each flash according to the flash intensity itself, such that the output of the resulting laser pulse is compensated for changes in the flash output.

A second sensor 506 measures a sample of the laser output pulse, preferably by means of a beam splitter 508, typically splitting off about 1% of the laser output 510. The signal from this sensor 506 is also used as an input into the Q-switch delay generator, which detects the trend in the laser output from pulse to pulse, and adjusts the Q-switch delay in order to attempt to counteract this trend in the next laser pulse. The extent of the Q-switch delay adjustment generated is dependent on the level of the change in laser pulse output in comparison with the previous pulse or pulses. According to one embodiment of this preferred method, the value of the derivative of the moving average of pulse outputs is used as a measure of the trend in long term pulse output drift, and this derivative is used to generate the control signal input to the Q-switch delay generator. Thus, for instance, if the derivative is positive and comparatively large, it is a sign that the laser pulse output needs reducing in order to keep the pulse to pulse output constant, and the Q-switch delay time is therefore adjusted to reduce the laser pulse output. In order to provide positive closed loop control of the required delay time, the mean operating delay time is chosen to be slightly less than the optimum delay for maximum pulse output, so that correction can be performed both to increase and to decrease the pulse output, as required. This compensation mechanism is generally operative to compensate for the: longer term variations occurring between laser pulses, generally of thermal origin.

By monitoring both the flash lamp light output and the laser power output, the Q-switch delay can thus be controlled in a closed loop, thus stabilizing the laser pulse power in real time, both for same-pulse and longer term variations.

According to another preferred embodiment of the present invention, use is made of the generally known phenomenon that harmonics of the laser are more sensitive than the fundamental output to variations in operating and environmental conditions of the laser, and that monitoring of the harmonic output results in a more sensitive long-term variation correction than monitoring of the fundamental output. In the preferred example of the Q-switched Nd:YAG laser, the third or fourth harmonic in the ultra-violet is preferably monitored, instead of the fundamental 1064 nm infrared lasing line. The harmonic output is preferably sampled by means of a suitable dichroic mirror at the output of the harmonic generator.

Since the depth of focus of an optical system capable of detecting defects in a wafer of the order of fractions of a micron is smaller than the expected flatness of the wafer and its associated vacuum chuck, there is a need to maintain active tracking of the optics focus during a detection scan. According to a further preferred embodiment of the present invention, there is thus provided an automatic Autofocus mechanism, based on optical detection of the focal position, and a feedback loop driving a motor operative to move the wafer along the optical axis to keep it in focus during the inspection procedure.

Figure 22A:
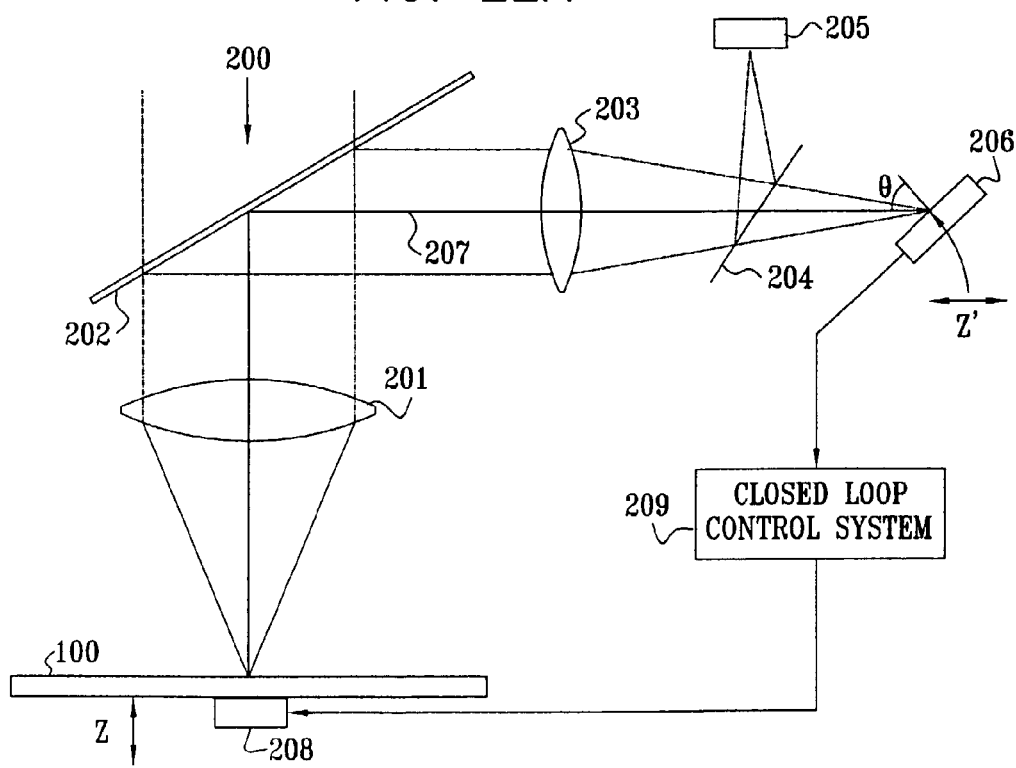
FIG. 22A is a schematic side view of a first automatic focussing arrangement, constructed and operative according to another preferred embodiment of the present invention.

Reference is now made to FIG. 22A, which is a schematic side view of a first automatic focusing arrangement, constructed and operative according to another preferred embodiment of the present invention. In FIG. 22A, the incident illumination light 200, such as that output in fiber bundle 239 of the embodiment shown in FIG. 19, is preferably composed of both the green and the UV, being the second and third harmonics respectively of the Nd:YAG laser. This illumination light is incident on the wafer 100 through the illumination beam splitter 202 and the objective lens 201. The light reflected from the wafer passes through imaging lens 203 and is then split into its two components by means of a dichroic filter 204. The UV light is preferably reflected and forms an image on detector 205, which is the image used in the wafer inspection procedure. The green light is transmitted through dichroic mirror 204 and forms an image on detector 206, which is the image used in the auto-focusing procedure. Detector 206 is tilted at an angle θ to the optical axis 207, so that only part of the image can be properly in focus. The system is aligned in such a manner that when the image at detector 205 in focus, which is the optimum focal position of the system, the part of the image that is in focus on detector 206 is located at the center of the detector. This is the basic focused starting position of the system.

The use of different wavelengths for the imaging and the auto-focusing functions is advantageous in the inspection system of the present invention, since the contrast and brightness obtained in the dark field illumination mode, which is that preferably used for detecting surface defects, is lower than that obtained in the bright field illumination mode, and thus less suitable for use in an auto-focusing application. According to this preferred embodiment, the auto-focusing function can thus be efficiently operated at one wavelength in the bright field mode without interfering with the dark-field defect inspection mode operating simultaneously at the second wavelength.

When the object plane moves relative to the objective lens 201 by a vertical distance z, the position of correct focus at detector 206 moves along the optical axis 207 from the original focal position, by a distance z', given by the expression $z'=z*m^2$, where m is the lateral optical magnification of the pair of lenses 201 and 203. Because of the angle of the detector 206, the best focused image on detector 206 will no longer be in the center of the detector, but at a lateral distance from the center equal to z'/sin θ, where θ is the tilt angle of the normal to detector 206 relative to the optical axis 207. Once the sharpest part of the image has been determined, this lateral distance can be measured in pixels, and the values of z', and hence of z, computed. A motor 208 connected to the wafer chuck, is then driven by means of a closed loop control system 209 such that the wafer shifts vertically by a distance z to adjust the focus back to its correct position.

The position of the best focused part of the image is determined by means of an image processing algorithm, activated each time an image is formed on detector 206. According to one preferred embodiment, this algorithm is operative to extract the positions of edges in the image by use of an edge detector, such a Sobel. It then selects for each line of the detector, the maximum edge sharpness value. This may be averaged over several edges, in order to facilitate the measurement, and a graph of the edge value as a function of the position is plotted. The maximum of the graph represents the sharpest part of the image.

Figure 22B:
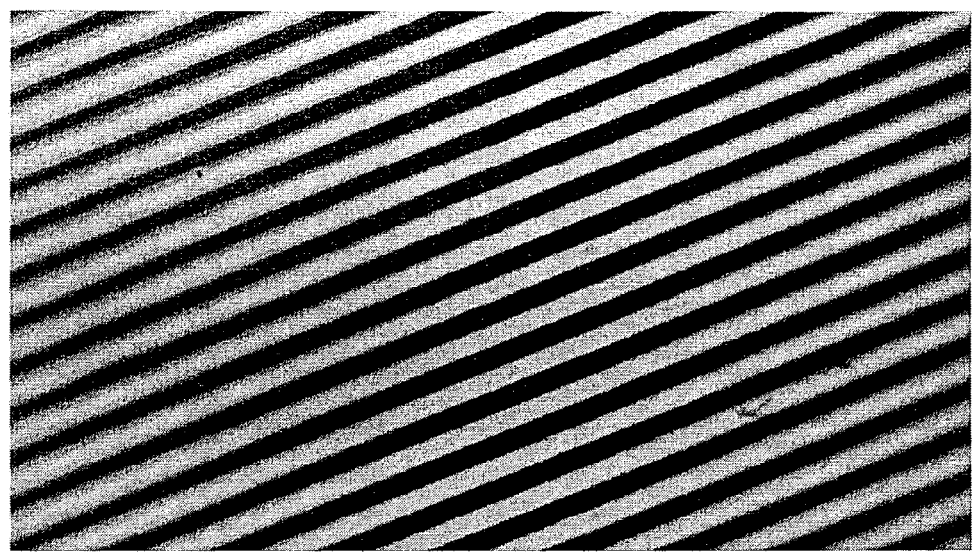
FIG. 22B is a view of the image of a line spacing target, in this case a Ronci ruler, obtained from the autofocus detector used in the embodiment of FIG. 22A.
Figure 22C:
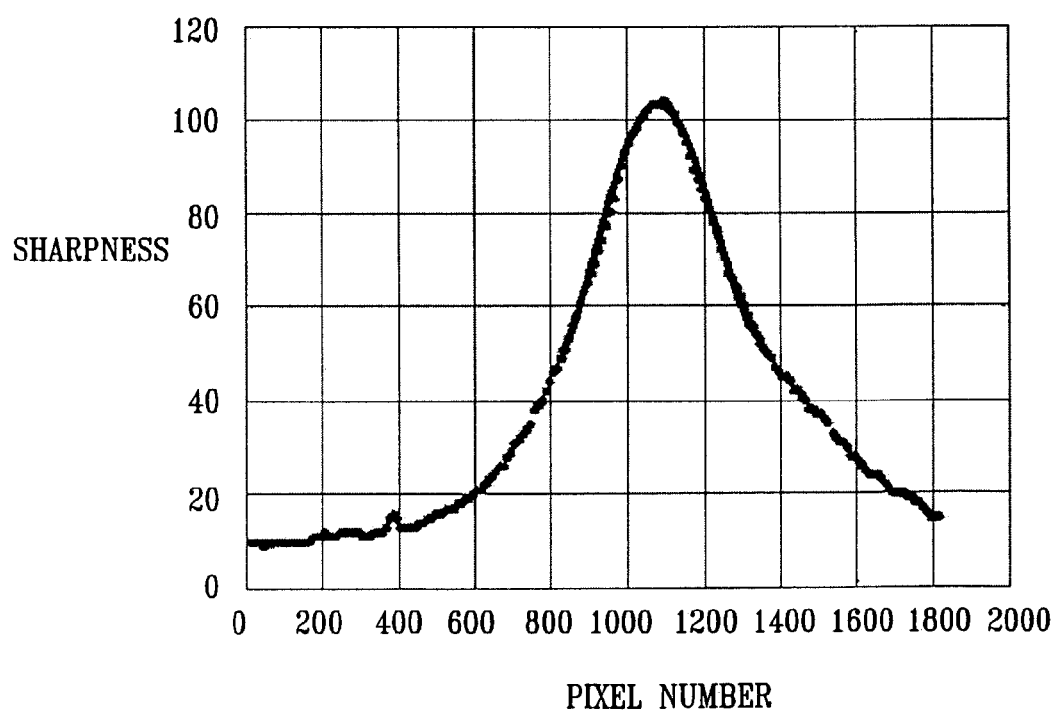
FIG. 22C shows a plot of an edge sharpness analysis of the image in FIG. 22B, to determine the position of optimum focus.

This procedure is illustrated by reference to FIGS. 22B and 22C. FIG. 22B is a view of the image of a line spacing target, in this case a Ronci ruler, obtained from the autofocus detector 206. As is observed in the image, the left and right extremities of the image are blurred, and only the center of the image is in focus. Edge sharpness analysis of this image yields the focal curve shown in FIG. 22C, where the abscissa is the lateral pixel number on the detector and the ordinate is the degree of the sharpness of the image measured per pixel.

The peak of the curve is preferably determined by means of a polynomial best fit algorithm, as shown by the black line through the individual measurement points around the peak of the curve. In the sample curve shown in FIG. 22C, the best focused position in the detector array occurs around pixel No. 1100. The distance, in pixels, between the best-focused pixel position and the nominal correctly focused pixel position, as set during calibration, is translated into the required focal distance change of the wafer by means of a control system.

The detector 206 as shown in FIG. 22A monitoring the output of laser source 500, can also be used, according to another preferred embodiment of the present invention, for compensating the imaging system for changes in the average output level of the laser. The detector 206 is then preferably chosen to be of a type which measures pulse energy output or average power output from the laser. When this measurement shows that the laser pulse energy is falling, which would result in a less intense image of the wafer under inspection, an adjustment is made to the gray-scale levels of the digital image processing circuits, such that the intensity of the displayed or operated-on image is maintained. Though shown with a laser source in the embodiment of FIG. 21A, it is to be understood that this method can also be used for illumination sources other than lasers.

Figure 23A:
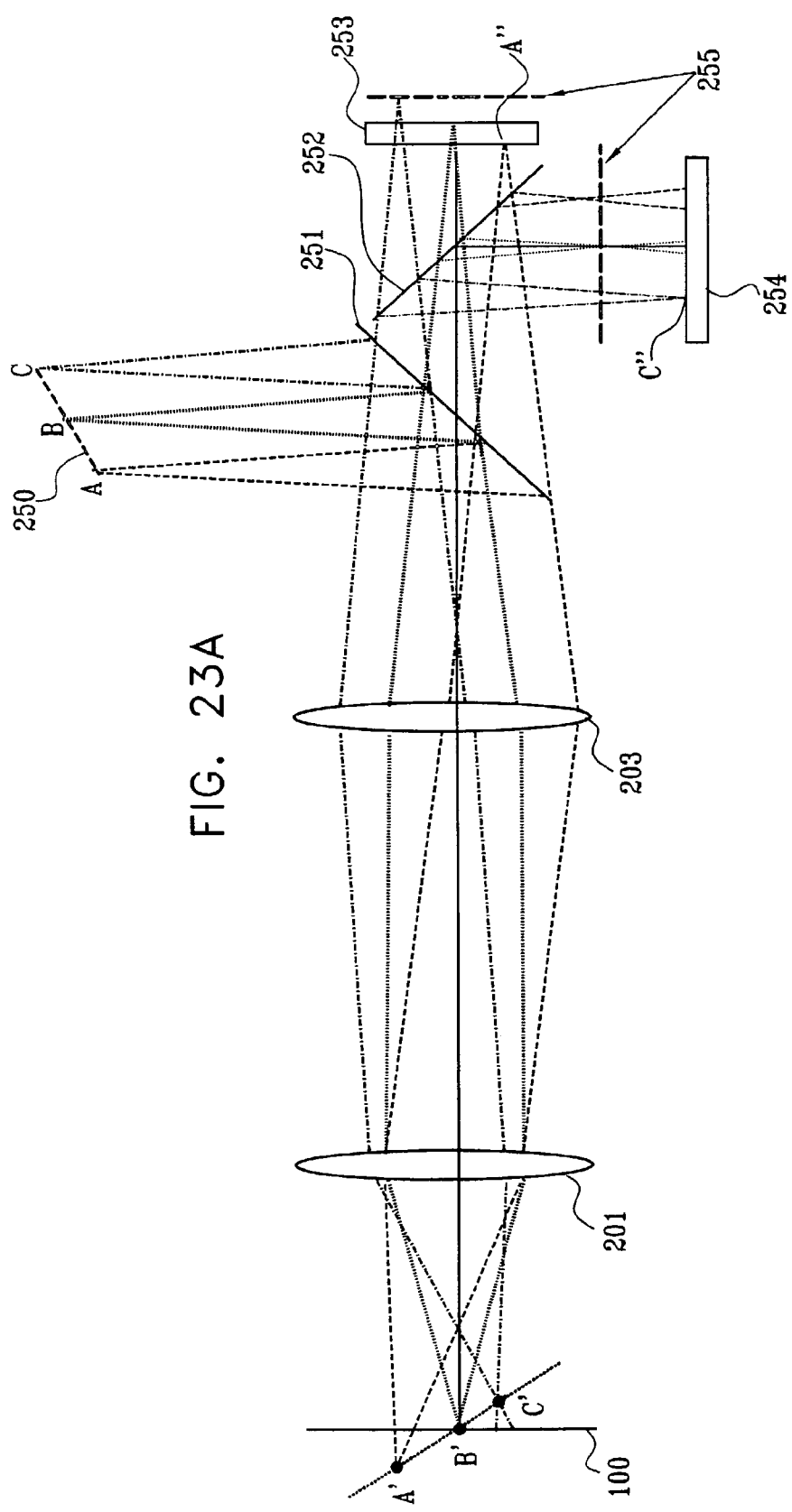
FIG. 23A is a schematic optical diagram used in an alternative and preferred automatic focusing system, using a tilted source of illumination.

Reference is now made to FIG. 23A, which is a schematic optical diagram used on an alternative and preferred automatic focusing system, constructed and operative according to another preferred embodiment of the present invention. This system can be used instead of that shown in the embodiment of FIGS. 22A to 22C, and with improved operation.

Figure 23B:
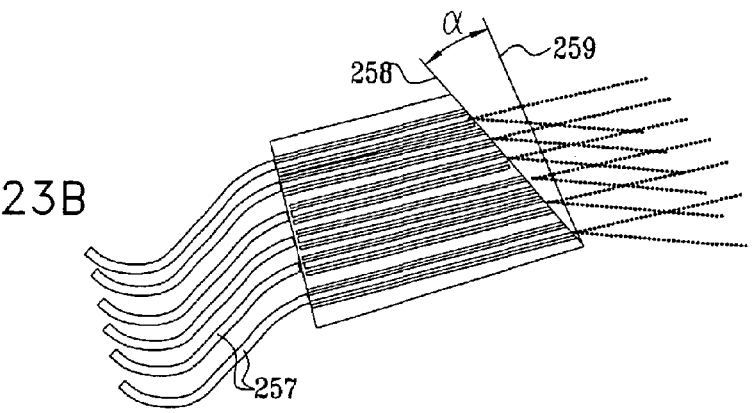
FIG. 23B illustrates a preferred method of obtaining the tilted source beam of FIG. 23A, using a flat array of fibers.

A light source 250, is utilized in the arrangement of FIG. 23A, tilted with respect to a plane normal to the optical axis, such that it has differently distanced points A, B and C across its width. In FIG. 23B is shown one preferred method of obtaining such a tilted source beam. The source comprises a flat array of fibers 257, whose termination plane 258 is polished at an angle α to the normal to the axis of the array, such that the light is emitted from the fiber ends at the same angle. Alternatively and preferably, the light source may also be generated from a tilted mask with holes illuminated by a light source located behind the mask, and through which the desired pattern of spots is injected into the optical path.

The tilted source beam is projected into the optical illumination system by means of a partially reflecting mirror 251, and via the imaging lens 203 and the objective lens 201, onto the object plane 100 to be imaged. Because of the source tilt only the center point B of the autofocusing beam source is imaged at B' on the object plane 100. Points A and C are projected respectively after and before the object plane at points A' and C' respectively. The object plane is imaged by the objective lens 201 and by the imaging lens 203 towards the image plane 255, and this imaging beam is split by a beam splitter 252 which directs the light onto two detectors 253 and 254, preferably one-dimensional CCD arrays, positioned respectively before and after the image plane 255, which is shown in both of its projected positions. The source is located confocally with the image plane, such that a sharp image of the center of the source is produced at the image plane when the object plane is in correct focus.

On each CCD detector 253, 254, because of the tilted source beam, only one point is in focus. Furthermore, since the detectors are located at different positions along the optical axis, any point on the object is detected at a different focal position on the two detectors. Thus, in the embodiment of FIG. 23A, on detector 253, point A is shown to be in focus at A", while on detector 254, point C is in focus at C". The signal obtained from image of each point of the source on the CCD detector depends on the degree of focus of the system. When a source point is well-focused, the energy from that point is spread over small number of pixels on the CCD and the peak signal is high. When a source point is out of focus, the same energy is spread over a large number of pixels on the detector, and the peak signal is thus lower.

Figure 24A:
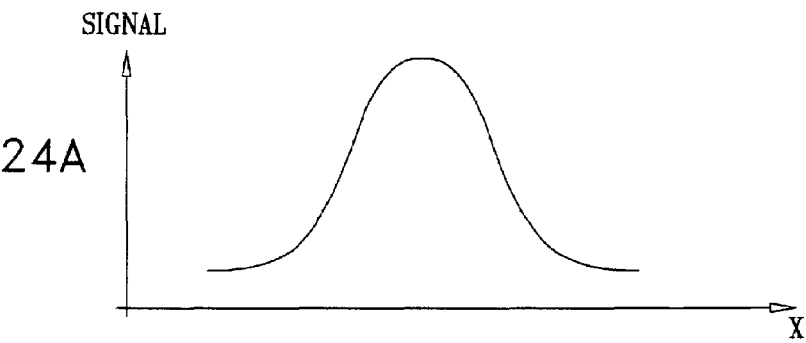
FIGS. 24A to 24C are graphical representations of signals obtained and processed firm the CCD detectors of the embodiment of FIG. 23A used to determine the optimum focal point.
Figure 24B:
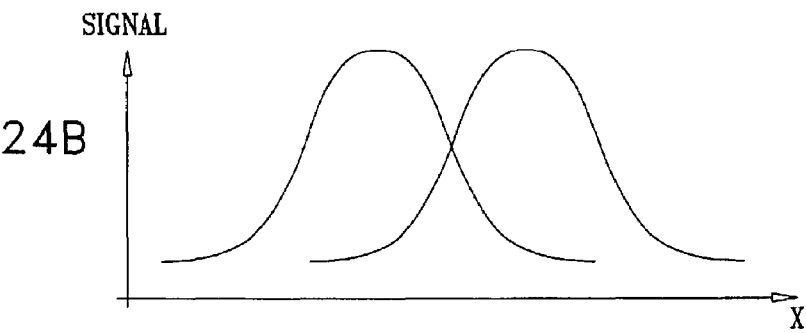
Figure 24C:
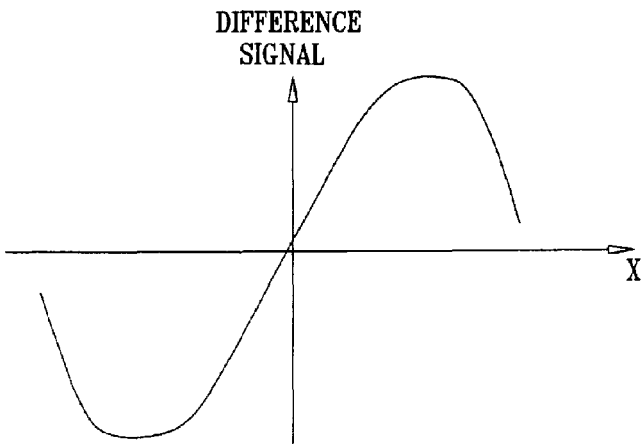

Reference is now made to FIGS. 24A to 24C, which are graphical representations of signals obtained and processed from the CCD detectors, and used to determine the optimum focal point of the object plane. FIG. 24A is a schematic plot of the signal across one of the two CCD detector arrays of the system, for instance, detector 253, for a single point of the object plane 100 focussed onto the array. The peak of the curve indicates the position of optimum focus. In FIG. 24B is now shown the output from the second detector 254 of the image of the same point on the object plane. Since the two detectors are displaced along the optical axis from each other, the positions of the peaks are offset with respect to each other. In FIG. 24C is now shown the result of subtracting the two signals from the two detectors. As is apparent from these plots, the position of best focus for a specific point is obtained when the graph shown in FIG. 24C has a minimum level, and preferably approaches a zero level, indicating perfect focus.

In operation, the object plane 100 is adjusted by means of an autofocussing stage motor 208, like that shown in the autofocussing system of FIG. 22A, and this causes the projected images of the object plane 255 to move accordingly. The signal positions of the images of the source beam thus also change on the detectors 253, 254. A closed loop control system 209, such as that shown in FIG. 22A, is used to move the object plane, shifting the wafer vertically to adjust the focus to its correct position, as indicated by the reduction of the output plot of the difference signal in FIG. 23C to its flattest and lowest level.

According to yet another preferred embodiment of the present invention, the autofocussing system of FIG. 23A can be implemented in a simpler manner by using only one detector located at the image plane. This embodiment is then complementary to that shown in FIG. 22A, in that the tilted positions of the detector and the source are reversed. In the embodiment of FIG. 22A, the source is disposed perpendicular to the optical axis, and the detector is tilted. In the single detector embodiment of FIG. 23A, the source 250 is tilted, and the single detector used is disposed perpendicular to the optical axis. Most simply, the detector shown as 253 is used, as it is disposed in a position such that the beam splitter 252 is not required.

The autofocussing system described in FIGS. 23A to 24C has a number of advantages over other autofocussing systems, as follows:
1. The projection of the autofocussing source onto the wafer eliminates dependence of the system on the pattern of the wafer, and allows its use even on an unpatterned wafer.
2. The use of two CCD detectors which image the same pattern, reduces undesired sensitivity to changes in light intensity of the source. Such use is operative to normalize the results and make them invariant to light level differences at different points of focus.
3. The deviation from focus is measured accurately without dependence on the intensity.
4. Since the light travels twice through the same optics in opposite directions, some aberrations are canceled.
5. The Depth of Focus is reduced by the double passage through the objective lens thus making the sensitivity of the system very high.

An object of the system of the present invention is the detection of small defects and anomalies hidden in the image of a multiply repetitive region of a pattern covering a wafer. This task is not a simple one, because of the need to filter out the pattern information from the image without effecting the signal obtained from a defect. According to another preferred embodiment of the present invention, this task is facilitated by the use of Fourier filtering.

The geometry on a semiconductor wafer generally consists of a large-scale multiply repetitive pattern that defined the dies of the wafer. Within each die, there are often areas in which there appears an array of a repetitive pattern with a cycle of a few microns. This occurs especially in memory chips or in the memory area in a logic chip. When coherent or partial coherent illumination is incident on such a periodic array, the array serves as a diffraction grating that reflects the light only in the defined Bragg angles. The reflected light produces a diffraction patter of spots in the back focal plane of the objective lens. This plane is also referred as the Fourier plane of the lens, since the image obtained in this plane is a two-dimensional Fourier transform of the object. The smaller the cycle in the object plane, the larger the distance between the spots in the Fourier plane. The size of these spots depends on the optical quality of the objective lens, but even more on the nature of the incident light. When the input light is a collimated beam, the spot size is very small. In U.S. Pat. No. 5,970,168 to Montesanto et al., for "Fourier Filtering Mechanism for Inspecting Wafers" there is described the use of a spring array as a Fourier plane filter, with a built-in damping mechanism to prevent interference from mechanical vibrations. However, this prior art always relates to use of a laser as the light source, which is a collimated coherent light source.

According to a further preferred method of the present invention, an extended source which need be only partially coherent, as used in the dark field side illumination embodiments of the present invention, is used to produce defined spots in the Fourier plane. According to this preferred method, when the illuminating beam is such an extended light source, the size and shape of each of the spots in the Fourier plane becomes a miniature image of the extended source. Furthermore, in order to produce the diffraction pattern in the Fourier plane, it is not necessary that each point in the extended source be a coherent source. This extended and partially coherent form of illumination is successful in generating a Fourier plane diffraction pattern array, because each separate area of the illuminating beam is made up of an assembly of self coherent spots, but unrelated to each other. This is an outcome of the optical treatment performed on the illuminating beam by means of the imaging optics for the fiber optical output. Furthermore, when the cycle of the repetitive pattern is sufficiently small, as in many semiconductor wafers, the spots do not overlap and cover only a relatively small part of the objective pupil. If the structural periodic information from the image can be filtered out, the optical information anomalies resulting from defects on the wafer can be revealed in the form of non-periodic information spread over a wide range of spatial frequencies. This is performed in practice by blocking the transmission of light specifically in the area of those spots, eliminating the information relevant to the repetitive pattern from the image from the remaining optical information transmitted past the Fourier plane, thus making it possible to detect anomalies caused by departures from the desired pattern on the wafer.

Figure 25:
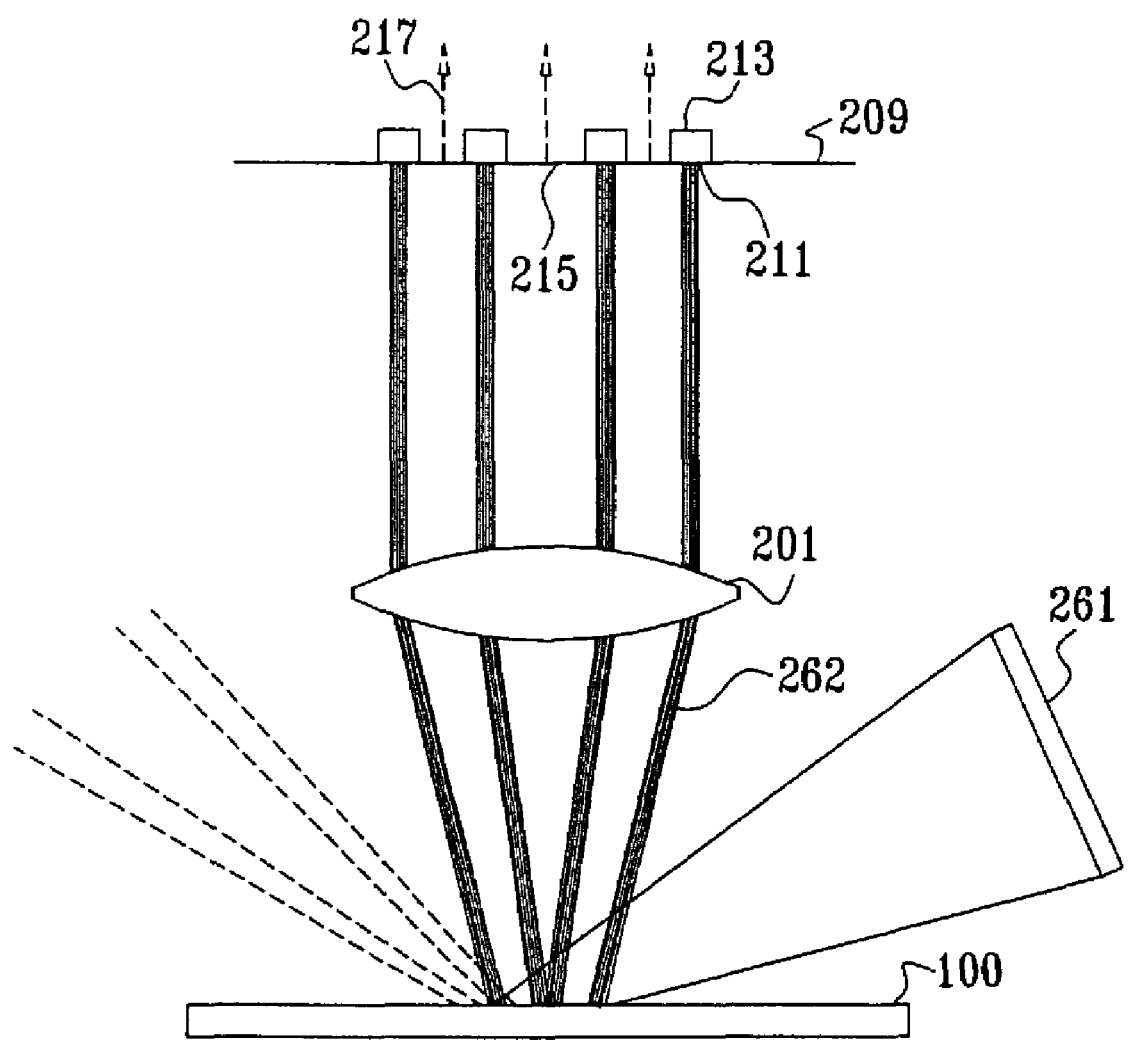
FIG. 25 is a schematic illustration of a dark field arrangement for filtering out structural periodic information related to the image, from the objective back focal plane.

Reference is now made to FIG. 25, which schematically illustrates a preferred method for performing this procedure. An extended source 261, which can even be non-parallel, as preferably used in the dark field side illumination embodiment shown in FIG. 14A above, is incident on the wafer 100 under inspection. The scattered light 262 from the wafer features, is imaged by the objective lens 201. At the back focal plane 209 of this lens, which is the above-mentioned Fourier plane, there is generated a patterned array of spots 211 representing the repetitive features of the wafer being imaged by the scattered light. In the interstitial positions 215 between these spots, there may appear any light scattered from non-repetitive features on the wafer die, such as from a defect which it is desired to detect. A mask 213, constructed to exactly block the light from the predetermined patterned array of spots 211, is disposed at the Fourier plane, thus allowing scattered light 217 from defects present on the wafer die to pass the Fourier plane, and to be imaged and detected by the system, without interference from the expected repetitive features of the wafer die.

Figure 26A:
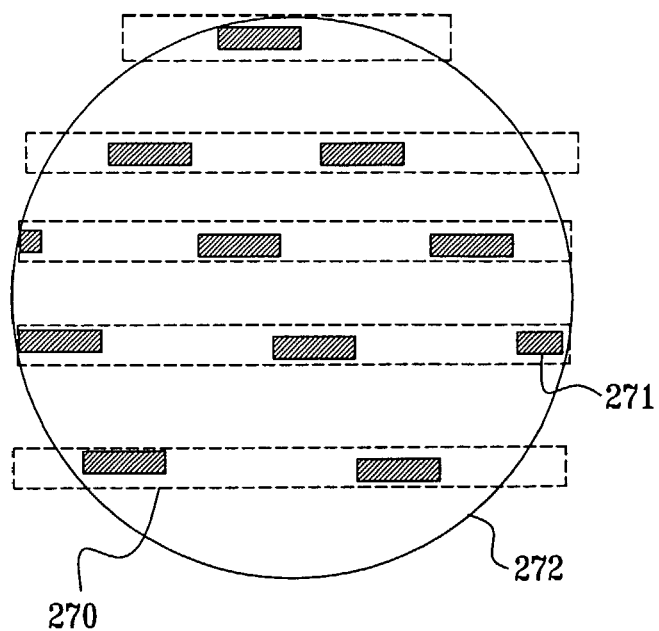
FIG. 26A schematically illustrates a fixed Fourier plane blocking array, such as for use in the embodiment of FIG. 25.
Figure 26B:
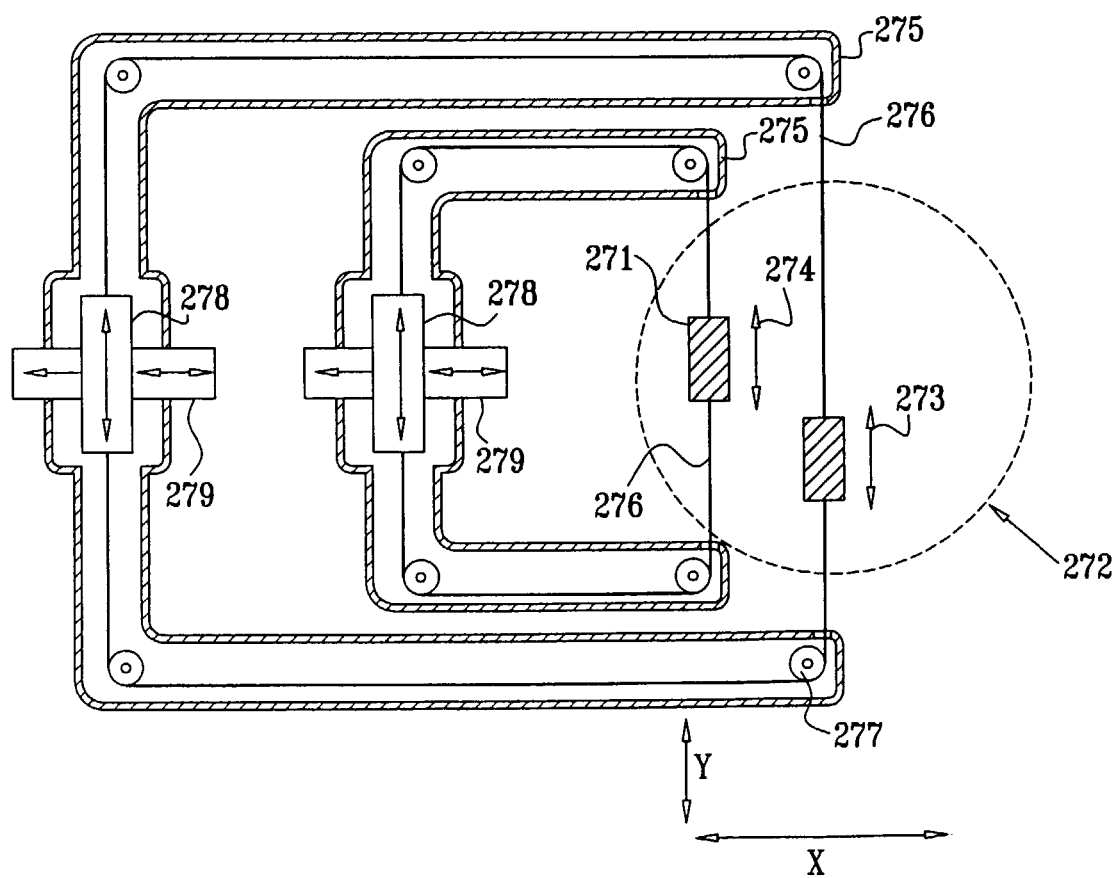
FIG. 26B schematically illustrates an adjustable mechanical array of blocking bars using thin adjusting wires to which the bars are attached, such as for use in the embodiment of FIG. 25.

According to alternative and preferable embodiments, the Fourier plane filter can be constructed either as a fixed mask, or by using a spatial light modulator (SLM) made of Liquid Crystal Display (LCD) or by using a mechanical array of small bars that can be physically shifted to change the cycle and phase of the mask in the Fourier plane. Reference is now made to FIG. 26A which illustrates a fixed mask blocking array 270 located over the Fourier plane aperture 272, such that the multiple order diffraction images 271 of the extended source are effectively blocked. Reference is also now made to FIG. 26B, which schematically illustrates a mechanical array of blocking bars 271, whose positions are adjusted 273, 274, to that of the required array by means of thin adjustable wires 276, to which the bars are attached. The wires are so thin that they do not block light related to any imaging information. The wire associated with each bar is mounted on a frame 275, including pulley wheels 277 on the corners to allow free motion to the desired position, a translation motor 278 for moving each wire in the Y-direction, and a further translation motor 279 for moving the entire frame in the X-direction. In this way, the predetermined blocking array can be set electronically, and locked into place. In the embodiment shown in FIG. 26B, for clarity, only two blocking bars are shown, but it is to be understood that a larger number can also be provided. The number of blocking bears necessary for a particular application depends upon the density of the features on the wafer. The higher the spatial period of the features on the wafer the smaller the number of orders seen in the Fourier plane, and the less the number of blocking bars required. Thus for example, when inspecting a memory array made in 90 nanometer technology, only 2 to 3 orders will enter a 0.6 NA objective lens, and thus only 2 to 3 blocking bars are required.

In order to actively adapt a spatial Fourier filter design to a specific layer, it is useful to view the image obtained in this plane. Usually the Fourier plane is the back focal plane of the objective, or if inaccessible, as with many high power objective designs, an image of this plane.

Figure 27:
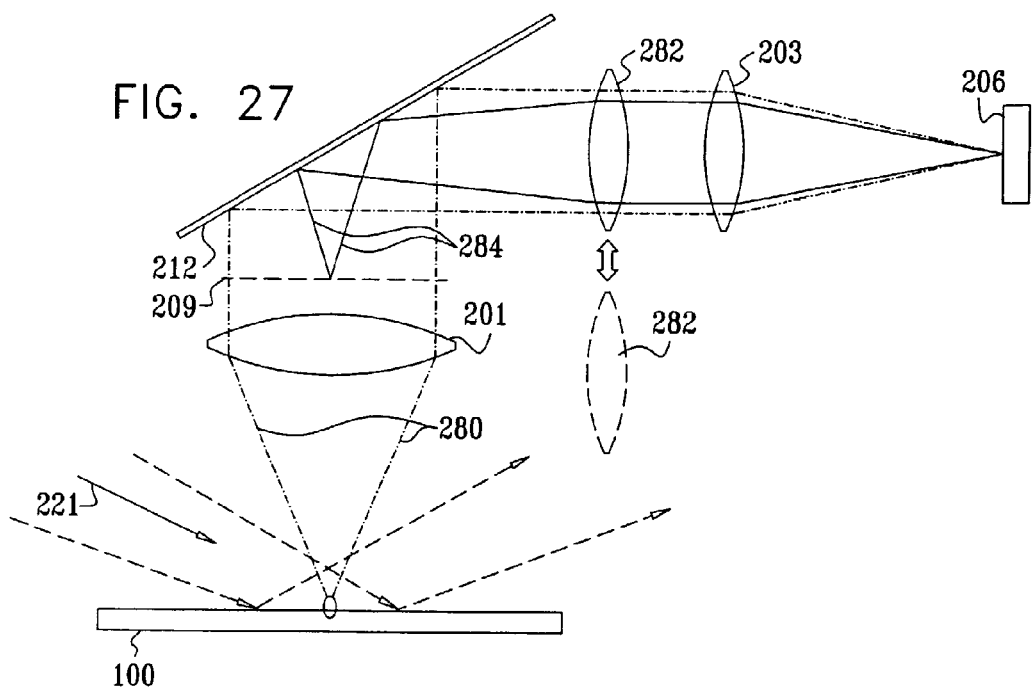
FIG. 27 illustrates a method, according to another preferred embodiment of the present invention, by which the back focal plane of the objective can be imaged onto the detector using an additional lens.

Reference is now made to FIG. 27, which illustrates a method, according to another preferred embodiment of the present invention, by which this plane can be imaged onto the existing detector by introducing an additional lens into the imaging optics. In the embodiment of FIG. 27, dark field side illumination 221 is incident on the wafer 100, and the scattered light, as designated by the dashed lines 280, is collected by the objective 201, for imaging on the detector 206 by means of the detector imaging lens 203, all as previously described hereinabove.

The Fourier plane 209 is located behind the objective lens 201, and may be in a position where it is not easy to locate a detector for direct imaging. Therefore, when the Fourier plane has to be viewed in order to determine the correct Fourier plane filter to construct, an additional imaging lens 282, known as the Fourier imaging lens, is inserted into the imaging path, increasing the power of the detector imaging system, such that the detector now images the Fourier plane 209. The solid lines 284 in FIG. 27 represent the optical imaging path from the Fourier plane to the detector, with the Fourier imaging lens in position. In this manner, the exact required pattern of the spatial filter in the Fourier plane for a specific die region can be designed according to the imaged field of the object. This filter can then be implemented either by control over the spatial filter, such as an LCD or another type of spatial filter, or the output used to construct a fixed filter.

Figure 28:
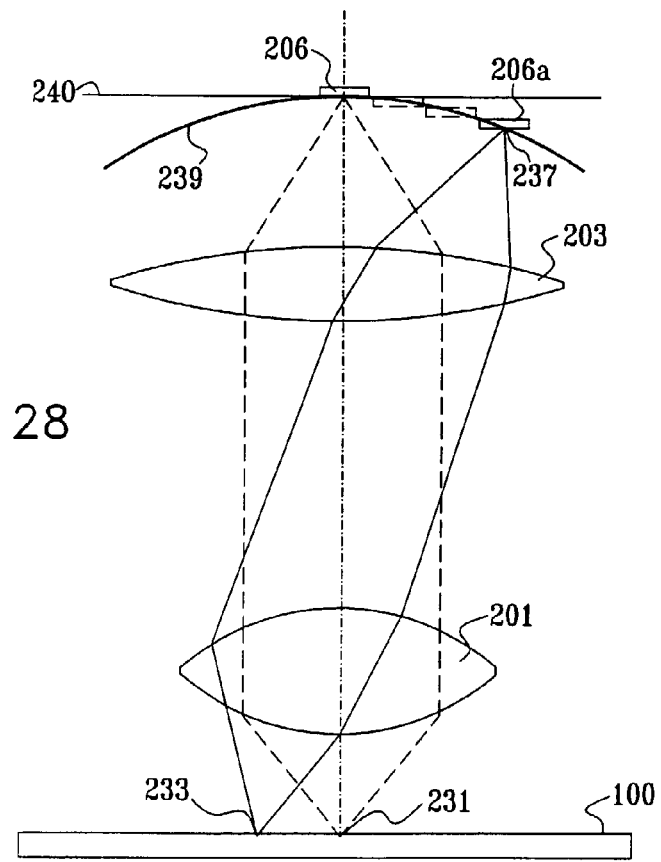
FIG. 28 is a schematic illustration of an optical arrangement, according to another preferred embodiment of the present invention, of correction of the field curvature of the optical imaging system of the inspection apparatus of the present invention.

Since the scanning of the wafer using the inspection system of the present invention, is preferably performed over a large field of view, a full die size can generally be covered by only a few images. Thus, for example, using an inspection area of 4×4 mm, which is feasible with the inspection system of the present invention because of its large imaging field of view, a typical 10×10 mm die can be covered with only nine image frames. For each frame, the best shape of the filter of the die region imaged by the tool can therefore be learned in advance. According to another preferred embodiment of the present invention, different filter masks can be generated in real time during the inspection process, by insertion of the above-described Fourier imaging lens 282 between execution of each region's real imaging inspection. Each mask is optimized to block the light from the repetitive pattern from the area of the die currently being imaged. Thus, for example, the repetitive pattern of a logic area of a chip may have one type of period, and thus require its own Fourier filter mask, while that of a memory section of the chip would require a different type and period of mask. The use of a spatial light modulator, such as an LCD, as the Fourier mask, enables this to be done in real time. Thus, the Fourier pattern of the entire chip can be learned during initial inspection, using the insertable Fourier imaging lens 282 of the present invention, and correction masks programmed into a SLM device for repetitive use during on-line inspection. Such real time Fourier filtering is difficult, if at all feasible, with prior art wafer inspection systems which utilize line inspection. Reference is now made to FIG. 28, which is a schematic illustration of a method, according to another preferred embodiment of the present invention, of correction of the field curvature of the optical imaging system of the defect inspection apparatus of the present invention. As is known from the art, optical imaging systems generally display an aberration known as image field curvature, in which the focal plane generated by the imaging system is not flat, but displays a curved profile around the optical axis. Though this aberration can be corrected by use of an auxiliary lens known as a field flattener, this involves an additional optical element and the correction may not always be complete over the whole field of view.

FIG. 28 is a simplified view of the imaging optics illumination path from the wafer under inspection 100, through the objective lens 201 and the detector imaging lens 203, and onto the detector 206 situated on the focal plane of the imaging lens. For an axial ray originating from a point, the position of best focus is on the focal plane 240, where detector 206 is positioned. However, for an off-axis ray, imaged from a point 233 distant from the center of the field of view, the position of best focus falls, because of the effects of the field curvature of the imaging, optics, at point 237, and this is where the detector 206a should be positioned for optimum focus. The line of best focus is shown as the field curve 239.

Using the preferred embodiments of FIGS. 5C and 5D, where easy access is available to the longitudinal position of each detector array, there is provided a further preferred embodiment of the present invention, whereby field curvature is compensated by disposing each detector essentially on the line of the field curvature 239, such that each ray imaged by the system, is sharply in focus. In FIG. 28, a series of such detector positions extending from reference numeral 206 to reference numeral 206a is shown.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. An inspection system for inspecting objects comprising:
an imager operative to image said imager employing at least two 2-dimensional detectors the surfaces of which define a focal plane, each of said at least two 2-dimensional detectors being focused on an at least partially different area of said objects and providing a 2-dimensional digital output;
a transporter for providing relative motion between said imager and said objects along said travel path;
a pulsed laser illuminator for illuminating said objects as they travel along said travel path;
an optical subsystem including at least one beam splitter and at least one fully reflective optical element, which is separate from said beam splitter, said at least one beam splitter and said at least one reflective optical element being operative together to split an image of said focal plane between ones of said at least two 2-dimensional detectors; and wherein said at least two 2-dimensional detectors comprise at least four detector ensembles, each including at least one 2-dimensional detector, and said image of said focal plane is split between said at least four detector ensembles such that each of said at least four detector ensembles receives at least approximately 33% of light reflected, scattered and diffracted from said objects onto said focal plane and said focal plane comprises a continuous surface on adjacent ones of said detectors included in said at least four detector ensembles.

2. An inspection system according to claim 1 and wherein said at least one reflective optical element comprises at least two reflective optical elements, said image being split into portions by said at least one beam splitter and subsequently each of said portions is split by one of said at least two reflective optical elements, said at least two reflective elements and said at least two 2-dimensional detectors being arranged to provide a generally continuous optical surface.

3. An inspection system according to claim 1 and wherein said at least four detector ensembles comprise at least six detector ensembles.

* * * * *